US006958358B2

(12) United States Patent
Quibell et al.

(10) Patent No.: US 6,958,358 B2
(45) Date of Patent: Oct. 25, 2005

(54) INHIBITORS OF CRUZIPAIN AND OTHER CYSTEINE PROTEASES

(75) Inventors: Martin Quibell, Cambridge (GB); Manoj Kumar Ramjee, Cambridge (GB)

(73) Assignee: Amura Therapeutics Limited (GB)

( * ) Notice: Subject to any disclaimer, the term of this patent is extended or adjusted under 35 U.S.C. 154(b) by 49 days.

(21) Appl. No.: 10/466,385

(22) PCT Filed: Jan. 17, 2002

(86) PCT No.: PCT/GB02/00194

§ 371 (c)(1), (2), (4) Date: Jan. 8, 2004

(87) PCT Pub. No.: WO02/057246

PCT Pub. Date: Jul. 25, 2002

(65) Prior Publication Data

US 2004/0106805 A1 Jun. 3, 2004

Related U.S. Application Data

(60) Provisional application No. 60/275,506, filed on Mar. 13, 2001.

(30) Foreign Application Priority Data

Jan. 17, 2001 (GB) ............................................. 0101204

(51) Int. Cl.[7] ..................... A61K 31/343; A61K 31/381; C07D 307/93; C07D 495/00
(52) U.S. Cl. .......................... 514/443; 514/470; 549/33; 549/465; 549/466
(58) Field of Search ............................. 514/443, 470; 549/33, 465, 466

(56) References Cited

U.S. PATENT DOCUMENTS 3,652,574 A    3/1972    Garmaise ................... 260/296

FOREIGN PATENT DOCUMENTS

| WO | 98/05336 | 2/1998 |
| WO | 98/08802 | 3/1998 |
| WO | 98/28268 | 7/1998 |
| WO | 98/50533 | 11/1998 |
| WO | 99/53039 | 10/1999 |
| WO | 00/29408 | 5/2000 |
| WO | 02/040462 | 5/2000 |
| WO | 00/69855 | 11/2000 |
| WO | 02/051983 | 7/2002 |

OTHER PUBLICATIONS

Fenwick, et al., "Diastereoselective Synthesis, Activity and Chiral Stability of Cyclic Alkoxyketone Inhibitors of Cathepsin K," *Bioorganic & Medicinal Chemistry Letters*, vol. 11, pp. 199–202 (2001).

Marquis, et al., "Conformationally Constrained 1, 3–Diamino Ketones: A Series of Potent Inhibitors of the Cysteine Protease Cathepsin K," *J. Med. Chem.*, vol. 41, pp. 3563–3567 (1998).

*Primary Examiner*—Taofiq Solola
(74) *Attorney, Agent, or Firm*—Wilmer Cutler Pickering Hale and Dorr LLP

(57) ABSTRACT

Compounds of general formula (I):

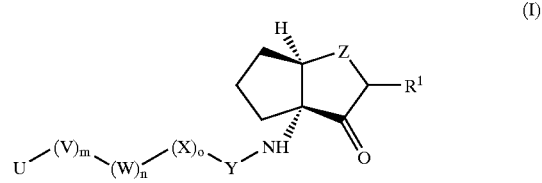

wherein $R^1$, Y, $(X)_o$, $(W)_n$, $(V)_m$, Z and U are as defined in the specification, are inhibitors of cruzipain and other cysteine protease inhibitors and are useful as therapeutic agents, for example in Chagas' disease, or for validating therapeutic target compounds.

35 Claims, No Drawings

INHIBITORS OF CRUZIPAIN AND OTHER CYSTEINE PROTEASES

THIS INVENTION relates to compounds which are inhibitors of the protease cruzipain, a gene product of the Trypanosoma cruzi parasite. In particular, the invention provides compounds that are useful for the therapeutic treatment of Trypanosoma cruzi infection, to the use of these compounds, and to pharmaceutical compositions comprising them. Furthermore, this invention relates to compounds which are inhibitors across a broad range of cysteine proteases, to the use of these compounds, and to pharmaceutical compositions comprising them. Such compounds are useful for the therapeutic treatment of diseases in which participation of a cysteine protease is implicated.

The trypanosomal family of parasites have a substantial worldwide impact on human and animal healthcare (McKerrow, J. H., et al, Ann. Rev. Microbiol. 47 821–853, 1993). One parasite of this family, Trypanosoma cruzi, is the causative agent of Chagas' disease, which affects in excess of twenty million people annually in Latin and South America, is the leading cause of heart disease in these regions and results in more than 45,000 deaths per annum (Centers for Disease Control and prevention website). In addition, with the increase in migration of the infected population from rural to urban sites and movements from South and Central America into North America, the infection is spreading via blood transfusions, and at birth. The present treatments of choice for Trypanosoma cruzi infection, nifurtimox and benznidazole (an NADH fumarate reductase inhibitor, Turrens, J F, et al, Mol Biochem Parasitol., 82(1), 125–9, 1996) are at best moderately successful, achieving ~60% cure during the acute phase of infection (see Docampo, R. Curr. Pharm. Design, 7, 1157–1164, 2001 for a general discussion) whilst not being prescribed at all during the chronic phase where cardiomyopathy associated heart failure often occurs (Kirchhoff, L. V. New Engl. J. Med., 329, 639–644, 1993). Additionally, these two drugs have serious adverse toxic effects, requiring close medical supervision during treatment, and have been shown to induce chromosomal damage in chagastic infants (Gorla, N. B. et al, Mutat. Res. 206, 217–220, 1988). Therefore, a strong medical need exists for new effective drugs for the chemotherapeutic treatment of Trypanosoma cruzi infection. Classically, the identification of enzymes found to be crucial for the establishment or propagation of an infectious disease has been instrumental in the development of successful drugs such as antivirals (e.g. HIV aspartyl protease inhibitors) and anti-bacterials (e.g. β-lactam antibiotics). The search for a similar Achilles heel in parasitic infections has examined numerous enzymes (e.g. parasitic dihydrofolate reductase, see Chowdhury, S. F. et al, J. Med. Chem., 42(21), 4300–4312, 1999; trypanothione reductase, see Li, Z. et al, Bioorg. Med. Chem. Lett., 11(2), 251–254, 2001; parasitic glyceraldehydes-3-phosphate dehydrogenase, see Aranov, A. M. et al, J. Med. Chem., 41(24), 4790–4799, 1998). A particularly promising area of research has identified the role of cysteine proteases, encoded by the parasite, that play a pivotal role during the life cycle of the parasite (McKerrow, J. H., et al, Bioorg. Med. Chem., 7, 639–644, 1999). Proteases form a substantial group of biological molecules which to date constitute approximately 2% of all the gene products identified following analysis of several genome sequencing programmes (e.g. see Southan, C. J. Pept. Sci, 6, 453–458, 2000). Proteases have evolved to participate in an enormous range of biological processes, mediating their effect by cleavage of peptide amide bonds within the myriad of proteins found in nature. This hydrolytic action is performed by initially recognising, then binding to, particular three-dimensional electronic surfaces displayed by a protein, which aligns the bond for cleavage precisely within the protease catalytic site. Catalytic hydrolysis then commences through nucleophilic attack of the amide bond to be cleaved either via an amino acid side-chain of the protease itself, or through the action of a water molecule that is bound to and activated by the protease. Proteases in which the attacking nucleophile is the thiol side-chain of a Cys residue are known as cysteine proteases. The general classification of 'cysteine protease' contains many members found across a wide range of organisms from viruses, bacteria, protozoa, plants and fungi to mammals.

Biological investigation of Trypanosoma cruzi infection has highlighted a number of specific enzymes that are crucial for the progression of the parasite's life cycle. One such enzyme, cruzipain, a cathepsin L-like cysteine protease, is a clear therapeutic target for the treatment of Chagas' disease ((a) Cazzulo, J. J. et al, Curr. Pharm. Des. 7, 1143–1156, 2001; (b) Caffrey, C. R. et al, Curr. Drug Targets, 1, 155–162, 2000). Although the precise biological role of cruzipain within the parasite's life cycle remains unclear, elevated cruzipain messenger RNA levels in the epimastigote developmental stage indicate a role in the nutritional degradation of host-molecules in lysosomal-like vesicles (Engel, J. C. et al, J. Cell. Sci, 111, 597–606, 1998). The validation of cruzipain as a viable therapeutic target has been achieved with increasing levels of complexity. Addition of a general cysteine protease inhibitor, Z-Phe-Ala-FMK to Trypanosoma cruzi-infected mammalian cell cultures blocked replication and differentiation of the parasite, thus arresting the parasite life cycle (Harth, G., et al, Mol. Biochem. Parasitol. 58, 17–24, 1993). Administration of a vinyl sulphone-based inhibitor in a Trypanosoma cruzi-infected murine animal model not only rescued the mice from lethal infections, but also produced a complete recovery (Engel, J. C. et al, J. Exp. Med, 188(4), 725–734, 1998). Numerous other in vivo studies have confirmed that infections with alternative parasites such as Leishmania major (Selzer, P. M. et al, Proc. Nat'l. Acad. Sci. U.S.A., 96, 11015–11022, 1999), Schistosoma mansoni and Plasmodium falciparium (Olson, J. E. et al, Bioorg. Med. Chem., 7, 633–638, 1999) can be halted or cured by treatment with cysteine protease inhibitors.

A variety of synthetic approaches have been described towards the design of cruzipain inhibitors. However, although providing a biological 'proof-of-principle' for the treatment of Trypanosoma cruzi infection, current inhibitors exhibit a number of biochemical and physical properties that may preclude their clinical development. (e.g. see (a) Brinen, L. S. et al, Structure, 8, 831–840, 2000, peptidomimetic vinyl sulphones, possible adverse mammalian cell toxicity (see McKerrow, J. H. and Engel, J. unpublished results cited in Scheidt, K. A. et al, Bioorg. Med. Chem, 6, 2477–2494, 1998); (b) Du, X. et al, Chem. Biol., 7, 733–742, 2000, aryl ureas, generally with low $\mu$M activity, and high ClogP values, thus poor aqueous solubility and probably low oral bioavailability; (c) Roush, W. R. et al, Tetrahedron, 56, 9747–9762, 2000, peptidyl epoxysuccinates, irreversible inhibitors, with potent activity verses house-keeping mammalian proteases such as cathepsin B; (d) Li, R. et al, Bioorg. Med. Chem. 4(9), 1421–1427, 1996, bisarylacylhydrazides and chalcones, polyhydroxylated aromatics; (e) U.S. Pat. No. 6,143,931, WO 9846559, non-peptide α-ketoamides). Of the many different approaches to enzyme inhibition to date, only the cruzipain protease inhibitors have proven effective in curing disease-related animal models of *Trypanosoma cruzi* infection. Therefore, a clear medical need exists to progress these 'proof-of-principle' findings towards clinical candidates, suitable for human use, through the discovery of more efficacious cruzipain inhibitors that have a desirable combination of potency, selectivity, low toxicity and optimised pharmacokinetic parameters.

Cruzipain and indeed many other crucial parasitic proteases belong to the papain-like CA C1 family and have close structural mammalian homologues. Cysteine proteases are classified into 'clans' based upon a similarity in the three-dimensional structure or a conserved arrangement of catalytic residues within the protease primary sequence. Additionally, 'clans' are further classified into 'families' in which each protease shares a statistically significant relationship with other members when comparing the portions of amino acid sequence which constitute the parts responsible for the protease activity (see Barrett, A. J et al, in 'Handbook of Proteolytic Enzymes', Eds. Barrett, A. J., Rawlings, N. D., and Woessner, J. F. Publ. Academic Press, 1998, for a thorough discussion). To date, cysteine proteases have been classified into five clans, CA, CB, CC, CD and CE (Barrett, A. J. et al, 1998). A protease from the tropical papaya fruit 'papain' forms the foundation of clan CA, which currently contains over 80 distinct and complete entries in various sequence databases, with many more expected from the current genome sequencing efforts. Proteases of clan CA/family C1 have been implicated in a multitude of disease processes e.g. human proteases such as cathepsin K (osteoporosis), cathepsin S (autoimmune disorders), cathepsin L (metastases) or parasitic proteases such as falcipain (malaria parasite *Plasmodium falciparum*), cruzipain (*Trypanosoma cruzi* infection). Recently a bacterial protease, staphylopain (*S. aureus* infection) has also been tentatively assigned to clan CA. X-ray crystallographic structures are available for a range of the above mentioned proteases in complex with a range of inhibitors e.g. papain (PDB entries, 1pad, 1pe6, 1pip, 1pop, 4pad, 5pad, 6pad, 1ppp, 1the, 1csb, 1huc), cathepsin K (1au0, 1au2, 1au3, 1au4, 1atk, 1mem, 1bgo, 1ayw, 1ayu), cathepsin L (1cs8), cathepsin S (currently on-hold, but published McGrath, M. E. et al, *Protein Science*, 7, 1294–1302, 1998), cretin (a recombinant form of cruzipain see Eakin, A. E. et al, 268(9), 6115–6118, 1993) (1ewp, 1aim, 2aim, 1F29, 1F2A, 1F2B, 1F2C), staphylopain (1cv8). Each of the structures displays a similar overall active-site topology, as would be expected by their 'clan' and 'family' classification and such structural similarity exemplifies one aspect of the difficulties involved in discovering a selective inhibitor of cruzipain suitable for human use. However, subtle differences in terms of the depth and intricate shape of the active site groove of each CA C1 protease are evident, which may be exploited for selective inhibitor design. Additionally, many of the current substrate-based inhibitor complexes of CA C1 family proteases show a series of conserved hydrogen bonds between the inhibitor and the protease backbone, which contribute significantly to inhibitor potency. Primarily a bidentate hydrogen-bond is observed between the protease Gly66 (C=O)/inhibitor N—H and the protease Gly66(NH)/ inhibitor (C=O), where the inhibitor (C=O) and (NH) are provided by an amino acid residue <u>NHCHRCO</u> that constitutes the S2 sub-site binding element within the inhibitor (see Berger, A. and Schecter, I. *Philos. Trans. R. Soc. Lond.* [*Biol.*], 257, 249–264, 1970 for a description of protease binding site nomenclature). A further hydrogen-bond between the protease main-chain (C=O) of asparagine or aspartic acid (158 to 163, residue number varies between proteases) and an inhibitor (N—H) is often observed, where the inhibitor (N—H) is provided by the S1 sub-site binding element within the inhibitor. Thus, the motif X—<u>NHCHR CO—NH</u>—Y is widely observed amongst the prior art substrate-based inhibitors of CA C1 proteases.

In the prior art, the development of cysteine protease inhibitors for human use has recently been an area of intense activity. Considering the CA C1 family members, particular emphasis has been placed upon the development of inhibitors of human cathepsins, primarily cathepsin K (osteoporosis), cathepsin S (autoimmune disorders) and cathepsin L (metastases), through the use of peptide and peptidomimetic nitriles (e.g. see WO-A-0109910, WO-A-0051998, WO-A-0119816, WO-A-9924460, WO-A-0049008, WO-A-0048992, WO-A-0049007, WO-A-0130772, WO-A-0055125, WO-A-0055126, WO-A-0119808, WO-A-0149288, WO-A-0147886), linear and cyclic peptide and peptidomimetic ketones (e.g. see Veber, D. F. and Thompson, S. K., *Curr. Opin. Drug Discovery Dev.*, 3(4), 362–369, 2000, WO-A-0170232, WO-A-0178734, WO-A-0009653, WO-A-0069855, WO-A-0029408, WO-A-0134153 to WO-A-0134160, WO-A-0029408, WO-A-9964399, WO-A-9805336, WO-A-9850533), ketoheterocycles (e.g. see WO-A-0055144, WO-A-0055124) and monobactams (e.g. see WO-A-0059881, WO-A-9948911, WO-A-0109169). The prior art describes potent in vitro inhibitors, but also highlights the many difficulties in developing a human therapeutic. For example, WO-A-9850533 and WO-A-0029408 describe compounds that may be referred to as cyclic ketones and are inhibitors of cysteine proteases with a particular reference towards papain family proteases and as a most preferred embodiment, cathepsin K. WO-A-9850533 describes compounds subsequently detailed in the literature as potent inhibitors of cathepsin K with good oral bioavailability (Witherington, J., 'Tetrahydrofurans as Selective Cathepsin K Inhibitors', RSC meeting, Burlington House, London, 1999). The compounds of WO-A-9850533 were reported to bind to cathepsin K through the formation of a reversible covalent bond between the tetrahydrofuran carbonyl and the active site catalytic cysteine residue (Witherington, J., 1999). Additionally, the same cyclic ketone compounds are described in WO-A-9953039 as part of a wide-ranging description of inhibitors of cysteine proteases associated with parasitic diseases, with particular reference to the treatment of malaria by inhibition of falcipain. However, subsequent literature describes the cyclic ketone compounds of WO-A-9850533 to be unsuitable for further development or for full pharmacokinetic evaluation due to a physiochemical property of the inhibitors, the poor chiral stability of the α-aminoketone chiral centre (Marquis, R. W. et al, *J. Med. Chem.*, 44(5), 725–736, 2001). WO-A-0069855 describes compounds that may also be referred to as cyclic ketones with particular reference towards inhibition of cathepsin S. The compounds of WO-A-0069855 are considered to be an advance on compounds of WO-A-9850533 due to the presence of the β-substituent on the cyclic ketone ring system that provides increased chiral stability to the α-carbon of the cyclic ketone ring system. In an attempt to solve the problem of poor chiral integrity, subsequent literature has provided a closely related cyclic ketone series to that described in WO-A-9850533, where an approximately 300-fold loss in inhibitor potency was observed upon introduction of an alkyl group in place of the labile α-proton (Marquis, R. W. et al, *J. Med. Chem.*, 44, 1380–1395, 2001). Additionally, subsequent literature has shown that within the cyclic ketone series described in WO-A-9850533, the α-(S) isomer is approximately 10 to 80-fold more potent than the α-(R) isomer (Fenwick, A. E. et al, *Bioorg. Med. Chem. Lett.*, 11, 199–202, 2001).

It has now been discovered that certain compounds, defined by general formula (I), are potent and selective cruzipain protease inhibitors which are useful in the treatment of *Trypanosoma cruzi* infection. Other compounds defined by general formula (I) are protease inhibitors across a broad range of CA C1 cysteine proteases and compounds useful in the treatment of diseases caused by cysteine proteases. Compounds described by general formula (I) contain an α-alkyl group, of the R-stereo-configuration (or the S-stereo-configuration when Z='S'), yet surprisingly compounds defined by general formula (I) retain good potency. The present invention provides substituted (3aR, 6aR) N-(3-oxo-hexahydrocyclopenta[b]furan-3a-yl) alkylamide, (3aS,6aR) N-(3-oxo-hexahydrocyclopenta[b]thiophene-3a-yl)alkylamide, (3aR,6aS) N-(3-oxo-hexahydropentalen-3a-yl)alkylamide or (3aR,6aR) N-(3-oxo-hexahydrocyclo penta[b]pyrrol-3a-yl)alkylamide compounds defined by general formula (I).

Accordingly, the first aspect of the invention provides a compound according to general formula (I):

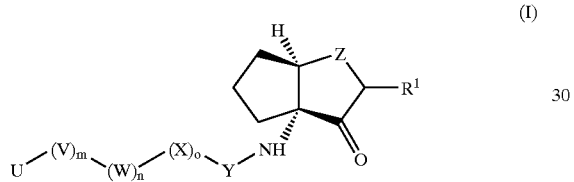

(I)

wherein: $R^1 = C_{0-7}$-alkyl (when C=0, $R^1$ is simply hydrogen), $C_{3-6}$-cycloalkyl or —Ar—$C_{0-7}$-alkyl (when C=0, $R^1$ is simply an aromatic moiety Ar);

Z=O, S, $CR^2R^3$ or $NR^4$, where $R^4$ is chosen from $C_{0-7}$-alkyl, $C_{3-6}$-cycloalkyl or Ar—$C_{0-7}$-alkyl;

Each of $R^2$ and $R^3$ is independently chosen from $C_{0-7}$-alkyl, $C_{3-6}$-cycloalkyl, Ar—$C_{0-7}$-alkyl, O—$C_{0-7}$-alkyl, O—$C_{3-6}$-cycloalkyl, O—Ar—$C_{0-7}$-alkyl S—$C_{0-7}$-alkyl, S—$C_{3-6}$-cycloalkyl, S—Ar—$C_{0-7}$-alkyl, NH—$C_{0-7}$-alkyl, NH—$C_{3-6}$-cycloalkyl, NH—Ar—$C_{0-7}$-alkyl, N($C_{0-7}$-alkyl)$_2$, N($C_{3-6}$-cycloalkyl)$_2$ or N(Ar—$C_{0-7}$-alkyl)$_2$;

Y=$CR^5R^6$—CO, where $R^5$, $R^6$ are chosen from $C_{0-7}$-alkyl, $C_{3-6}$-cycloalkyl or Ar—$C_{0-7}$-alkyl;

(X)$_o$=$CR^7R^8$, where $R^7$ and $R^8$ are independently chosen from $C_{0-7}$-alkyl, $C_{3-6}$-cycloalkyl and Ar—$C_{0-7}$-alkyl and o is a number from zero to three;

(W)$_n$=O, S, C(O), S(O) or S(O)$_2$ or $NR^9$, where $R^9$ is chosen from $C_{0-7}$-alkyl, $C_{3-6}$-cycloalkyl and Ar—$C_{0-7}$-alkyl and n is zero or one;

(V)$_m$=C(O), C(S), S(O), S(O)$_2$, S(O)$_2$NH, OC(O), NHC(O), NHS(O), NHS(O)$_2$, OC(O)NH, C(O)NH or $CR^{10}R^{11}$, where $R^{10}$ and $R^{11}$ are independently chosen from $C_{0-7}$-alkyl, $C_{3-6}$-cycloalkyl, Ar—$C_{0-7}$-alkyl and m is a number from zero to three, provided that when m is greater than one, (V)$_m$ contains a maximum of one carbonyl or sulphonyl group;

U=a stable 5- to 7-membered monocyclic or a stable 8- to 11-membered bicyclic ring which is either saturated or unsaturated and which includes zero to four heteroatoms (as detailed below):

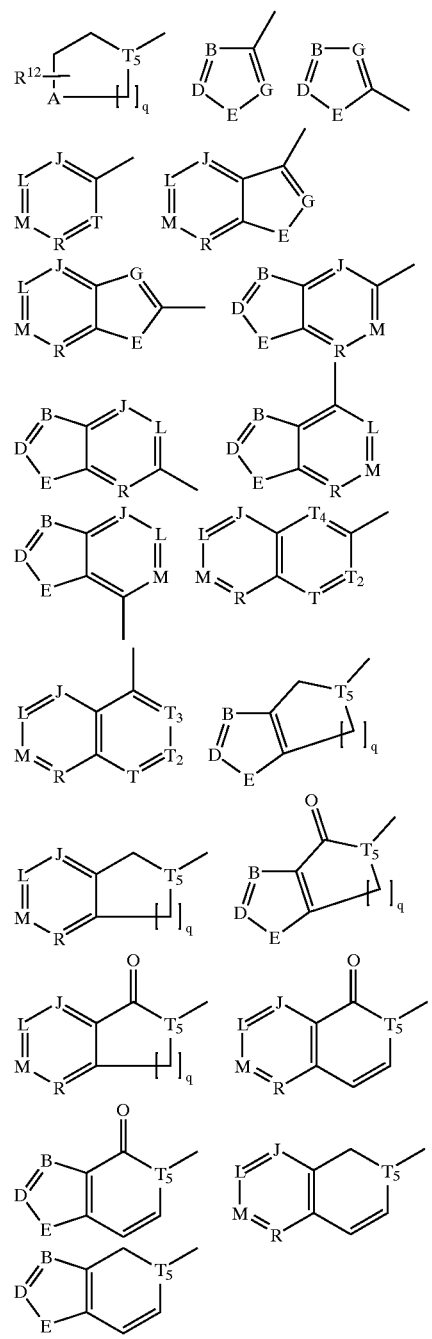

wherein $R^{12}$ is:

$C_{0-7}$-alkyl, $C_{3-6}$-cycloalkyl, Ar—$C_{0-7}$-alkyl, O—$C_{0-7}$-alkyl, O—$C_{3-6}$-cycloalkyl, O—Ar—$C_{0-7}$-alkyl, S—$C_{0-7}$-alkyl, S—$C_{3-6}$-cycloalkyl, S—Ar—$C_{0-7}$-alkyl, NH—$C_{0-7}$-alkyl, NH—$C_{3-6}$-cycloalkyl, NH—Ar—$C_{0-7}$-alkyl, N($C_{0-7}$-alkyl)$_2$, N($C_{3-6}$-cycloalkyl)$_2$ or N(Ar—$C_{0-7}$-alkyl)$_2$ or, when it is part of the group $CHR^{12}$ or $CR^{12}$, $R^{12}$ may be halogen;

A is chosen from:

$CH_2$, $CHR^{12}$, O, S and $NR^{13}$;

wherein $R^{12}$ is as defined above and $R^{13}$ is chosen from:

$C_{0-7}$-alkyl, $C_{3-6}$-cycloalkyl and Ar—$C_{0-7}$-alkyl;

B, D and G are independently chosen from:

$CR^{12}$, where $R^{12}$ is as defined above, or N;

E is chosen from:
- $CH_2$, $CHR^{12}$, O, S and $NR^{13}$, where $R^{12}$ and $R^{13}$ are defined as above;

J, L, M, R, T, $T_2$, $T_3$ and $T_4$ are independently chosen from:
- $CR^{12}$ and N, where $R^{12}$ is as defined above;

$T_5$ is chosen from:
- CH or N;

q is a number from one to three, thereby defining a 5-, 6- or 7-membered ring.

B, D, G, J, L, M, R, T, $T_2$, $T_3$ and $T_4$ may additionally represent an N-oxide (N→O).

The present invention includes all salts, hydrates, solvates, complexes and prodrugs of the compounds of this invention. The term "compound" is intended to include all such salts, hydrates, solvates, complexes and prodrugs, unless the context requires otherwise.

Appropriate pharmaceutically and veterinarily acceptable salts of the compounds of general formula (I) include salts of organic acids, especially carboxylic acids, including but not limited to acetate, trifluoroacetate, lactate, gluconate, citrate, tartrate, maleate, malate, pantothenate, adipate, alginate, aspartate, benzoate, butyrate, digluconate, cyclopentanate, glucoheptanate, glycerophosphate, oxalate, heptanoate, hexanoate, fumarate, nicotinate, palmoate, pectinate, 3-phenylpropionate, picrate, pivalate, proprionate, tartrate, lactobionate, pivolate, camphorate, undecanoate and succinate, organic sulphonic acids such as methanesulphonate, ethanesulphonate, 2-hydroxyethane sulphonate, camphorsulphonate, 2-naphthalenesulphonate, benzenesulphonate, p-chlorobenzenesulphonate and p-toluenesulphonate; and inorganic acids such as hydrochloride, hydrobromide, hydroiodide, sulphate, bisulphate, hemisulphate, thiocyanate, persulphate, phosphoric and sulphonic acids. Salts which are not pharmaceutically or veterinarily acceptable may still be valuable as intermediates.

Prodrugs are any covalently bonded compounds which release the active parent drug according to general formula (I) in vivo. A prodrug may for example constitute ketal or hemiketal derivative of the exocyclc ketone functionality present in the (3aR,6aR) N-(3-oxo-hexahydrocyclopenta[b]furan-3a-yl)alkylamide, (3aS,6aR) N-(3-oxo-hexahydrocyclopenta[b]thiophen-3a-yl)alkylamide, (3aR, 6aS) N-(3-oxo-hexahydropentalen-3a-yl)alkylamide or (3aR, 6aR) N-(3-oxo-hexahydrocyclo penta[b]pyrrol-3a-yl) alkylamide scaffold. If a chiral centre or another form of isomeric centre is present in a compound of the present invention, all forms of such isomer or isomers, including-enantiomers and diastereoisomers, are intended to be covered herein. Compounds of the invention containing a chiral centre may be used as a racemic mixture, an enantiomerically enriched mixture, or the racemic mixture may be separated using well-known techniques and an individual enantiomer may be used alone.

'Halogen' as applied herein is meant to include F, Cl, Br, I;

'Heteroatom' as applied herein is meant to include O, S and N;

'$C_{0-7}$-alkyl' as applied herein is meant to include stable straight and branched chain aliphatic carbon chains containing zero (i.e. simply hydrogen) to seven carbon atoms such as methyl, ethyl, n-propyl, isopropyl, n-butyl, isobutyl, t-butyl, pentyl, isopentyl, hexyl, heptyl and any simple isomers thereof. Additionally, any $C_{0-7}$-alkyl may optionally be substituted at any point by one, two or three halogen atoms (as defined above) for example to give a trifluoromethyl substituent. Furthermore, $C_{0-7}$-alkyl may contain one or more heteroatoms (as defined above) for example to give ethers, thioethers, sulphones, sulphonamides, substituted amines, amidines, guanidines, carboxylic acids, carboxamides. If the heteroatom is located at a chain terminus then it is appropriately substituted with one or two hydrogen atoms. A heteroatom or halogen is only present when $C_{0-7}$-alkyl contains a minimum of one carbon atom.

$C_{1-7}$-alkyl as applied herein is meant to include the definitions for $C_{0-7}$-alkyl (as defined above) but describes a substituent that comprises a minimum of one carbon.

'$C_{3-6}$-cycloalkyl' as applied herein is meant to include any variation of '$C_{0-7}$-alkyl' which additionally contains a carbocyclic ring such as cyclopropyl, cyclobutyl, cyclopentyl, cyclohexyl. The carbocyclic ring may optionally be substituted with one or more halogens (as defined above) or heteroatoms (as defined above) for example to give a tetrahydrofuran, pyrrolidine, piperidine, piperazine or morpholine substituent.

'Ar—$C_{0-7}$-alkyl' as applied herein is meant to include any variation of $C_{0-7}$-alkyl which additionally contains an aromatic ring moiety 'Ar'. The aromatic ring moiety Ar can be a stable 5 or 6-membered monocyclic or a stable 9 or 10 membered bicyclic ring which is unsaturated, as defined previously for U in general formula (I). The aromatic ring moiety Ar may be substituted by $R^{12}$ (as defined above for U in general formula (I)). When C=0 in the substituent Ar—$C_{0-7}$-alkyl, the substituent is simply the aromatic ring moiety Ar.

Other expressions containing terms such as alkyl and cycloalkyl are intended to be construed according to the definitions above. For example "$C_{1-4}$ alkyl" is the same as $C_{0-7}$-alkyl except that it contains from one to four carbon atoms.

If different structural isomers are present, and/or one or more chiral centres are present, all isomeric forms are intended to be covered. Enantiomers are characterised by the absolute configuration of their chiral centres and described by the R- and S-sequencing rules of Cahn, Ingold and Prelog. Such conventions are well known in the art (e.g. see 'Advanced Organic Chemistry', $3^{rd}$ edition, ed. March, J., John Wiley and Sons, New York, 1985).

Preferred compounds of general formula (I) include, but are not limited to, those in which, independently or in combination:

Z is O, S, NH or $CH_2$.

Additionally, preferred compounds of general formula (I) include, but are not limited to, those in which, independently or in combination Z is $NR^4$, where $R^4$ is Ar—$C_{1-4}$-alkyl or a substituted carbonyl or sulphonyl group Thus, examples of preferred compounds include those containing a (3aR, 6aR) N-(3-oxo-hexahydrocyclopenta[b]furan-3a-yl)alkylamide, (3aS,6aR) N-(3-oxo-hexahydrocyclopenta[b]thiophen-3a-yl)alkylamide, (3aR, 6aS) N-(3-oxo-hexahydropentalen-3a-yl)alkylamide or a (3aR,6aR) N-(3-oxo-hexahydrocyclopenta[b]pyrrol-3a-yl) alkylamide bicyclic moiety as shown below.

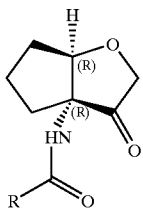

(3aR, 6aR)-N-(3-Oxo-hexahydrocyclopenta[b]furan-3a-yl)alkylamide

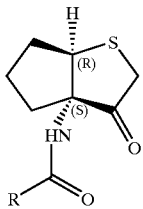

(3aS, 6aR)-N-(3-Oxo-hexahydrocyclopenta[b]thiophen-3a-yl)alkylamide

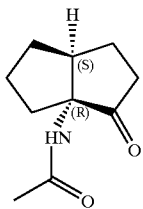

(3aR, 6aS)-N-(3-Oxo-hexahydropentalen-3a-yl)alkylamide

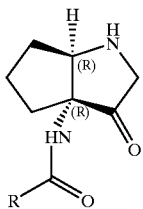

(3aR, 6aR)-N-(3-Oxo-hexahydrocyclopenta[b]pyrrol-3a-yl)alkylamide

In compounds of general formula (I), it is preferred that $R^1$ comprises $C_{0-7}$-alkyl or Ar—$C_{0-7}$-alkyl. Thus, for example, preferred $R^1$ moieties include hydrogen, or a straight or branched alkyl chain, or a straight or branched heteroalkyl chain, or an optionally substituted arylalkyl chain, or an optionally substituted arylheteroalkyl chain.

It is particularly preferred that $R^1$ is hydrogen or $C_{1-4}$ alkyl or Ar—$C_{1-4}$-alkyl and examples of such $R^1$ substituents include, but are not limited to:

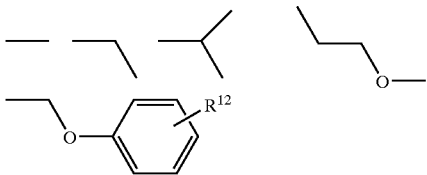

where $R^{12}$ is defined above.

In preferred compounds of general formula (I), Y is $CHR^6CO$ where $R^6$ is selected from $C_{0-7}$-alkyl or Ar—$C_{0-7}$-alkyl, for example hydrogen, a straight or branched alkyl chain, a straight or branched heteroalkyl chain, an optionally substituted arylalkyl chain or an optionally substituted aryl-heteroalkyl chain. Additionally, in preferred compounds of general formula (I), $R^6$ is selected from $C_{3-6}$-cycloalkyl, for example cyclohexylmethyl.

Examples of preferred Y substituents include the following:

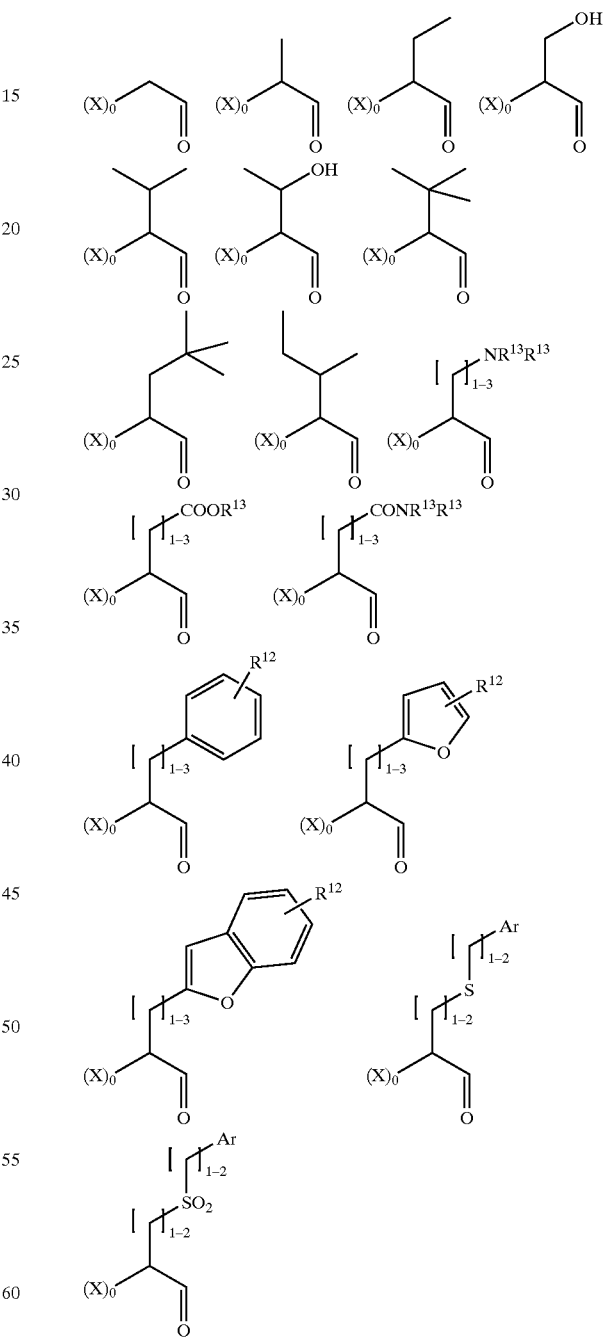

wherein $R^{12}$, $R^{13}$ and Ar are as defined above.

More preferred $R^6$ groups include $C_{1-4}$-alkyl, which may be substituted with OH, $NR^{13}R^{13}$, $COOR^{13}$, or $CONR^{13}$ or cycloalkylmethyl or Ar—$C_{1-4}$-alkyl, where the aryl group may be substituted with $R^{12}$; wherein each $R^{12}$ and $R^{13}$ is independently as defined above.

Even more preferred $R^6$ groups comprise Ar—CH$_2$—, where the aromatic ring is an optionally substituted phenyl or monocyclic heterocycle. Additionally, even more preferred $R^6$ groups comprise simple branched alkyl groups such as isobutyl or straight heteroalkyl chains such as benzysulfanylmethyl or benzylsulphonylmethyl. Furthermore, even more preferred $R^6$ groups comprise cyclohexylmethyl. Examples of even more preferred Y substituents comprise the following,

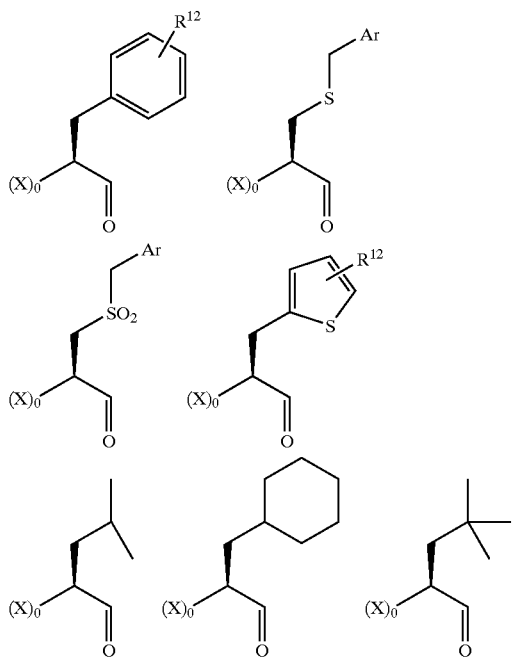

wherein $R^{12}$ and Ar are as defined previously

It is preferred that in the group $(X)_o$, each of $R^7$ and $R^8$ is selected from $C_{0-7}$-alkyl or Ar—$C_{0-7}$-alkyl, for example hydrogen, a straight or branched alkyl chain, a straight or branched heteroalkyl chain, an optionally substituted arylalkyl chain or an optionally substituted arylheteroalkyl chain.

More preferred $(X)_o$ groups comprise $R^7$ chosen from hydrogen; $R^8$ is $C_{1-4}$-alkyl, which may be substituted with OH, $NR^{13}R^{13}$, $COOR^{13}$, or $CONR^{13}$; or Ar—$C_{1-4}$-alkyl, where the aryl group may be substituted with $R^{12}$, wherein each $R^{12}$ and $R^{13}$ is independently as defined above.

Examples of preferred $(X)_o$ groups include the following:

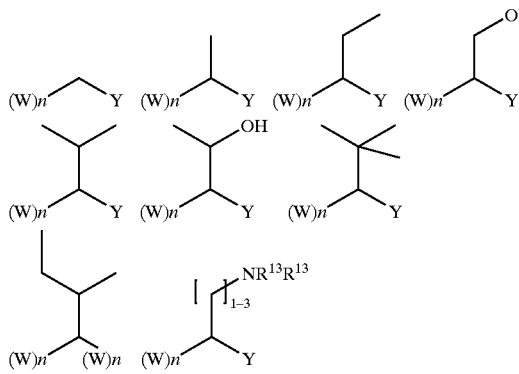

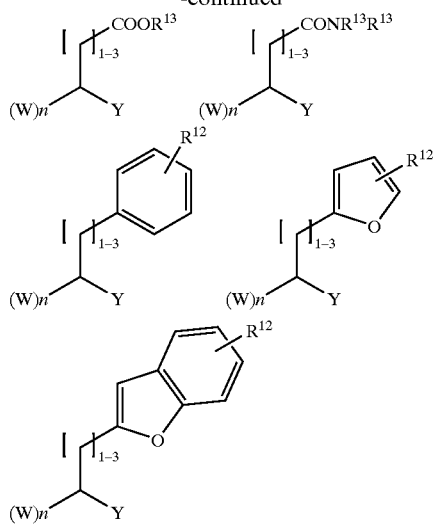

wherein $R^{12}$ and $R^{13}$ are as defined previously.

Even more preferred compounds of general formula (I), comprise $(X)_o$ groups that are simple alkyl groups such as methylene and where o=0 or 1.

In the group $(W)_n$, W is preferably O, S, SO$_2$, S(O), C(O) or NR$^9$, where $R^9$ is $C_{0-4}$-alkyl; and n is 0 or 1.

More preferred compounds of general formula (I), comprise $(W)_n$ groups defined as O, S, SO$_2$, C(O) and NH where n=0 or 1.

Yet even more preferred compounds of general formula (I), comprise $(W)_n$ groups defined as NH where n=1.

In the group $(V)_m$:

V is preferably C(O), C(O)NH or CHR$^{11}$, where $R^{11}$ is $C_{0-4}$-alkyl; and m is 0 or 1.

Preferred V and W substituent combinations encompassed by general formula (I) include, but are not limited to:

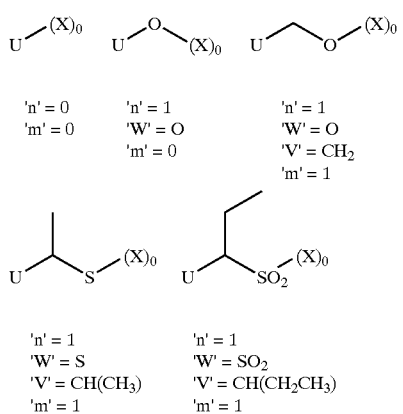

-continued

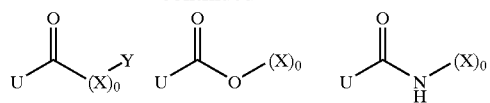

| 'n' = 0 | 'n' = 1 | (X) > 0 |
| 'V' = C(O) | 'W' = O | 'n' = 1 |
| 'm' = 1 | 'V' = C(O) | 'W' = NR$^9$ |
| | 'm' = 1 | R$^9$ = H |
| | | 'V' = C(O) |
| | | 'm' = 1 |

Additionally, a preferred V and W substituent combination encompassed by general formula (I) includes, but is not limited to:

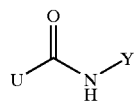

'(X)$_o$' = '-'
n = 1
'W' = NR$^9$, R$^9$ = 'H'
'V' = C(O)
m = 1

More preferred V, W and X substituent combinations encompassed by general formula (I) comprise, but are not limited to

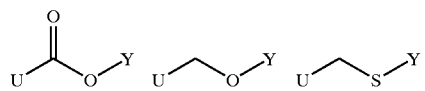

| (X)$_0$ = '-' | (X)$_0$ = '-' | (X)$_0$ = '-' |
| (W)$_n$ = 'O' | (W)$_n$ = 'O' | (W)$_n$ = 'S' |
| (V)$_m$ = 'C(O)' | (V)$_m$ = 'CH$_2$' | (V)$_m$ = 'CH$_2$' |

| (X)$_0$ = '-' | (X)$_0$ = 'CH$_2$' | (X)$_0$ = '-' |
| (W)$_n$ = 'SO$_2$' | (W)$_n$ = 'C(O)' | (W)$_n$ = 'NH' |
| (V)$_m$ = 'CH$_2$' | (V)$_m$ = '-' | (V)$_m$ = 'C(O)' |

In preferred compounds of general formula (I), U comprises an optionally substituted 5- or 6-membered saturated or unsaturated heterocycle or Ar group or an optionally substituted saturated or unsaturated 9- or 10-membered heterocycle or Ar group. Examples of such preferred U rings include the following:

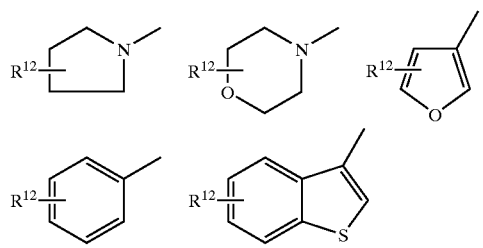

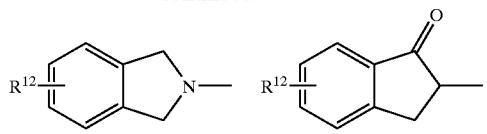

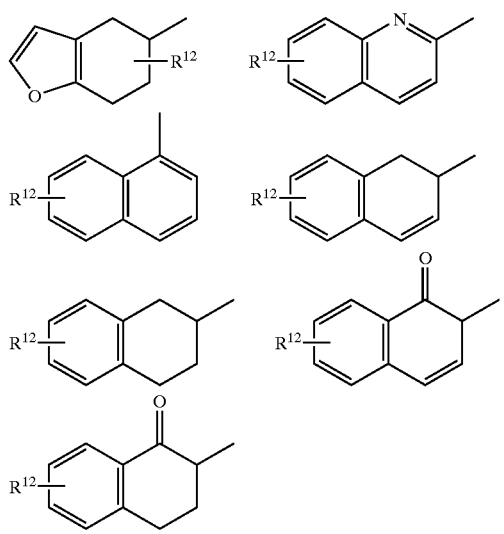

and also the following wherein R$^{12}$ is as defined previously.

More preferred compounds of general formula (I), contain a U group comprising of a bulky alkyl or aryl group at the para position of an aryl Ar. Also, more preferred compounds contain a meta or para-biaryl Ar—Ar, where Ar is as previously defined. Additionally, more preferred compounds contain a 6,6 or 6,5 or 5,6-fused aromatic ring. Examples of more preferred U groups are

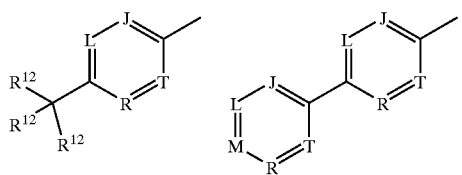

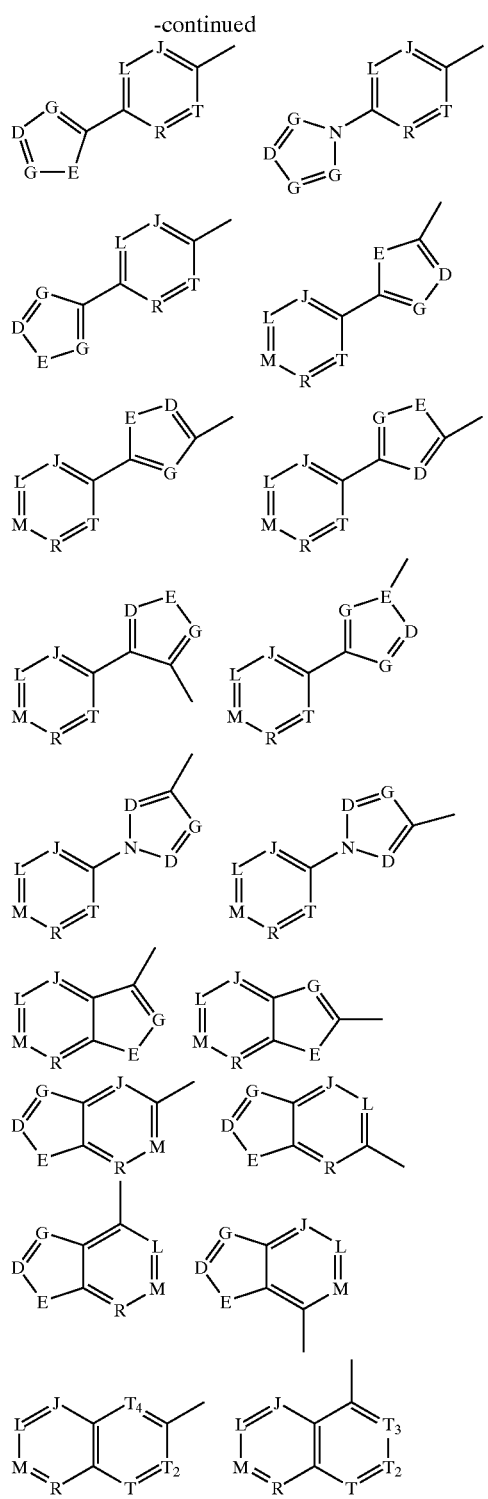

wherein $R^{12}$, D, E, G, J, L, M, R, T, $T_2$, $T_3$ and $T_4$ are as defined previously.

Even more preferred compounds of general formula (I), particularly for inhibition of cruzipain, contain a U group comprising a 6-membered Ar ring containing a bulky alkyl or aryl group at the para position, where Ar is as previously defined

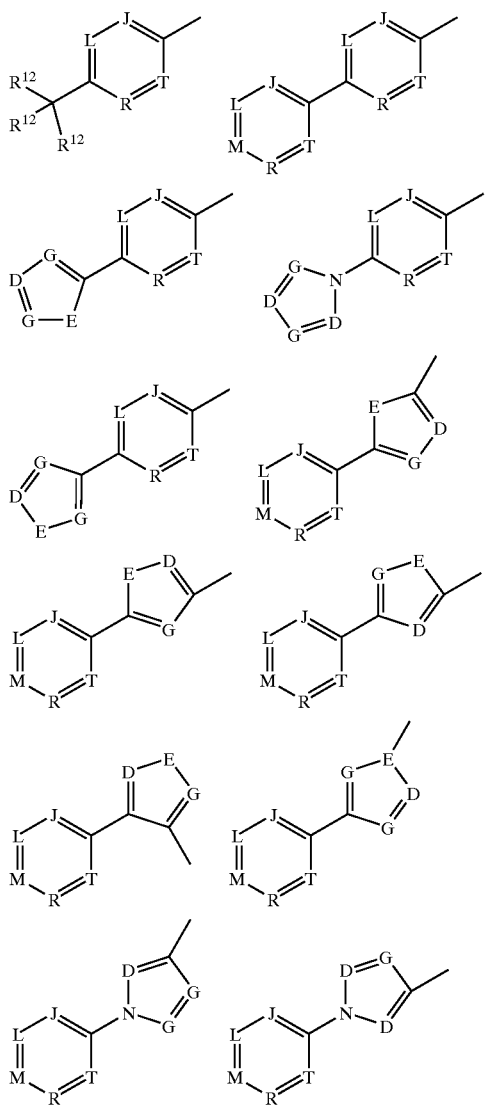

wherein $R^{12}$, D, E, G, J, L, M, R and T are as defined previously

Yet even more preferred compounds of general formula (I), contain a U group comprising but are not limited to the following,

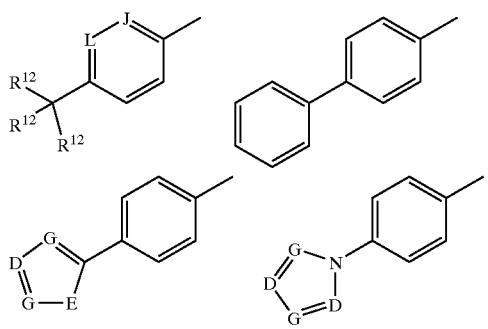

-continued

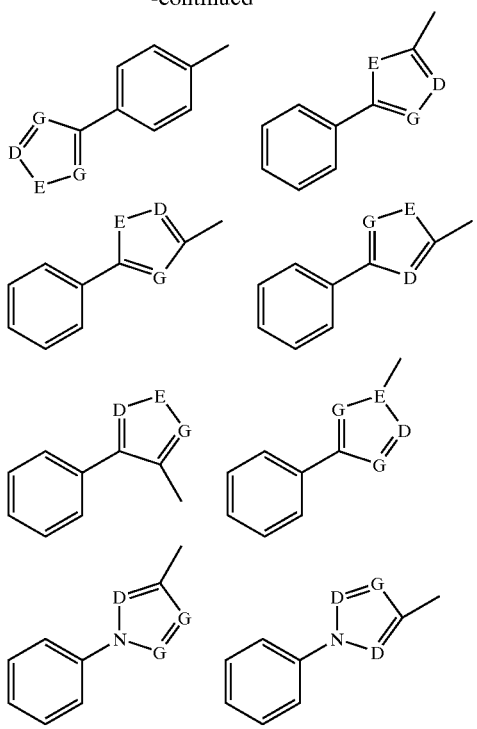

wherein $R^{12}$, D, E, G, J and L are as defined previously.

Abbreviations and symbols commonly used in the peptide and chemical arts are used herein to describe compounds of the present invention, following the general guidelines presented by the IUPAC-IUB Joint Commission on Biochemical Nomenclature as described in *Eur. J. Biochem.*, 158, 9-, 1984. Compounds of formula (I) and the intermediates and staring materials used in their preparation are named in accordance with the IUPAC rules of nomenclature in which the characteristic groups have decreasing priority for citation as the principle group. An example compound of formula (I), compound (1) in which $R^1$ is H, Z is oxygen, Y is 4-methylpentyl, $(X)_0$ is zero, $(W)_n$ is oxygen, $(V)_m$ is methylene and U is phenyl is thus named:

(1)

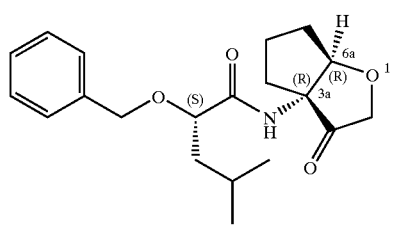

(3aR, 6aR) 2-Benzyloxy-4-methyl-pentanoic acid (3-oxo-hexahydrocyclopenta[b]furan-3a-yl)-amide A second example compound of formula (I), compound (2) in which $R^1$ is H, Z is sulphur, Y is 4-methylpentyl, $(X)_0$ is zero, $(W)_n$ is oxygen, $(V)_m$ is methylene and U is phenyl is thus named:

(2)

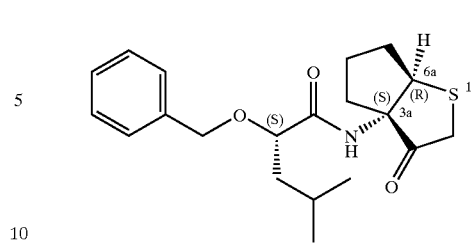

(3aS, 6aR) 2-Benzyloxy-4-methyl-pentanoic acid (3-oxo-hexahydrocyclopenta[b]thiophen-3a-yl)-amide A third example compound of formula (I), compound (3) in which $R^1$ is H, Z is methylene, Y is 4-methylpentyl, $(X)_0$ is zero, $(W)_n$ is oxygen, $(V)_m$ is methylene and U is phenyl is thus named:

(3)

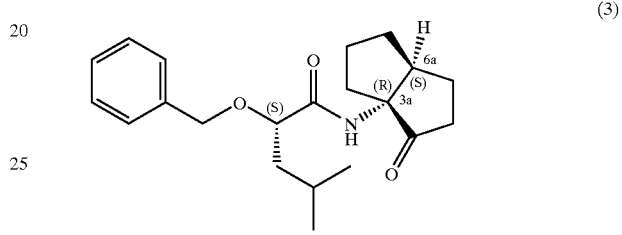

(3aR, 6aS) 2-Benzyloxy-4-methyl-pentanoic acid (3-oxo-hexahydro-pentalen-3a-yl)-amide A fourth example compound of formula (I), compound (4) in which $R^1$ is H, Z is NH, Y is 4-methylpentyl, $(X)_0$ is zero, $(W)_n$ is oxygen, $(V)_m$ is methylene and U is phenyl is thus named:

(4)

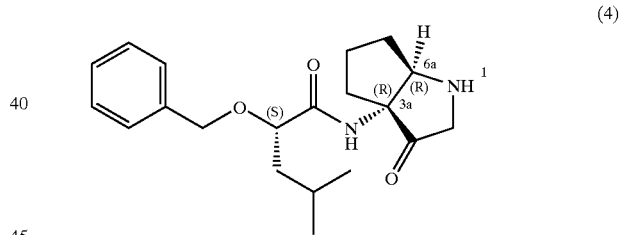

(3aR, 6aR) 2-Benzyloxy-4-methyl-pentanoic acid (3-oxo-hexahydrocyclopenta[b]pyrrol-3a-yl)-amide Compounds of the invention include, but are not limited to, the following examples that are the (3aR, 6aR) isomer of general formula (I) where Z='O' and $R^1$='H', and also include the equivalent analogues included in the full definition of Z and $R^1$ 4-tert-Butyl-N-[2-(4-hydroxyphenyl)-1-(3-oxo-hexahydrocyclopenta[b]furan-3a-ylcarbamoyl)-ethyl]-benzamide N-[2-(4-Hydroxyphenyl)-1-(3-oxo-hexahydrocyclopenta[b]furan-3a-ylcarbamoyl)-ethyl]-4-trifluoromethoxy-benzamide 4-Dimethylamino-N-[2-(4-hydroxyphenyl)-1-(3-oxo-hexahydrocyclopenta[b]furan-3a-ylcarbamoyl)-ethyl]-benzamide N-[2-(4-Hydroxyphenyl)-1-(3-oxo-hexahydrocyclopenta[b]furan-3a-ylcarbamoyl) ethyl]-4-isopropyl-benzamide 4-Difluoromethoxy-N-[2-(4-Hydroxyphenyl)-1-(3-oxo-hexahydrocyclopenta[b]furan-3a-ylcarbamoyl)-ethyl]-benzamide N-[2-(4-Hydroxyphenyl)-1-(3-oxo-hexahydrocyclopenta[b]furan-3a-ylcarbamoyl)-ethyl]-4-trifluoromethyl-benzamide Naphthalene-2-carboxylic acid [2-(4-hydroxyphenyl)-1-(3-oxo-hexahydrocyclopenta[b]furan-3a-ylcarbamoyl)-ethyl]-amide Naphthalene-1-carboxylic acid [2-(4-hydroxyphenyl)-1-(3-oxo-hexahydrocyclopenta[b]furan-3a-ylcarbamoyl)-ethyl]-amide Quinoline-6-carboxylic acid [2-(4-hydroxyphenyl)-1-(3-oxo-hexahydrocyclopenta[b]furan-3a-ylcarbamoyl)-ethyl]-amide Benzo[b]thiophene-2-carboxylic acid [2-(4-hydroxyphenyl)-1-(3-oxo-hexahydro-cyclopenta[b]furan-3a-ylcarbamoyl)-ethyl]-amide Benzo[b]thiophene-3-carboxylic acid [2-(4-hydroxyphenyl)-1-(3-oxo-hexahydro-cyclopenta[b]furan-3a-ylcarbamoyl)-ethyl]-amide Benzothiazole-5-carboxylic acid [2-(4-hydroxyphenyl)-1-(3-oxo-hexahydro-cyclopenta[b]furan-3a-ylcarbamoyl)-ethyl]-amide Biphenyl-4-carboxylic acid [2-(4-hydroxyphenyl)-1-(3-oxo-hexahydro-cyclopenta[b]furan-3a-ylcarbamoyl)-ethyl]-amide N-[2-(4-Hydroxyphenyl)-1-(3-oxo-hexahydrocyclopenta[b]furan-3a-ylcarbamoyl)-ethyl]-4-imidazol-1-yl-benzamide N-[2-(4-Hydroxyphenyl)-1-(3-oxo-hexahydrocyclopenta[b]furan-3a-ylcarbamoyl)-ethyl]-4-thiophen-2-ylbenzamide N-[2-(4-Hydroxyphenyl)-1-(3-oxo-hexahydrocyclopenta[b]furan-3a-ylcarbamoyl)-ethyl]-5-thiophen-2-ylnicotinamide 2-Phenylthiazole-4-carboxylic acid [2-(4-hydroxyphenyl)-1-(3-oxo-hexahydro-cyclopenta[b]furan-3a-ylcarbamoyl)-ethyl]-amide 2-Pyridin-3-ylthiazole-4-carboxylic acid [2-(4-hydroxyphenyl)-1-(3-oxo-hexahydro-cyclopenta[b]furan-3a-ylcarbamoyl)-ethyl]-amide 4-Phenylthiophene-2-carboxylic acid [2-(4-hydroxyphenyl)-1-(3-oxo-hexahydro-cyclopenta[b]furan-3a-ylcarbamoyl)-ethyl]-amide 2-Thiophen-2-ylthiazole-4-carboxylic acid [2-4-hydroxyphenyl)-1-(3-oxo-hexahydro-cyclopenta[b]furan-3a-ylcarbamoyl)-ethyl]-amide 3-Phenylpyrrole-1-carboxylic acid [2-(4-hydroxyphenyl)-1-(3-oxo-hexahydrocyclopenta[b]furan-3a-ylcarbamoyl)-ethyl]-amide 4-tert-Butyl-N-[3-methyl-1-(3-oxo-hexahydrocyclopenta[b]furan-3a-ylcarbamoyl)-butyl]-benzamide N-[3-Methyl-1-(3-oxo-hexahydrocyclopenta[b]furan-3a-ylcarbamoyl)-butyl]-4-trifluoromethoxy-benzamide 4-Dimethylamino-N-[3-methyl-1-(3-oxo-hexahydrocyclopenta[b]furan-3a-ylcarbamoyl)-butyl]-benzamide 4-Isopropyl-N-[3-methyl-1-(3-oxo-hexahydrocyclopenta[b]furan-3a-ylcarbamoyl)-butyl]-benzamide 4-Difluoromethoxy-N-[3-methyl-1-(3-oxo-hexahydrocyclopenta[b]furan-3a-ylcarbamoyl)-butyl]-benzamide N-[3-Methyl-1-(3-oxo-hexahydrocyclopenta[b]furan-3a-ylcarbamoyl)-butyl]-4-trifluoromethyl-benzamide Naphthalene-2-carboxylic acid [3-methyl-1-(3-oxo-hexahydro-cyclopenta[b]furan-3a-ylcarbamoyl)-butyl]-amide Naphthalene-1-carboxylic acid [3-methyl-1-(3-oxo-hexahydro-cyclopenta[b]furan-3a-ylcarbamoyl)-butyl]-amide Quinoline-6-carboxylic acid [3-methyl-1-(3-oxo-hexahydro-cyclopenta[b]furan-3a-ylcarbamoyl)-butyl]-amide Benzo[b]thiophene-2-carboxylic acid [3-methyl-1-(3-oxo-hexahydro-cyclopenta[b]furan-3a-ylcarbamoyl)-butyl]-amide Benzo[b]thiophene-3-carboxylic acid [3-methyl-1-(3-oxo-hexahydro-cyclopenta[b]furan-3a-ylcarbamoyl)-butyl]-amide Benzothiazole-5-carboxylic acid [3-methyl-1-(3-oxo-hexahydro-cyclopenta[b]furan-3a-ylcarbamoyl)-butyl]-amide Biphenyl-4-carboxylic acid [3-methyl-1-(3-oxo-hexahydro-cyclopenta[b]furan-3a-ylcarbamoyl)-butyl]-amide N-[3-Methyl-1-(3-oxo-hexahydrocyclopenta[b]furan-3a-ylcarbamoyl)-butyl]-4-imidazol-1-ylbenzamide N-[3-Methyl-1-(3-oxo-hexahydrocyclopenta[b]furan-3a-ylcarbamoyl)-butyl]-4-thiophen-2-ylbenzamide N-[3-Methyl-1-(3-oxo-hexahydrocyclopenta[b]furan-3a-ylcarbamoyl)-butyl]-5-thiophen-2-ylnicotinamide 2-Phenylthiazole-4-carboxylic acid [3-methyl-1-(3-oxo-hexahydro-cyclopenta[b]furan-3a-ylcarbamoyl)-butyl]-amide 2-Pyridin-3-ylthiazole-4-carboxylic acid [3-methyl-1-(3-oxo-hexahydro-cyclopenta[b]furan-3a-ylcarbamoyl)-butyl]-amide 4-Phenylthiophene-2-carboxylic acid [3-methyl-1-(3-oxo-hexahydro-cyclopenta[b]furan-3a-ylcarbamoyl)-butyl]-amide 2-Thiophen-2-ylthiazole-4-carboxylic acid [3-methyl-1-(3-oxo-hexahydro-cyclopenta[b]furan-3a-ylcarbamoyl)-butyl]-amide 3-Phenylpyrrole-1-carboxylic acid [3-methyl-1-(3-oxo-hexahydro-cyclopenta[b]furan-3a-ylcarbamoyl)-butyl]-amide 4-tert-Butyl-N-[2-3-hydroxyphenyl)-1-(3-oxo-hexahydrocyclopenta[b]furan-3a-ylcarbamoyl)-ethyl]-benzamide N-[2-(3-Hydroxyphenyl)-1-(3-oxo-hexahydrocyclopenta[b]furan-3a-ylcarbamoyl)-ethyl]-4-trifluoromethoxy-benzamide 4-Dimethylamino-N-[2-(3-hydroxyphenyl)-1-(3-oxo-hexahydrocyclopenta[b]furan-3a-ylcarbamoyl)-ethyl]-benzamide N-[2-(3-Hydroxyphenyl)-1-(3-oxo-hexahydrocyclopenta[b]furan-3a-ylcarbamoyl)ethyl]-4-isopropyl-benzamide 4-Difluoromethoxy-N-[2-(3-hydroxyphenyl)-1-(3-oxo-hexahydrocyclopenta[b]furan-3a-ylcarbamoyl)-ethyl]-benzamide N-[2-(3-Hydroxyphenyl)-1-(3-oxo-hexahydrocyclopenta[b]furan-3a-ylcarbamoyl)-ethyl]-4-trifluoromethyl-benzamide Naphthalene-2-carboxylic acid [2-(3-hydroxyphenyl)-1-(3-oxo-hexahydro-cyclopenta[b]furan-3a-ylcarbamoyl)-ethyl]-amide Naphthalene-1-carboxylic acid [2-(3-hydroxyphenyl)-1-(3-oxo-hexahydro-cyclopenta[b]furan-3a-ylcarbamoyl)-ethyl]-amide Quinoline-6-carboxylic acid [2-(3-hydroxyphenyl)-1-(3-oxo-hexahydro-cyclopenta[b]furan-3a-ylcarbamoyl)-ethyl]-amide Benzo[b]thiophene-2-carboxylic acid [2-(3-hydroxyphenyl)-1-(3-oxo-hexahydro-cyclopenta[b]furan-3a-ylcarbamoyl)-ethyl]-amide Benzo[b]thiophene-3-carboxylic acid [2-(3-hydroxyphenyl)-1-(3-oxo-hexahydro-cyclopenta[b]furan-3a-ylcarbamoyl)-ethyl]-amide Benzothiazole-5-carboxylic acid [2-(3-hydroxyphenyl)-1-(3-oxo-hexahydro-cyclopenta[b]furan-3a-ylcarbamoyl)-ethyl]-amide Biphenyl-4-carboxylic acid [2-(3-hydroxyphenyl)-1-(3-oxo-hexahydro-cyclopenta[b]furan-3a-ylcarbamoyl)-ethyl]-amide N-[2-(3-Hydroxyphenyl)-1-(3-oxo-hexahydrocyclopenta[b]furan-3a-ylcarbamoyl)-ethyl]-4-imidazol-1-yl-benzamide N-[2-(3-Hydroxyphenyl)-1-(3-oxo-hexahydrocyclopenta[b]furan-3a-ylcarbamoyl)-ethyl]-4-thiophen-2-ylbenzamide N-[2-(3-Hydroxyphenyl)-1-(3-oxo-hexahydrocyclopenta[b]furan-3a-ylcarbamoyl)-ethyl]-5-thiophen-2-ylnicotinamide 2-Phenylthiazole-4-carboxylic acid [2-(3-hydroxyphenyl)-1-(3-oxo-hexahydro-cyclopenta[b]furan-3a-ylcarbamoyl)-ethyl]-amide 2-Pyridin-3-ylthiazole-4-carboxylic acid [2-(3-hydroxyphenyl)-1-(3-oxo-hexahydro-cyclopenta[b]furan-3a-ylcarbamoyl)-ethyl]-amide 4-Phenylthiophene-2-carboxylic acid [2-(3-hydroxyphenyl)-1-(3-oxo-hexahydro-cyclopenta[b]furan-3a-ylcarbamoyl)-ethyl]-amide 2-Thiophen-2-ylthiazole-4-carboxylic acid [2-(3-hydroxyphenyl)-1-(3-oxo-hexahydro-cyclopenta[b]furan-3a-ylcarbamoyl)-ethyl]-amide 3-Phenylpyrrole-1-carboxylic acid [2-(3-hydroxyphenyl)-1-(3-oxo-hexahydro-cyclopenta[b]furan-3a-ylcarbamoyl)-ethyl]-amide 4-tert-Butyl-N-[2-(4-fluorophenyl)-1-(3-oxo-hexahydrocyclopenta[b]furan-3a-ylcarbamoyl)-ethyl]-benzamide N-[2-4-Fluorophenyl)-1-(3-oxo-hexahydrocyclopenta[b]furan-3a-ylcarbamoyl)-ethyl]-4-trifluoromethoxy-benzamide 4-Dimethylamino-N-[2-(4-fluorophenyl)-1-(3-oxo-hexahydrocyclopenta[b]furan-3a-ylcarbamoyl)-ethyl]-benzamide N-[2-(4-Fluorophenyl)-1-(3-oxo-hexahydrocyclopenta[b]furan-3a-ylcarbamoyl)ethyl]-4-isopropyl-benzamide 4-Difluoromethoxy-N-[2-(4-fluorophenyl)-1-(3-oxo-hexahydrocyclopenta[b]furan-3a-ylcarbamoyl)-ethyl]-benzamide N-[2-(4-Fluorophenyl)-1-(3-oxo-hexahydrocyclopenta[b]furan-3a-ylcarbamoyl)-ethyl]-4-trifluoromethyl-benzamide Naphthalene-2-carboxylic acid [2-(4-fluorophenyl)-1-(3-oxo-hexahydro-cyclopenta[b]furan-3a-ylcarbamoyl)-ethyl]-amide Naphthalene-1-carboxylic acid [2-(4-fluorophenyl)-1-(3-oxo-hexahydro-cyclopenta[b]furan-3a-ylcarbamoyl)-ethyl]-amide Quinoline-6-carboxylic acid [2-(4-fluorophenyl)-1-(3-oxo-hexahydro-cyclopenta[b]furan-3a-ylcarbamoyl)-ethyl]-amide Benzo[b]thiophene-2-carboxylic acid [2-(4-fluorophenyl)-1-(3-oxo-hexahydro-cyclopenta[b]furan-3a-ylcarbamoyl)-ethyl]-amide Benzo[b]thiophene-3-carboxylic acid [2-(4-fluorophenyl)-1-(3-oxo-hexahydro-cyclopenta[b]furan-3a-ylcarbamoyl)-ethyl]-amide Benzothiazole-5-carboxylic acid [2-(4-fluorophenyl)-1-(3-oxo-hexahydro-cyclopenta[b]furan-3a-ylcarbamoyl)-ethyl]-amide Biphenyl-4-carboxylic acid [2-(4-fluorophenyl)-1-(3-oxo-hexahydro-cyclopenta[b]furan-3a-ylcarbamoyl)-ethyl]-amide N-[2-(4-Fluorophenyl)-1-(3-oxo-hexahydrocyclopenta[b]furan-3a-ylcarbamoyl)-ethyl]-4-imidazol-1-yl-benzamide N-[2-(4-Fluorophenyl)-1-(3-oxo-hexahydrocyclopenta[b]furan-3a-ylcarbamoyl)-ethyl]-4-thiophen-2-ylbenzamide N-[2-(4-Fluorophenyl)-1-(3-oxo-hexahydrocyclopenta[b]furan-3a-ylcarbamoyl)-ethyl]-5-thiophen-2-ylnicotinamide 2-Phenylthiazole-4-carboxylic acid [2-(4-fluorophenyl)-1-(3-oxo-hexahydro-cyclopenta[b]furan-3a-ylcarbamoyl)-ethyl]-amide 2-Pyridin-3-ylthiazole-4-carboxylic acid [2-(4-fluorophenyl)-1-(3-oxo-hexahydro-cyclopenta[b]furan-3a-ylcarbamoyl)-ethyl]-amide 4-Phenylthiophene-2-carboxylic acid [2-(4-fluorophenyl)-1-(3-oxo-hexahydro-cyclopenta[b]furan-3a-ylcarbamoyl)-ethyl]-amide 2-Thiophen-2-ylthiazole-carboxylic acid [2-(4-fluorophenyl)-1-(3-oxo-hexahydro-cyclopenta[b]furan-3a-ylcarbamoyl)-ethyl]-amide 3-Phenylpyrrole-1-carboxylic acid [2-(4-fluorophenyl)-1-(3-oxo-hexahydro-cyclopenta[b]furan-3a-ylcarbamoyl)-ethyl]-amide 4-tert-Butyl-N-[2-(4-chlorophenyl)-1-(3-oxo-hexahydrocyclopenta[b]furan-3a-ylcarbamoyl)-ethyl]-benzamide N-[2-(4-Chlorophenyl)-1-(3-oxo-hexahydrocyclopenta[b]furan-3a-ylcarbamoyl)-ethyl]-4-trifluoromethoxy-benzamide 4-Dimethylamino-N-[2-(4-chlorophenyl)-1-(3-oxo-hexahydrocyclopenta[b]furan-3a-ylcarbamoyl)-ethyl]-benzamide N-[2-(4-Chlorophenyl)-1-(3-oxo-hexahydrocyclopenta[b]furan-3a-ylcarbamoyl) ethyl]-4-isopropyl-benzamide 4-Difluoromethoxy-N-[2-(4-chlorophenyl)-1-(3-oxo-hexahydrocyclopenta[b]furan-3a-ylcarbamoyl)-ethyl]-benzamide N-[2-(4-Chlorophenyl)-1-(3-oxo-hexahydrocyclopenta[b]furan-3a-ylcarbamoyl)-ethyl]-4-trifluoromethyl-benzamide Naphthalene-2-carboxylic acid [2-(4-chlorophenyl)-1-(3-oxo-hexahydro-cyclopenta[b]furan-3a-ylcarbamoyl)-ethyl]-amide Naphthalene-1-carboxylic acid [2-(4-chlorophenyl)-1-(3-oxo-hexahydro-cyclopenta[b]furan-3a-ylcarbamoyl)-ethyl]-amide Quinoline-6-carboxylic acid [2-(4-chlorophenyl)-1-(3-oxo-hexahydro-cyclopenta[b]furan-3a-ylcarbamoyl)-ethyl]-amide Benzo[b]thiophene-2-carboxylic acid [2-(4-chlorophenyl)-1-(3-oxo-hexahydro-cyclopenta[b]furan-3a-ylcarbamoyl)-ethyl]-amide Benzo[b]thiophene-3-carboxylic acid [2-(4-chlorophenyl)-1-(3-oxo-hexahydro-cyclopenta[b]furan-3a-ylcarbamoyl)-ethyl]-amide Benzothiazole-5-carboxylic acid [2-(4-chlorophenyl)-1-(3-oxo-hexahydro-cyclopenta[b]furan-3a-ylcarbamoyl)-ethyl]-amide Biphenyl-4-carboxylic acid [2-(4-chlorophenyl)-1-(3-oxo-hexahydro-cyclopenta[b]furan-3a-ylcarbamoyl)-ethyl]-amide N-[2-(4-Chlorophenyl)-1-(3-oxo-hexahydrocyclopenta[b]furan-3a-ylcarbamoyl)-ethyl]-4-imidazol-1-yl-benzamide N-[2-(4-Chlorophenyl)-1-(3-oxo-hexahydrocyclopenta[b]furan-3a-ylcarbamoyl)-ethyl]-4-thiophen-2-ylbenzamide N-[2-(4-Chlorophenyl)-1-(3-oxo-hexahydrocyclopenta[b]furan-3a-ylcarbamoyl)-ethyl]-5-thiophen-2-ylnicotinamide 2-Phenylthiazole-4-carboxylic acid [2-(4-chlorophenyl)-1-(3-oxo-hexahydro-cyclopenta[b]furan-3a-ylcarbamoyl)-ethyl]-amide 2-Pyridin-3-ylthiazole-4-carboxylic acid [2-(4-chlorophenyl)-1-(3-oxo-hexahydro-cyclopenta[b]furan-3a-ylcarbamoyl)-ethyl]-amide 4-Phenylthiophene-2-carboxylic acid [2-(4-chlorophenyl)-1-(3-oxo-hexahydro-cyclopenta[b]furan-3a-ylcarbamoyl)-ethyl]-amide 2-Thiophen-2-ylthiazole-4-carboxylic acid [2-(4-chlorophenyl)-1-(3-oxo-hexahydro-cyclopenta[b]furan-3a-ylcarbamoyl)-ethyl]-amide 3-Phenylpyrrole-1-carboxylic acid [2-(4-chlorophenyl)-1-(3-oxo-hexahydro-cyclopenta[b]furan-3a-ylcarbamoyl)-ethyl]-amide 4-tert-Butyl-N-[2-(3,4-dichlorophenyl)-1-(3-oxo-hexahydrocyclopenta[b]furan-3a-ylcarbamoyl)-ethyl]-benzamide N-[2-(3,4-Dichlorophenyl)-1-(3-oxo-hexahydrocyclopenta[b]furan-3a-ylcarbamoyl)-ethyl]-4-trifluoromethoxy-benzamide 4-Dimethylamino-N-[2-(3,4-dichlorophenyl)-1-(3-oxo-hexahydrocyclopenta[b]furan-3a-ylcarbamoyl)-ethyl]-benzamide N-[2-(3,4-Dichlorophenyl)-1-(3-oxo-hexahydrocyclopenta[b]furan-3a-ylcarbamoyl) ethyl]-4-isopropyl-benzamide 4-Difluoromethoxy-N-[2-3,4-dichlorophenyl)-1-(3-oxo-hexahydrocyclopenta[b]furan-3a-ylcarbamoyl)-ethyl]-benzamide N-[2-(3,4-Dichlorophenyl)-1-(3-oxo-hexahydrocyclopenta[b]furan-3a-ylcarbamoyl)-ethyl]-4-trifluoromethyl-benzamide Naphthalene-2-carboxylic acid [2-(3,4-dichlorophenyl)-1-(3-oxo-hexahydro-cyclopenta[b]furan-3a-ylcarbamoyl)-ethyl]-amide Naphthalene-1-carboxylic acid [2-(3,4-dichlorophenyl)-1-(3-oxo-hexahydro-cyclopenta[b]furan-3a-ylcarbamoyl)-ethyl]-amide Quinoline-6-carboxylic acid [2-(3,4-dichlorophenyl)-1-(3-oxo-hexahydro-cyclopenta[b]furan-3a-ylcarbamoyl)-ethyl]-amide Benzo[b]thiophene-2-carboxylic acid [2-(3,4-dichlorophenyl)-1-(3-oxo-hexahydro-cyclopenta[b]furan-3a-ylcarbamoyl)-ethyl]-amide Benzo[b]thiophene-3-carboxylic acid [2-(3,4-dichlorophenyl)-1-(3-oxo-hexahydro-cyclopenta[b]furan-3a-ylcarbamoyl)-ethyl]-amide Benzothiazole-5-carboxylic acid [2-(3,4-dichlorophenyl)-1-(3-oxo-hexahydro-cyclopenta[b]furan-3a-ylcarbamoyl)-ethyl]-amide Biphenyl-4-carboxylic acid [2-(3,4-dichlorophenyl)-1-(3-oxo-hexahydro-cyclopenta[b]furan-3a-ylcarbamoyl)-ethyl]-amide N-[2-(3,4-Dichlorophenyl)-1-(3-oxo-hexahydrocyclopenta[b]furan-3a-ylcarbamoyl)-ethyl]-4-imidazol-1-yl-benzamide N-[2-(3,4-Dichlorophenyl)-1-(3-oxo-hexahydrocyclopenta[b]furan-3a-ylcarbamoyl)-ethyl]-4-thiophen-2-ylbenzamide N-[2-(3,4-Dichlorophenyl)-1-(3-oxo-hexahydrocyclopenta[b]furan-3a-ylcarbamoyl)-ethyl]-5-thiophen-2-ylnicotinamide 2-Phenylthiazole-4-carboxylic acid [2-(3,4-dichlorophenyl)-1-(3-oxo-hexahydro-cyclopenta[b]furan-3a-ylcarbamoyl)-ethyl]-amide 2-Pyridin-3-ylthiazole-4-carboxylic acid [2-(3,4-dichlorophenyl)-1-(3-oxo-hexahydro-cyclopenta[b]furan-3a-ylcarbamoyl)-ethyl]-amide 4-Phenylthiophene-2-carboxylic acid [2-(3,4-dichlorophenyl)-1-(3-oxo-hexahydro-cyclopenta[b]furan-3a-ylcarbamoyl)-ethyl]-amide 2-Thiophen-2-ylthiazole-4-carboxylic acid [2-(3,4-dichlorophenyl)-1-(3-oxo-hexahydro-cyclopenta[b]furan-3a-ylcarbamoyl)-ethyl]-amide 3-Phenylpyrrole-1-carboxylic acid [2-3,4-dichlorophenyl)-1-(3-oxo-hexahydro-cyclopenta[b]furan-3a-ylcarbamoyl)-ethyl]-amide 2-(4-tert-Butyl-benzylsulfanyl)-4-methyl-pentanoic acid (3-oxo-hexahydro-cyclopenta[b]furan-3a-yl)-amide 2-(4-tert-Butyl-benzylsulfanyl)-3-(4-hydroxyphenyl)-N-(3-oxo-hexahydro-cyclopenta[b]furan-3a-yl)-propionamide 2-(4-tert-Butyl-benzylsulfanyl)-3-(3-hydroxyphenyl)-N-(3-oxo-hexahydro-cyclopenta[b]furan-3a-yl)-propionamide 2-(4-tert-Butyl-benzylsulfanyl)-3-(4-fluorophenyl)-N-(3-oxo-hexahydro-cyclopenta[b]furan-3a-yl)-propionamide 2-(4-Hydroxybenzyl)-4-oxo-N-(3-oxo-hexahydrocyclopenta[b]furan-3a-yl)-4-(3-phenyl-pyrrol-1-yl)-butyramide 2-(4-Hydroxybenzyl)-4-oxo-N-(3-oxo-hexahydrocyclopenta[b]furan-3a-yl)-4-(3-phenyl-pyrrolidine-1-yl)-butyramide 4-Methyl-2-[2-oxo-2-(3-phenyl-pyrrol-1-yl)-ethyl]-pentanoic acid (3-oxo-hexahydro-cyclopenta[b]furan-3a-yl)-amide 4-Methyl-2-[2-oxo-2-(3-phenyl-pyrrolidin-1-yl)-ethyl]-pentanoic acid (3-oxo-hexahydro-cyclopenta[b]furan-3a-yl)-amide 2-[2-(1,3-Dihydro-isoindol-2-yl)-2-oxo-ethyl]-4-methyl-pentanoic acid (3-oxo-hexahydro-cyclopenta[b]furan-3a-yl)-amide 4-(1,3-Dihydro-isoindol-2-yl)-2-(4-hydroxybenzyl)-4-oxo-N-(3-oxo-hexahydro-cyclopenta[b]furan-3a-yl)-butyramide 4-(3,4-Dihydro-1H-isoquinolin-2-yl)-2-(4-hydroxybenzyl)-4-oxo-N-(3-oxo-hexahydro-cyclopenta[b]furan-3a-yl)-butyramide 2-[2-(3,4Dihydro-1H-isoquinolin-2-yl)-2-oxo-ethyl]-4-methyl-pentanoic acid (3-oxo-hexahydro-cyclopenta[b]furan-3a-yl)-amide Additional compounds of the invention include, but are not limited to, the following examples that are the (3aR, 6aR) isomer of general formula (I) where Z='O' and R$^1$='H', and also include the equivalent analogues included in the full definition of Z and R$^1$ Furan-2-carboxylic acid [3-methyl-1-(3-oxo-hexahydrocyclopenta[b]furan-3a-ylcarbamoyl)-butyl]-amide Furan-3-carboxylic acid [3-methyl-1-(3-oxo-hexahydrocyclopenta[b]furan-3a-ylcarbamoyl)-butyl]-amide Thiophene-2-carboxylic acid [3-methyl-1-(3-oxo-hexahydrocyclopenta[b]furan-3a-ylcarbamoyl)-butyl]-amide Thiophene-3-carboxylic acid [3-methyl-1-(3-oxo-hexahydrocyclopenta[b]furan-3a-ylcarbamoyl)-butyl]-amide Benzo[b]thiophene-2-carboxylic acid [3-methyl-1-(3-oxo-hexahydro-cyclopenta[b]furan-3a-ylcarbamoyl)-butyl]-amide Furan-2-carboxylic acid [2-cyclohexyl-1-(3-oxo-hexahydrocyclopenta[b]furan-3a-ylcarbamoyl)-ethyl]-amide Furan-3-carboxylic acid [2-cyclohexyl-1-(3-oxo-hexahydrocyclopenta[b]furan-3a-ylcarbamoyl)-ethyl]-amide Thiophene-2-carboxylic acid [[2-cyclohexyl-1-(3-oxo-hexahydrocyclo penta[b]furan-3a-ylcarbamoyl)-ethyl]-amide Thiophene-3-carboxylic acid [2-cyclohexyl-1-(3-oxo-hexahydrocyclo penta[b]furan-3a-ylcarbamoyl)-ethyl]-amide Benzo[b]thiophene-2-carboxylic acid [2-cyclohexyl-1-(3-oxo-hexahydrocyclo penta[b]furan-3a-ylcarbamoyl)-ethyl]-amide Furan-2-carboxylic acid [3,3-dimethyl-1-(3-oxo-hexahydrocyclopenta[b]furan-3a-ylcarbamoyl)-butyl]-amide Furan-3-carboxylic acid [3,3-dimethyl-1-(3-oxo-hexahydrocyclopenta[b]furan-3a-ylcarbamoyl)-butyl]-amide Thiophene-2-carboxylic acid [3,3-dimethyl-1-(3-oxo-hexahydrocyclopenta[b]furan-3a-ylcarbamoyl)-butyl]-amide Thiophene-3-carboxylic acid [3,3-dimethyl-1-(3-oxo-hexahydrocyclopenta[b]furan-3a-ylcarbamoyl)-butyl]-amide Benzo[b]thiophene-2-carboxylic acid [3,3-dimethyl-1-(3-oxo-hexahydrocyclo penta[b]furan-3a-ylcarbamoyl)-butyl]-amide Furan-2-carboxylic acid [2-benzylsulfanyl-1-(3-oxo-hexahydrocyclopenta[b]furan-3a-ylcarbamoyl)-ethyl]-amide Furan-3-carboxylic acid [2-benzylsulfanyl-1-(3-oxo-hexahydrocyclopenta[b]furan-3a-ylcarbamoyl)-ethyl]-amide Thiophene-2-carboxylic acid [2-benzylsulfanyl-1-(3-oxo-hexahydrocyclo penta[b]furan-3a-ylcarbamoyl)-ethyl]-amide Thiophene-3-carboxylic acid [2-benzylsulfanyl-1-(3-oxo-hexahydrocyclo penta[b]furan-3a-ylcarbamoyl)-ethyl]-amide Benzo[b]thiophene-2-carboxylic acid [2-benzylsulfanyl-1-(3-oxo-hexahydrocyclo penta[b]furan-3a-ylcarbamoyl)-ethyl]-amide Furan-2-carboxylic acid [1-(3-oxo-hexahydro-cyclopenta[b]furan-3a-ylcarbamoyl)-2-phenylmethanesulfonyl-ethyl]-amide Furan-3-carboxylic acid (1-(3-oxo-hexahydro-cyclopenta[b]furan-3a-ylcarbamoyl)-2-phenylmethanesulfonyl-ethyl]-amide Thiophene-2-carboxylic acid [1-(3-oxo-hexahydro-cyclopenta[b]furan-3a-ylcarbamoyl)-2-phenylmethanesulfonyl-ethyl]-amide Thiophene-3-carboxylic acid [1-(3-oxo-hexahydro-cyclopenta[b]furan-3a-ylcarbamoyl)-2-phenylmethanesulfonyl-ethyl]-amide Benzo[b]thiophene-2-carboxylic acid [1-(3-oxo-hexahydro-cyclopenta[b]furan-3a-ylcarbamoyl)-2-phenylmethanesulfonyl-ethyl]-amide 2-Benzyloxy-3-cyclohexyl-N-(3-oxo-hexahydrocyclopenta[b]furan-3a-yl)-propionamide Morpholine-4-carboxylic acid 2-cyclohexyl-1-(3-oxo-hexahydrocyclopenta[b]furan-3a-ylcarbamoyl)-ethyl ester 2-Cyclohexylmethyl-4-morpholin-4-yl-4-oxo-N-(3-oxo-hexahydro-cyclopenta[b]furan-3a-yl)-butyramide 2-Biphenyl-3-yl-4-methyl-pentanoic acid (3-oxo-hexahydrocyclopenta[b]furan-3a-yl)-amide 3-Cyclohexyl-2-(furan-2-ylmethylsulfanyl)-N-(3-oxo-hexahydro-cyclopenta[b]furan-3a-yl)-propionamide 3-Cyclohexyl-2-(furan-3-ylmethylsulfanyl)-N-(3-oxo-hexahydro-cyclopenta[b]furan-3a-yl)-propionamide 3-Cyclohexyl-2-(furan-2-ylmethanesulfonyl)-N-(3-oxo-hexahydro-cyclopenta[b]furan-3a-yl)-propionamide 3-Cyclohexyl-2-(furan-3-ylmethanesulfonyl)-N-(3-oxo-hexahydro-cyclopenta[b]furan-3a-yl)-propionamide 2-(4-tert-Butyl-phenylmethanesulfonyl)-4-methyl-pentanoic acid (3-oxo-hexahydrocyclopenta[b]furan-3a-yl)-amide 2-(4-tert-Butyl-benzyloxy)-4-methyl-pentanoic acid (3-oxo-hexahydro-cyclopenta[b]furan-3a-yl)-amide Considering all of the above examples, it is also intended to include the oxidised analogues of capping groups that contain a readily oxidised nitrogen to give the N-oxide or a readily oxidised sulphur to give the sulphone. The following structures are illustrative examples;

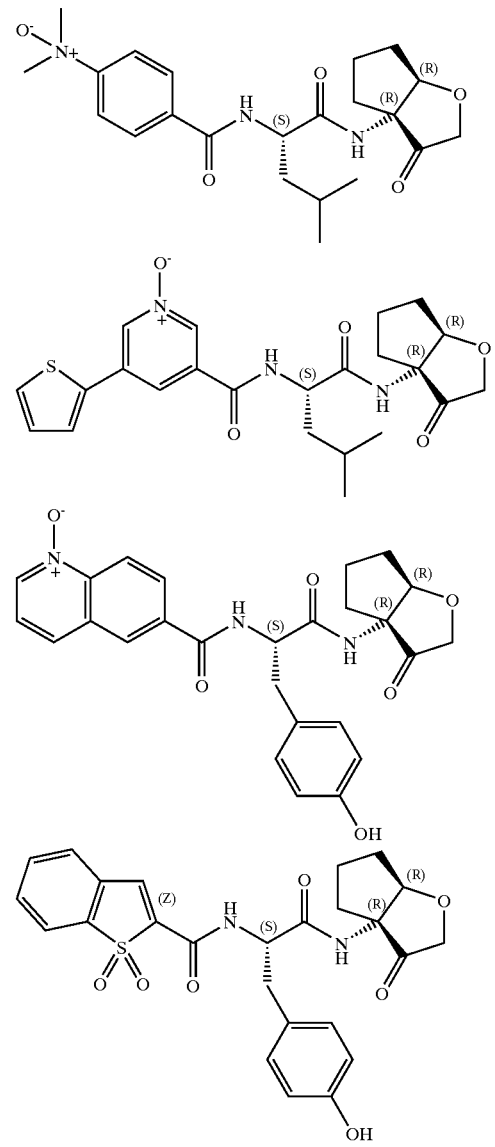

To those skilled in the practices of organic chemistry, compounds of general formula (I) may be readily synthesised by a number of chemical strategies, performed either in solution or on the solid phase (see Atherton, E. and Sheppard, R. C. In '*Solid Phase Peptide Synthesis: A Practical Approach*', Oxford University Press, Oxford, U.K. 1989, for a general review of solid phase synthesis principles). The solid phase strategy is attractive in being able to generate many thousands of analogues, typically on a 5–100 mg scale, through established parallel synthesis methodologies (e.g. see (a) Bastos, M.; Maeji, N. J.; Abeles, R. H. *Proc. Natl. Acad. Sci. USA*, 92, 6738–6742, 1995).

Therefore, one strategy for the synthesis of compounds of general formula (I) comprises:

(a) Preparation of an appropriately functionalised and protected cyclopentane bicyclic ketone building block in solution.
(b) Attachment of the building block (a) to the solid phase through a linker that is stable to the conditions of synthesis, but readily labile to cleavage at the end of a synthesis (see James, I. W., *Tetrahedron*, 55(Report №489), 4855–4946, 1999, for examples of the 'linker' function as applied to solid phase synthesis).
(c) Solid phase organic chemistry (see Brown, R. D. *J. Chem. Soc., Perkin Trans*.1, 19, 3293–3320, 1998), to construct the remainder of the molecule.
(d) Compound cleavage from the solid phase into solution.
(e) Cleavage work-up and compound analysis.

The first stage in a synthesis of compounds of general formula (I) is the preparation in solution of a functionalised and protected building block. A typical scheme towards the (3aR,6aR) N-(3-oxo-hexahydrocyclopenta[b]furan-3a-yl)alkylamide (8) is detailed in Scheme 1.

1-amino-2-hydroxycyclopentanecarboxylic acid (5) via isobutyl chloroformate mixed anhydride, followed by condensation with diazomethane, yields the diazomethylketone intermediate (7). Following the reaction conditions detailed in Scheme 1, formation of the diazoketone is clearly observed. However, an overall improvement in isolated yield of diazoketone (7) is obtained by pre-forming the acyl fluoride of (5), which has a lesser propensity to form the poorly active (5R, 6R) 6-alkoxy-2-(9H-fluoren-9-ylmethoxy)-3-oxa-1-azaapiro[4,4]non-1-en-4-one (6) and diazomethylketone intermediate (7) with lithium chloride in aqueous acetic acid provides the protected (3aR, 6aR) N-(3-oxo-hexahydrocyclopenta[b]furan-3a-yl)alkylamide (8). Introduction of simple $R^1$ substituents may be achieved by condensation of activated (5) with alternatives to diazomethane such as diazoethane ($R^1$=CH$_3$), or 1-phenyloxydiazoethane ($R^1$=CH$_2$OPh).

The protected building blocks (synthesis exemplified by (3aR, 6aR) N-(3-oxo-hexahydrocyclopenta[b]furan-3a-yl) alkylamide (8) detailed in Scheme 1 may be utilised in a solid phase synthesis of inhibitor molecules (steps (b) to (e)).

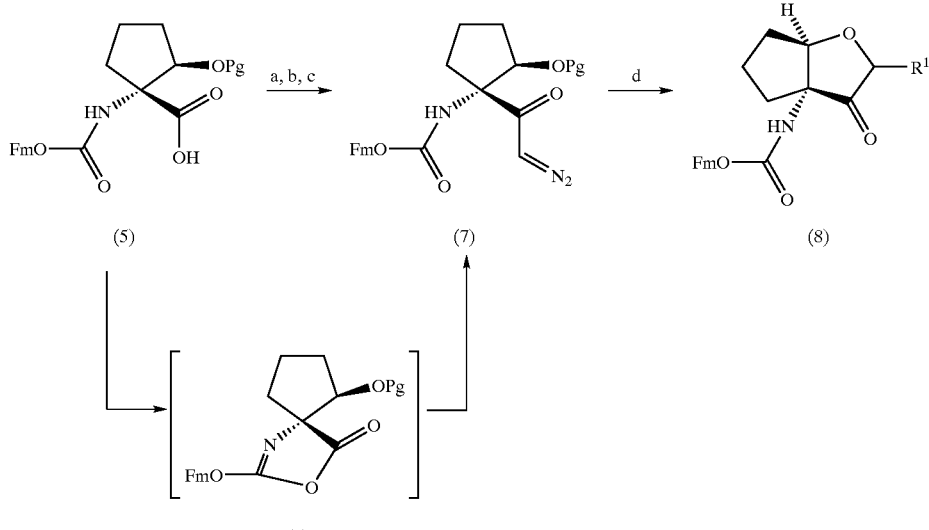

Scheme 1.

(a) $^i$BuOCOCl, NMM, DCM, -15° C., 10 mins, under argon.
(b) Diazomethane in diethyl ether, -15° C., to RT over 1 hr.
(c) Acetic acid
(d) LiCl (10 eq) in 80% aq acetic acid, 5° C. to RT over 1 hr.

FmOC(O) denotes the well known amine protecting group 9-fluorenyl methoxycarbonyl (Fmoc, see Atherton, E. and Sheppard, R. C., 1989) and 'Pg' denotes either a free hydroxyl or an hydroxyl protecting group such as tert-butyl ether. In the illustrated case, condensation with diazomethane provides $R^1$=H.

Considering step (a), synthesis commences from a suitably protected 1-amino-2-hydroxycyclopentanecarboxylic acid (5). The core aminoacid is accessible through a variety of literature methods such as the asymmetric Strecker or Bucherer-Bergs syntheses e.g. (a) Ohfune, Y., Nanba, K., Takada, I., Kan, T., Horikawa, N., Nakajima, T. *Chirality*, 9, 459–462, 1997. (b) Ohfune, Y., Horikawa, N., *J. Synth. Org. Chem Jpn.*, 55, 982–993, 1997. (c) Volk, F-J., Frahm, A. W. *Liebigs Ann. Chem.* 1893–1903, 1996. (d) Fonderkar, K. P., Volk, F-J., Frahm, A. W. *Tetrahedron: Asymmetry*, 10, 727–735, 1999. Activation of the suitably protected Step (b), the solid phase linkage of an aldehyde or ketone, has previously been described by a variety of methods (e.g. see (a) James, I. W., 1999, (b) Lee, A., Huang, L., Ellman, J. A., *J. Am. Chem. Soc*, 121(43), 9907–9914, 1999, (c) Murphy, A. M., et al, J. Am. Chem. Soc, 114, 3156–3157, 1992). A suitable method amenable to the reversible linkage of an alkyl ketone functionality such as (8) is through a combination of the previously described chemistries. The semicarbazide, 4-[[(hydrazinocarbonyl) amino]methyl] cyclohexane carboxylic acid. trifluoroacetate (9) (Murphy, A. M., et al, J. Am. Chem. Soc, 114, 3156–3157, 1992), may be utilised as illustrated in Scheme 2, exemplified by linkage of the (3aR, 6aR) N-(3-oxo-hexahydrocyclopenta[b]furan-3a-yl)alkylamide (8).

Construct (10) is prepared through reaction of the linker molecule (9) and the (3aR, 6aR) N-(3-oxo-hexahydrocyclopenta[b]furan-3a-yl)alkylamide (8) by reflux in aqueous ethanol/sodium acetate. Although formation of construct (10) is observed at 2 hr reaction, optimal formation of construct (10) occurs at 24 hr reaction. Standard solid phase techniques (e.g. see Atherton, E. and Sheppard, R. C., 1989) are used to anchor the construct to an amino-functionalised solid phase through the free carboxylic acid functionality of (10), providing the loaded construct (11). Acid mediated cleavage of the fully constructed compounds is optimal at 24 hr reaction.

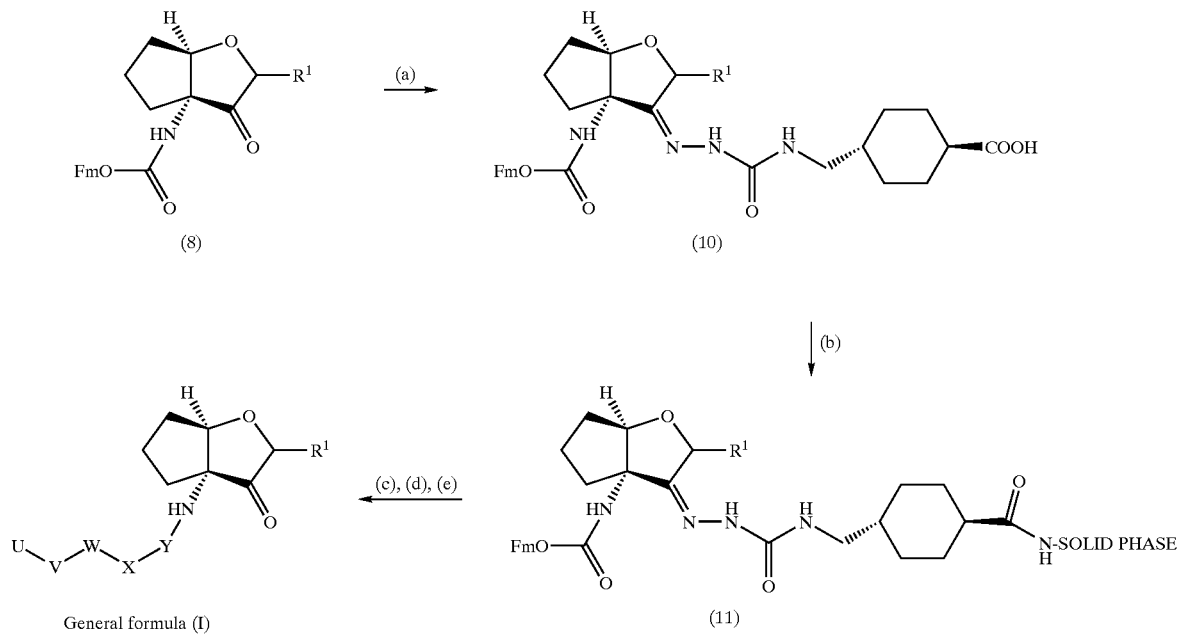

Scheme 2.

(a) (8) in 90% EtOH/H$_2$O/1.5 eq NaOAc/4-[[(hydrazinocarbonyl)amino]methyl]cyclohexane carboxylic acid.trifluoroacetate (9), 24 hr reflux.
(b) 3 eq construct (10)/3 eq HBTU/3 eq HOBt/6 eq NMM, NH$_2$-SOLID PHASE, DMF, RT, o/n.
(c) 20% piperidine/DMF, 30 mins.
(d) Range of chemistries to introduce U-V-W-X-Y (e) TFA/H$_2$O (95:5, v/v), RT, 24 hr.

Loaded construct (11) may be reacted with a wide range of carboxylic acids available commercially or in the literature, to introduce the left-hand portion 'U—V—W—X—Y' in general formula (I). In the simplest example, the entire left hand portion of an inhibitor of general formula (I) comprises a capped aminoacid (Scheme 3), providing for example analogues of general formula (I) where R$^5$='H', (X)$_o$='-', (W)$_n$='NH', R$^9$='H', n=1, (V)$_m$='CO', m=1 and U=aryl Scheme 3.

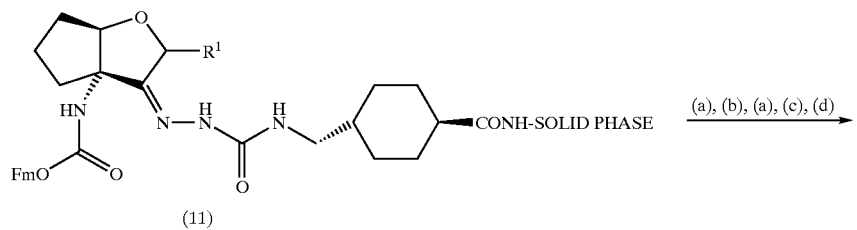

(11)

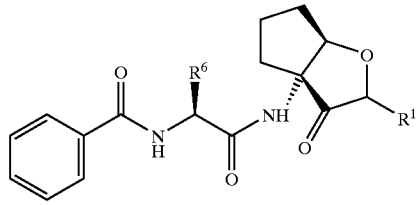

(12)

General formula (I) where
$R^5$ = 'H'
$(X)_o$ = '-'
$(W)_n$ = 'NH', n = 1
$(V)_m$ = 'CO', m = 1
U = phenyl
Z = 'O'

(a) 20% piperidine/DMF, 30 mins
(b) 20 eq Fmoc-aminoacid/20 eq HBTU/20 eq HOBt/40 eq NMM, DMF, o/n
(c) 5 eq carboxylic acid/5 eq HBTU/5 eq HOBt/10 eq NMM, DMF, RT, o/n
(d) TFA/H$_2$O (95:5, v/v), RT, 24 hr Alternatively, carboxylic acids can be prepared in solution by traditional organic chemistry methods and coupled to construct (11) on the solid phase (Schemes 4–8). For example (Scheme 4), treatment in solution of an amino acid, exemplified by (13) with sodium nitrite/H$_2$SO$_4$, provides the α-hydroxyacid, exemplified by (14) (Degerbeck, F. et al, *J. Chem. Soc, Perkin Trans*. 1, 11–14, 1993). Treatment of α-hydroxyacid, (14) with sodium hydride in a dimethylformamide/dichloromethane mixture followed by addition of benzyl bromide, provides 2RS-benzyloxy-3-cyclohexylpropionic acid (15). Coupling of (15) to the solid phase construct (11) followed by cleavage, provides (16), an example of general formula (I) where $R^5$='H', $(X)_o$='-', $(W)_n$='O', n=1, $(V)_m$='CH$_2$', i.e. $R^{10}$, $R^{11}$='H', m=1 and U=phenyl. To those skilled in the practices of organic synthesis, a wide variety of aminoacids such as (13) may be converted to the corresponding α-hydroxyacid such as (14) following the general conditions detailed. Additionally, benzylbromide may be replaced by any reasonable Ar—CR$^{10}$R$^{11}$-halide, providing many variations of carboxylic acid (15) following the general conditions detailed. In certain instances, it may be advantageous to temporarily protect the carboxylic acid as the methyl ester (for example compound (21), Scheme 6) prior to reaction with the alkylhalide. The ester intermediate is then simply hydrolysed to acid (16). Analogues of (16), exploring a wide range of $(V)_m$ and U in general formula (I) may be prepared through the general conditions detailed in Scheme 4. Since the final synthetic step involves a trifluoroacetic acid (TFA) mediated cleavage of the solid phase bound compound, analogues where the substituted ether is labile to TFA may be prepared in solution by an alternative route (see Scheme 11).

Scheme 4.

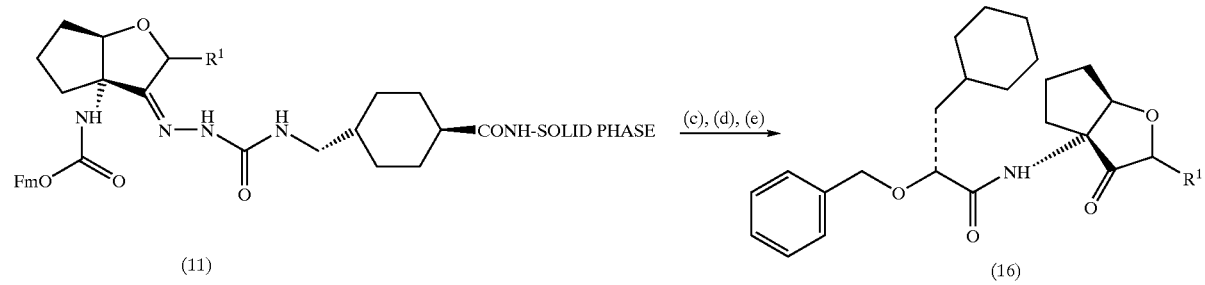

(11)　　　(16)

General formula (I) where
$R^5$ = 'H'
$(X)_O$ = '-'
$(W)_n$ = 'O', n = 1
$(V)_m$ = 'CH$_2$', i.e. $R^{10}$, $R^{11}$ = 'H', m = 1
U = phenyl
Z = 'O'

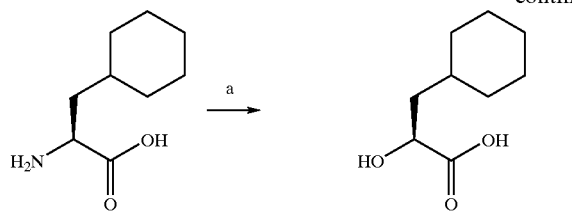
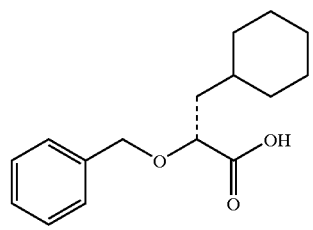

(13) (14) (15)

(a) NaNO₂/H₂SO₄, 0° C. → RT, 2 hr (b) 2.3 eq NaH, 1:1 DMF/DCM, 1.4 eq benzylbromide, o/n
(c) 20% piperidine/DMF, 30 mins.
(d) 10 eq (15)/10 eq HBTU/10 eq HOBt/20 eq NMM, DMF, RT, o/n
(e) TFA/H₂O (95:5, v/v), RT, 24 hr.

Alternatively, coupling of construct (11) (following removal of Fmoc) with the α-hydroxyacid (14), provides a versatile solid phase bound intermediate 'Y' substituent in general formula (I) that may be reacted with many reagents. For example, the α-hydroxyl can be reacted under Mitsunobu conditions (Hughes, D. L. *Org. React.(N.Y)*, 42, 335–656, 1992) to give ethers (i.e. X='-', W='O', in general formula (I)) (see Grabowska, U. et al, *J. Comb. Chem.*, 2(5), 475–490, 2000, for an example of Mitsunobu reaction on the solid phase). Alternatively, the α-hydroxyl can be reacted with a carbamoyl chloride to give a carbamate (i.e. X='-', W='O', V='NHC(O)', in general formula (I)).

Alternatively, (Scheme 5), treatment in solution of an amino acid, exemplified by (13) with sodium nitrite/H₂SO₄/potassium bromide provides the α-bromoacid, exemplified by (17) (Souers, A. J. et al, *Synthesis*, 4, 583–585, 1999) with retention of configuration. Treatment of α-bromoacid (17) with an alkylthiol exemplified by 4-tert-butylphenylmethanethiol (18) in diethylformamide/triethylamine, provides 2S-(4-tert-butylbenzylsulfanyl)-4-methylpropionic acid (19), with inversion of configuration. Coupling of (19) to the solid phase construct (11) followed by cleavage, provides (20), an example of general formula (I) where $R^5$='H', $(X)_o$='-', $(W)_n$='S', n=1, $(V)_m$='CH₂', i.e. $R^{10}$, $R^{11}$='H', m=1 and U=4-tert-butylphenyl. To those skilled in the practices of organic synthesis, a wide variety of aminoacids such as (13) may be converted to the corresponding α-bromoacid such as (17) following the general conditions detailed. Additionally, starting with the S-isomer of (13) gives the S-bromoacid analogue of (17) and R-thioether analogue of (19). Additionally, (4-tert-butylphenyl)methanethiol (18) may be replaced by any reasonable Ar—$CR^{10}R^{11}$—SH, providing many variations of carboxylic acid (19) following the general conditions detailed. Thus analogues of (20) exploring a wide range of $(V)_m$ and U in general formula (I) may be prepared through the general conditions detailed in Scheme 5.

Scheme 5.

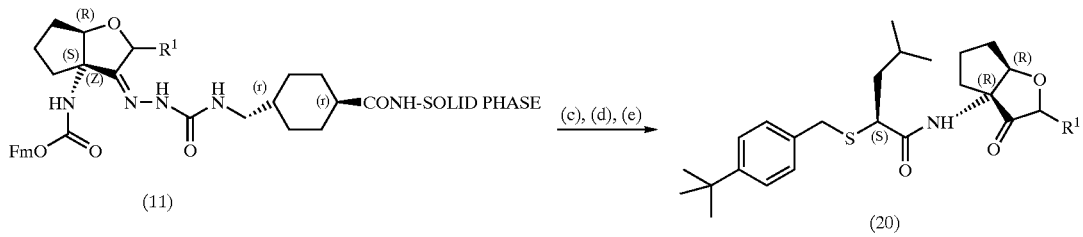

General formula (I) where
$R^5$ = 'H'
$(X)_o$ = '-'
$(W)_n$ = 'S', n = 1
$(V)_m$ = 'CH₂', i.e. $R^{10}$, $R^{11}$ = 'H', m = 1
U = 4-tert-butylphenyl
Z = 'O'

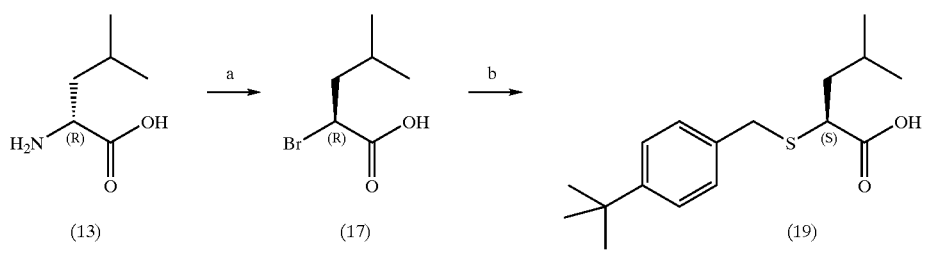

(a) NaNO₂/H₂SO₄, KBr 0° C. → RT, 2 hr
(b) Alkylthiol (18)/DMF/NEt₃, o/n
(c) 20% piperidine/DMF, 30 mins.
(d) 10 eq (19)/10 eq HBTU/10 eq HOBt/20 eq NMM, DMF, RT, o/n
(e) TFA/H₂O (95:5, v/v), RT, 24 hr.

Alternatively, coupling of construct (11) (following removal of Fmoc) with an α-bromoacid e.g. (17), provides a versatile intermediate 'Y' substituent in general formula (I) that may be reacted with many reagents. For example, the α-bromide can be displaced with nucleophiles e.g. alcohols, thiols, carbanions etc, to give ethers (i.e. X='-', W='O', in general formula (I)), thioethers (i.e. X='-', W='S', in general formula (I)). The thioethers may optionally be oxidised to the sulphone (see Scheme 9, i.e. X='-', W='SO₂', in general variety of α-hydroxyacid esters such as (21) could be converted to the activated chloroformate following the general conditions detailed. Additionally, morpholine may be replaced by any reasonable amine, providing many variations of carboxylic acid (22) following the general conditions detailed. Thus analogues of (23) exploring a wide range of (V)ₘ and U in general formula (I) may be prepared through the general conditions detailed in Scheme 6.

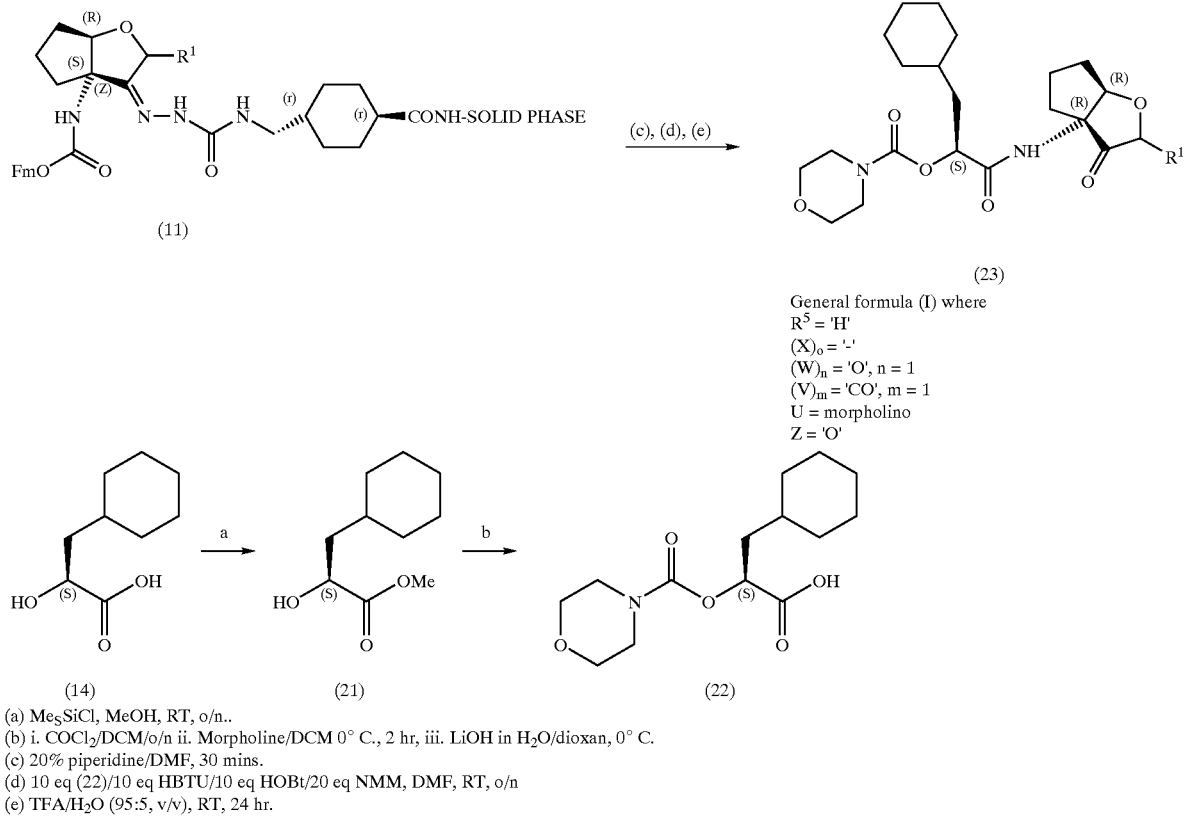

(a) Me₃SiCl, MeOH, RT, o/n..
(b) i. COCl₂/DCM/o/n ii. Morpholine/DCM 0° C., 2 hr, iii. LiOH in H₂O/dioxan, 0° C.
(c) 20% piperidine/DMF, 30 mins.
(d) 10 eq (22)/10 eq HBTU/10 eq HOBt/20 eq NMM, DMF, RT, o/n
(e) TFA/H₂O (95:5, v/v), RT, 24 hr.

formula (I)) (see Grabowska, U. et al, *J. Comb. Chem.*, 2(5), 475–490, 2000, for an example of bromide displacement and thioether oxidation on the solid phase).

Alternatively, (Scheme 6), treatment of an α-hydroxyacid, exemplified by (14) with trimethylsilylchloride and methanol provides the methyl ester (21). Activation of the free hydroxyl to the chloroformate with phosgene in dichloromethane followed by addition of morpholine, then hydrolysis, provides morpholine-4-carboxylic acid-1S-carboxy-2-cyclohexyl ethyl ester (22). Coupling of (22) to the solid phase construct (11) followed by cleavage, provides (23), an example of general formula (I) where R⁵='H', (X)ₒ='-', (W)ₙ='O', n=1, (V)ₘ='CO' and U=morpholino. To those skilled in the practices of organic synthesis, a wide Alternatively, (Scheme 7), a wide range of alkylsuccinate esters exemplified by 2R-cyclohexylmethylsuccinic acid 1-methyl ester (24) are commercially available or readily prepared by known methods (see (a) Azam et al, *J. Chem. Soc. Perkin Trans.* 1, 621-, 1996; (b) Evans et al, *J. Chem. Soc. Perkin Trans.* 1, 103, 2127, 1981; (c) Oikawa et al, *Tet. Lett*, 37, 6169, 1996). Carboxyl activation of alkylsuccinate ester (24) followed by addition of morpholine in dimethylformamide and subsequent ester hydroylsis, provides 2R-cyclohexylmethyl-4-morpholin-4-yl-4-oxo-butyric acid (25). Coupling of (25) to the solid phase construct (11) followed by cleavage, provides (26), an example of general formula (I) where R='H', (X)ₒ='CH₂' i.e. R⁷, R⁸='H', o=1, (W)ₙ='CO', n=1, (V)ₘ='-' and U=morpholino. To those skilled in the practices of organic synthesis, a wide variety of alkylsuccinate esters such as (24) may be prepared and converted to the corresponding substituted alkylsuccinate acid such as (25) following the general conditions detailed. Additionally, morpholine may be replaced by any reasonable amine, providing many variations of carboxylic acid (25) following the general conditions detailed. Thus analogues of (26) exploring a wide range of $(X)_o$, $(V)_m$ and U in general formula (I) may be prepared through the general conditions detailed in Scheme 7.

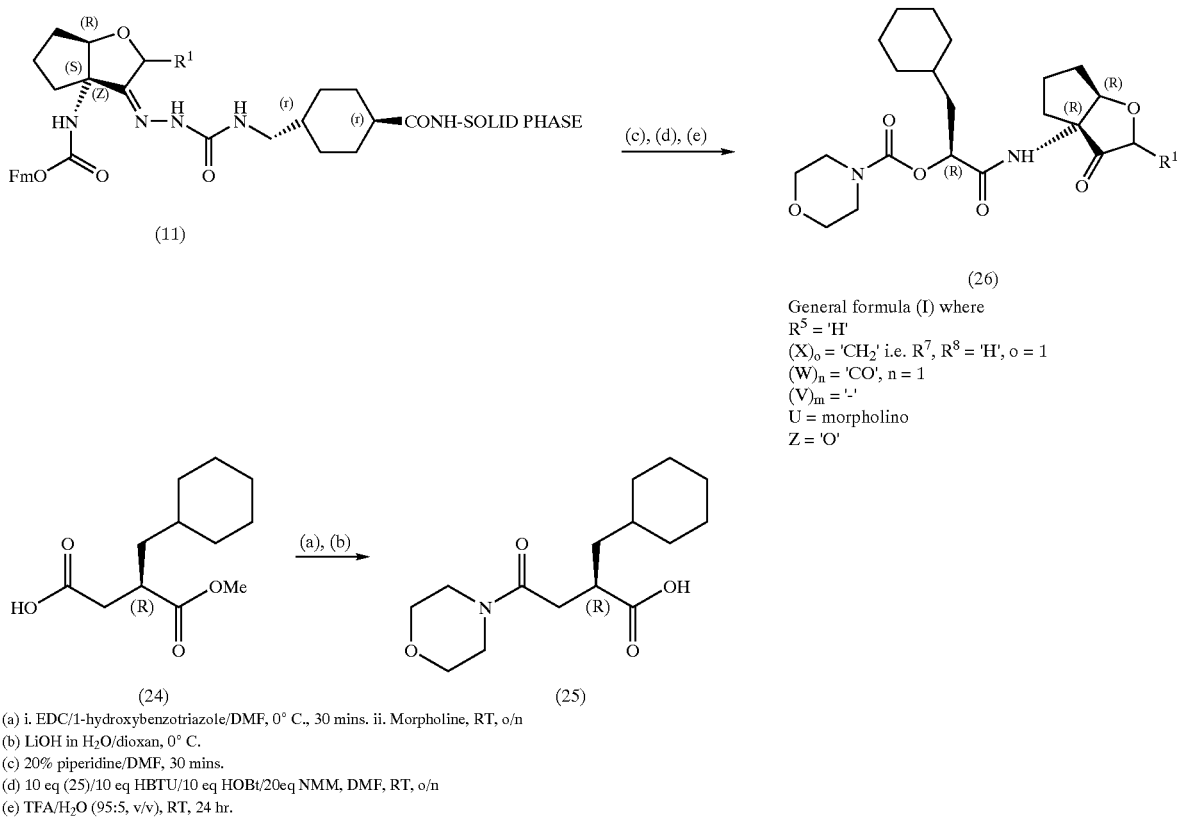

Scheme 7.

(26)
General formula (I) where
$R^5$ = 'H'
$(X)_o$ = '$CH_2$' i.e. $R^7$, $R^8$ = 'H', o = 1
$(W)_n$ = 'CO', n = 1
$(V)_m$ = '-'
U = morpholino
Z = 'O'

(a) i. EDC/1-hydroxybenzotriazole/DMF, 0° C., 30 mins. ii. Morpholine, RT, o/n
(b) LiOH in $H_2O$/dioxan, 0° C.
(c) 20% piperidine/DMF, 30 mins.
(d) 10 eq (25)/10 eq HBTU/10 eq HOBt/20eq NMM, DMF, RT, o/n
(e) TFA/$H_2O$ (95:5, v/v), RT, 24 hr.

Alternatively, (Scheme 8), a wide range of biarylalkylacetic acids, exemplified by 2RS-biphenyl-3-yl-4-methylpentanoic acid (28) are readily available by known methods (see (a) DesJarlais, R. L. et al, *J. Am. Chem. Soc*, 120, 9114–9115, 1998; (b) Oballa, R. M. et al, WO 0149288). Coupling of biarylalkylacetic acid (28) to the solid phase construct (11) followed by cleavage, provides (29), an example of general formula (I) where $R^5$='H', $(X)_o$='-', $(W)_n$='-', $(V)_m$='-' and U=m-biphenyl. To those skilled in the practices of organic synthesis, a wide variety of biarylalkylacetic acids such as (28) may be prepared by alkylation of the α-anion of the free acid analogue of (27), which in turn is prepared by Suzuki coupling of phenylboronic acid and 3-bromophenylacetic acid methyl ester. Phenylboronic acid may be replaced by a wide range of arylboronic acids in the Suzuki coupling, providing many variations of carboxylic acid (28) following the general conditions detailed. Thus analogues of (29) exploring a wide range of group 'U' in general formula (I) may be prepared through the general conditions detailed in Scheme 8.

Scheme 8.

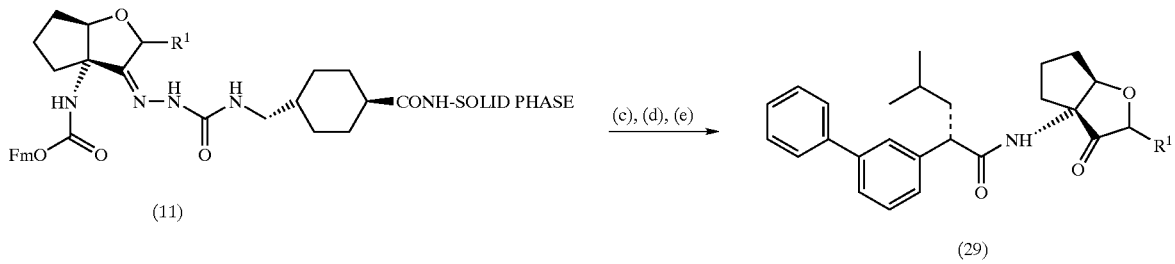

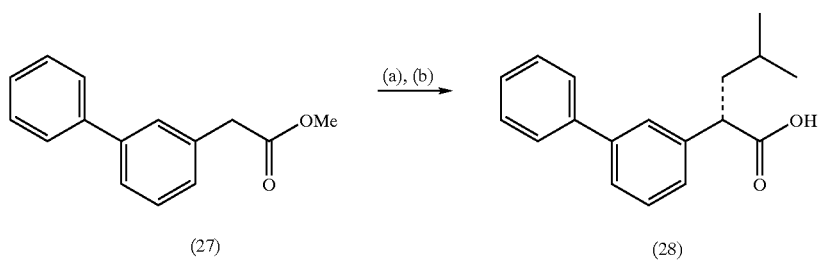

(a) LiOH in H$_2$O/dioxan, 0° C.
(b) i. LDA, THF, 2-methylpropenylbromide. ii. Pd/C, EtOH, H$_2$
(c) 20% piperidine/DMF, 30 mins.
(d) 10 eq (28)/10 eq HBTU/10 eq HOBt/20 eq NMM, DMF, RT, o/n
(e) TFA/H$_2$O (95:5, v/v), RT, 24 hr.

Many other possibilities for solid phase organic chemistry (e.g. see Brown, R. D. *J. Chem. Soc., Perkin Trans.*1, 19, 3293–3320, 1998, for a review of recent SPOC publications) can be used to derivatise construct (11) towards compounds of general formula (I). For example, the left-hand portion 'U—V—W—X—Y' in general formulae (I) can be partially constructed in solution, coupled to construct (11) and further modified on the solid phase. For example (Scheme 9), a simple extension of Scheme 5 is through the oxidation of the intermediate solid phase bound species, with m-chloroperbenzoic acid in dichloromethane prior to cleavage, to give the sulphone analogue (30), an example of general formula (I) where R$^5$='H', (X)$_o$='-', (W)$_n$='SO$_2$', n=1, (V)$_m$='CH$_2$', i.e. R$^{10}$, R$^{11}$='H', m=1 and U=4-tert-butylphenyl. As described in Scheme 5, many variations of carboxylic acid (19) may be prepared following the general conditions detailed. Thus analogues of (30) exploring a wide range of (V)$_m$ and U in general formula (I) may be prepared through the general conditions detailed in Schemes 5 and 9.

Scheme 9.

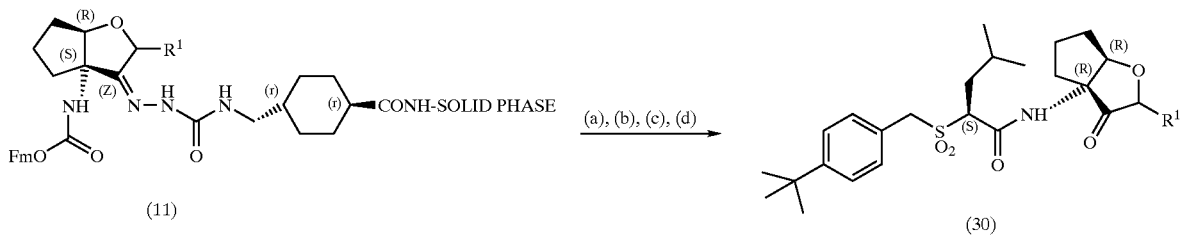

General formula (I) where
R$^5$ = 'H'
(X)$_o$ = '-'
(W)$_n$ = 'SO$_2$', n = 1
(V)$_m$ = 'CH$_2$', i.e. R$^{10}$, R$^{11}$ = 'H', m = 1
U = 4-tert-butylphenyl
Z = 'O'

(a) 20% piperidine/DMF, 30 mins.
(b) 10 eq (19)/10 eq HBTU/10 eq HOBt/20 eq NMM, DMF, RT, o/n
(c) 5 eq m-chloroperbenzoic acid/DCM, RT, 5 hr.
(d) TFA/H$_2$O (95:5, v/v), RT, 24 hr.

Compounds of general formula (I) are finally released from the solid phase by treatment with trifluoroacetic acid/water, followed by evaporation, lyophylis and standard analytical characterisation.

A second strategy for the synthesis of compounds of general formula (I) comprises:

(f) Preparation of an appropriately functionalised and protected (3aR, 6aR) N-(3-oxo-hexahydrocyclopenta[b]furan-3a-yl)alkylamide, (3aS,6aR) N-(3-oxo-hexahydrocyclopenta[b]thiophen-3a-yl)alkylamide, (3aR,6aS) N-(3-oxo-hexahydropentalen-3a-yl)alkylamide or (3aR,6aR) N-(3-oxo-hexahydrocyclo penta[b]pyrrol-3a-yl)alkylamide building block in solution. Preferred protecting groups for solution phase chemistry are the Nα-tert-butoxycarbonyl group and the Nα-benzyloxycarbonyl group.

(g) Standard organic chemistry methods for the conversion of building block (f) towards compounds of general formula (I), (Scheme 10).

An attractive alternative to the mixed anhydride activation of (31) is through the use of the pre-formed acyl fluoride (akin to that detailed in Scheme 1). The general strategy detailed in Scheme 10 is particularly useful when the compound of general formula (I) contains a substituent that is labile to trifluoroacetic acid, this being the final reagent used in each of the solid phase Schemes 4–9. For example (Scheme 11), treatment in solution of α-hydroxyacid (35) with sodium hydride in a dimethylformamide/dichloromethane mixture followed by addition of 4-tert-butylbenzyl bromide, provides 2RS-(4-tert-butylbenzyloxy)-4-methylpentanoic acid (36). Coupling of (36) to hydrochloride salt (34), provides (37), an example of general formula (I) where $R^5$='H', $(X)_o$='-', $(W)_n$='O', n=1, $(V)_m$='CH$_2$', i.e. $R^{10}$, $R^{11}$='H', m=1 and U=4-tert-butylphenyl. To those skilled in the practices of organic synthesis, 4-tert-butylbenzyl bromide may be replaced by any reasonable Ar—CR$^{10}$R$^{11}$-halide, providing many variations of carboxylic acid (36) under the conditions shown. Thus analogues of (37) exploring a wide range of $(V)_m$ and U in general formula (I) may be prepared through the conditions detailed in Scheme 11.

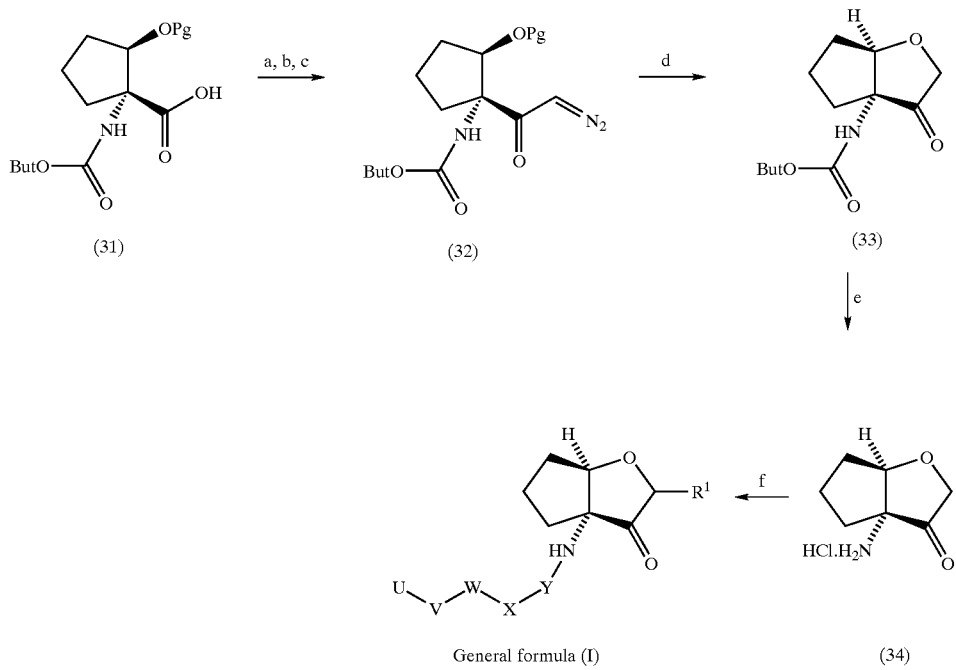

Scheme 10.

General formula (I)

(a) Pre-formed acyl fluoride
(b) Diazomethane in diethyl ether, -15° C. to RT over 24 hr.
(c) Acetic acid
(d) LiCl (10 eq) in 80% aq acetic acid, 5° C. to RT over 1 hr.
(e) 4M HCl in dioxan, 0° C., 2 hrs.
(f) Pre-prepared U-V-W-X-Y-COOH/activation e.g. HATU/HOAt/NMM, DMF, RT, o/n.

Scheme 11.

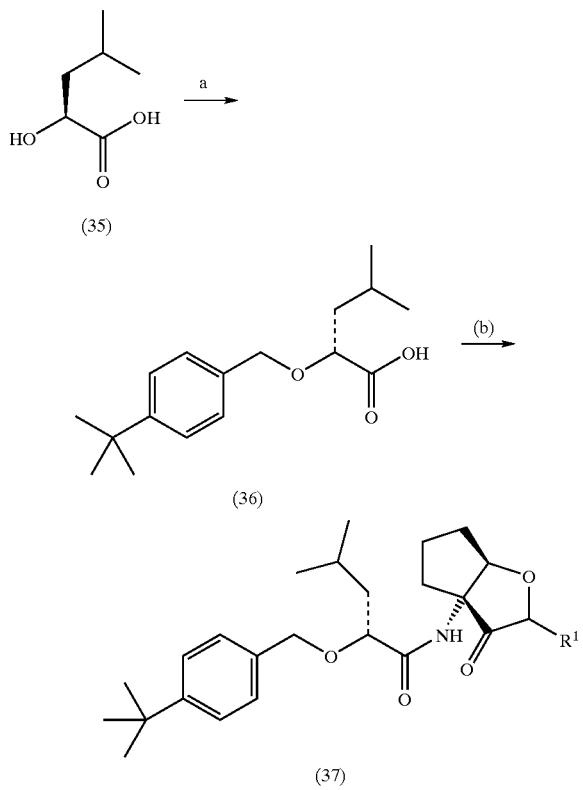

General formula (I) where
$R^5$ = 'H'
$(X)_o$ = '-'
$(W)_n$ = 'O', n = 1
$(V)_m$ = '$CH_2$', i.e. $R^{10}$, $R^{11}$ = 'H', m = 1
U = 4-tert-butylphenyl
Z = 'O'

(a) 2.2 eq NaH, 1:1 DMF/DCM, 1.25 eq 4-tert-benzylbromide, 2 hr
(b) 1eq (36), 1 eq $^i$BuOCOCl, 2 eq NMM, DCM, -15° C., 1 hr, under nitrogen, then 1 eq (34), RT, o/n.

A third strategy for the synthesis of compounds of general formula (I) where the addition of U—V—W—X—Y to the protected (3aR,6aR) N-(3-oxo-hexahydrocyclo-penta[b] furan-3a-yl)alkylamide, (3aS,6aR) N-(3-oxo-hexahydrocyclopenta[b]thiophen-3a-yl)alkylamide, (3aR, 6aS) N-(3-oxo-hexahydropentalen-3a-yl)alkyl amide or (3aR,6aR) N-(3-oxo-hexahydrocyclopenta[b]pyrrol-3a-yl) alkylamide building block involves multistep organic reactions comprises:

(h) Preparation of an appropriately functionalised and protected (3aR, 6aR) N-(3-oxo-hexahydrocyclopenta[b] furan-3a-yl)alkylamide, (3aS, 6aR) N-(3-oxo-hexa hydrocyclopenta[b]thiophen-3a-yl)alkylamide, (3aR, 6aS) N-(3-oxo-hexahydro pentalen-3a-yl)alkylamide or (3aR,6aR) N-(3-oxo-hexahydrocyclopenta [b]pyrrol-3a-yl)alkylamide building block in solution. Preferred protecting groups for solution phase chemistry are the Nα-tert-butoxycarbonyl group and the Nα-benzyloxycarbonyl group.

(i) Protection of the ketone functionality of the (3aR, 6aR) N-(3-oxo-hexahydrocyclopenta[b]furan-3a-yl)alkyl amide, (3aS, 6aR) N-(3-oxo-hexahydrocyclopenta[b] thiophen-3a-yl)alkylamide, (3aR, 6aS) N-(3-oxo-hexahydropentalen-3a-yl)alkylamide or (3aR, 6aR) N-(3-oxo-hexahydrocyclo penta[b]pyrrol-3a-yl)alkylamide building block e.g. as a dimethylacetal.

Alternatively, the ketone may be reduced to the achiral secondary alcohols and re-oxidised as the final synthetic step.

(j) Standard organic chemistry methods for the conversion of building block (i) towards compounds of general formula (I).

Intermediates may be prepared in solution, followed by coupling to building block (i) and further derivitisation towards compounds of general formula (I) (see Scheme 12 exemplified by preparation and use of the (3-hydroxyhexahydrocyclopenta[b]furan-3a-yl)carbamic acid tert-butyl ester (38)).

Scheme 12.

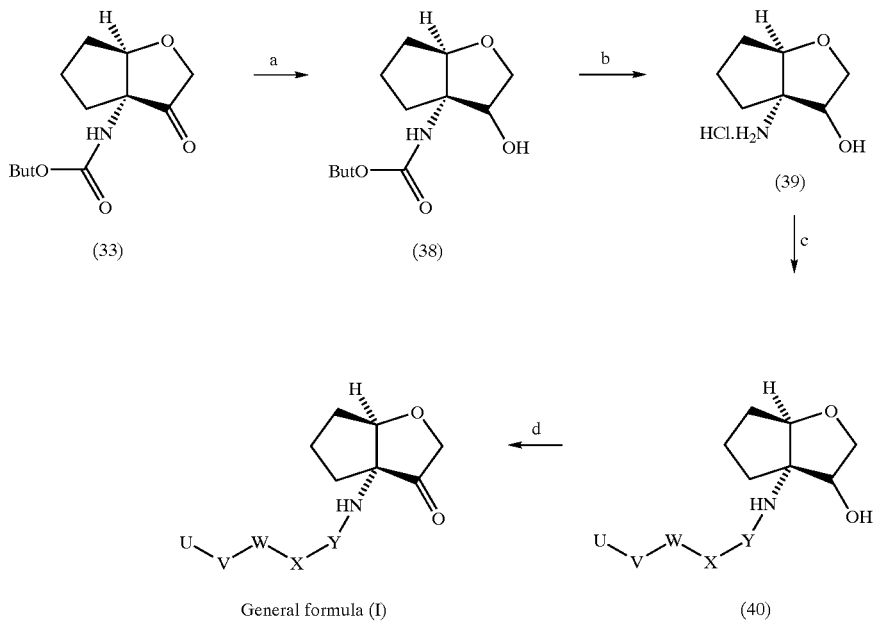

(a) Reduction, e.g. NaBH$_4$
(b) 4M HCl in dioxan, 0° C., 2 hrs.
(c) Stepwise reaction with intermediates of Y, then X, then W etc., to stepwise construct compounds (40).
(d) Oxidation, e.g. Dess-Martin periodane, CH$_2$Cl$_2$.

Alternatively, depending upon the types of chemistry used to construct the left hand side U—V—W—X—Y of compounds of general formula (I), the ketone may require protection e.g. as the dimethyl acetal. Such a method is detailed and exemplified in Scheme 13 by the preparation and use of (3,3-dimethoxyhexahydrocyclo penta[b]furan-3a-yl)carbamic acid benzyl ester (42).

(c) monitoring a cell-based functional marker of a particular cysteine protease activity, in the presence of the compound; and (d) monitoring an animal model-based functional marker of a particular cysteine protease activity in the presence of the compound.

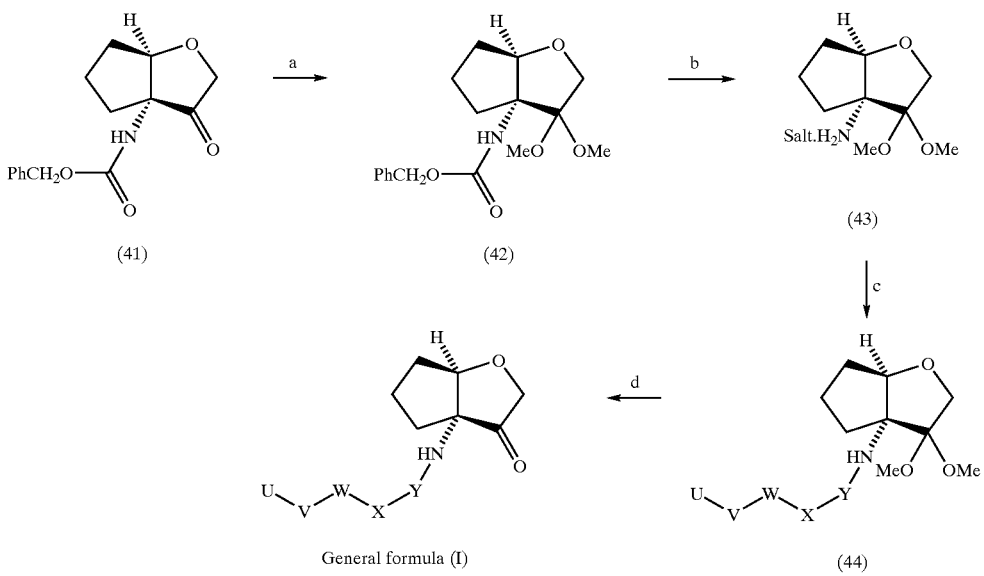

Scheme 13.

(a) Triethylorthoformate/pTSA/MeOH.
(b) H$_2$, Pd——C.
(c) Stepwise reaction with intermediates of Y, then X, then W, etc., to stepwise construct compounds (44).
(d) Trifluoroacetic acid/CH$_2$Cl$_2$/H$_2$O.

The invention extends to novel intermediates as described above, and to processes for preparing compounds of general formula (I) from each of its immediate precursors. In turn, processes for preparing intermediates from their immediate precursors also form part of the invention.

Compounds of general formula (I) are useful both as laboratory tools and as therapeutic agents. In the laboratory certain compounds of the invention are useful in establishing whether a known or newly discovered cysteine protease contributes a critical or at least significant biochemical function during the establishment or progression of a disease state, a process commonly referred to as 'target validation'.

According to a second aspect of the invention, there is provided a method of validating a known or putative cysteine protease as a therapeutic target, the method comprising:

(a) assessing the in vitro binding of a compound as described above to an isolated known or putative cysteine protease, providing a measure of potency; and optionally, one or more of the steps of:

(b) assessing the binding of the compound to closely related homologous proteases of the target and general housekeeping proteases (e.g. trypsin) to provides a measure of selectivity;

The invention therefore provides a method of validating a known or putative cysteine protease as a therapeutic target. Differing approaches and levels of complexity are appropriate to the effective inhibition and 'validation' of a particular target. In the first instance, the method comprises assessing the in vitro binding of a compound of general formula (I) to an isolated known or putative cysteine protease, providing a measure of 'potency'. An additional assessment of the binding of a compound of general formula (I) to closely related homologous proteases of the target and general house-keeping proteases (e.g. trypsin) provides a measure of 'selectivity'. A second level of complexity may be assessed by monitoring a cell-based functional marker of a particular cysteine protease activity, in the presence of a compound of general formula (I). For example, a 'human osteoclast resorption assay' has been utilised as a cell-based secondary in vitro testing system for monitoring the activity of cathepsin K and the biochemical effect of protease inhibitors (e.g. see WO-A-9850533). An 'MHC-II processing—T-cell activation assay' has been utilised as a cell-based secondary in vitro testing system for monitoring the activity of cathepsin S and the biochemical effect of protease inhibitors (Shi. G-P., et al, *Immunity*, 10, 197–206, 1999). When investigating viral or bacterial infections such a marker could simply be a functional assessment of viral (e.g. count of mRNA copies) or bacterial loading and assessing the biochemical effect of protease inhibitors. A third level of complexity may be assessed by monitoring an animal model-based functional marker of a particular cysteine protease activity, in the presence of a compound of general formula (I). For example, murine models of *Leishmania* infection, *P. vinckei* infection, malaria (inhibition of falcipain) and *T. cruzi* infection (cruzipain), indicate that inhibition of cysteine proteases that play a key role in pathogen propagation is effective in arresting disease symptoms, 'validating' said targets.

The invention therefore extends to the use of a compound of general formula (I) in the validation of a known or putative cysteine protease as a therapeutic target.

Compounds of general formula (I) are useful for the in vivo treatment or prevention of diseases in which participation of a cysteine protease is implicated.

According to a third aspect of the invention, there is provided a compound of general formula (I) for use in medicine, especially for preventing or treating diseases in which the disease pathology may be modified by inhibiting a cysteine protease.

According to a fourth aspect of the invention, there is provided the use of a compound of general formula (I) in the preparation of a medicament for preventing or treating diseases in which the disease pathology may be modified by inhibiting a cysteine protease.

Certain cysteine proteases function in the normal physiological process of protein degradation in animals, including humans, e.g. in the degradation of connective tissue. However, elevated levels of these enzymes in the body can result in pathological conditions leading to disease. Thus, cysteine proteases have been implicated in various disease states, including but not limited to, infections by *Pneumocystis carinii*, *Trypsanoma cruzi*, *Trypsanoma brucei brucei* and *Crithidia fusiculata*; as well as in osteoporosis, autoimmunity, schistosomiasis, malaria, tumour metastasis, metachromatic leukodystrophy, muscular dystrophy, amytrophy, and the like. See WO-A-9404172 and EP-A-0603873 and references cited in both of them. Additionally, a secreted bacterial cysteine protease from *S. Aureus* called staphylopain has been implicated as a bacterial virulence factor (Potempa, J., et al. *J. Biol. Chem*, 262(6), 2664–2667, 1998).

The invention is useful in the prevention and/or treatment of each of the disease states mentioned or implied above. The present invention also is useful in a methods of treatment or prevention of diseases caused by pathological levels of cysteine proteases, particularly cysteine proteases of the papain superfamily, which methods comprise administering to an animal, particularly a mammal, most particularly a human, in need thereof a compound of the present invention. The present invention particularly provides methods for treating diseases in which cysteine proteases are implicated, including infections by *Pneumocystis carinii*, *Trypsanoma cruzi*, *Trypsanoma brucei*, *Leishmania mexicana*, *Clostridium histolyticum*, *Staphylococcus aureus*, foot-and-mouth disease virus and *Crithidia fusiculata*; as well as in osteoporosis, autoimmunity, schistosomiasis, malaria, tumour metastasis, metachromatic leukodystrophy, muscular dystrophy and amytrophy.

Inhibitors of cruzipain, particularly cruzipain-specific compounds, are useful for the treatment of Chagas' disease.

In accordance with this invention, an effective amount of a compound of general formula (I) may be administered to inhibit the protease implicated with a particular condition or disease. Of course, this dosage amount will further be modified according to the type of administration of the compound. For example, to achieve an "effective amount" for acute therapy, parenteral administration of a compound of general formula a) is preferred. An intravenous infusion of the compound in 5% dextrose in water or normal saline, or a similar formulation with suitable excipients, is most effective, although an intramuscular bolus injection is also useful. Typically, the parenteral dose will be about 0.01 to about 100 mg/kg; preferably between 0.1 and 20 mg/kg, in a manner to maintain the concentration of drug in the plasma at a concentration effective to inhibit a cysteine protease. The compounds may be administered one to four times daily at a level to achieve a total daily dose of about 0.4 to about 400 mg/kg/day. The precise amount of an inventive compound which is therapeutically effective, and the route by which such compound is best administered, is readily determined by one of ordinary skill in the art by comparing the blood level of the agent to the concentration required to have a therapeutic effect. Prodrugs of compounds of the present invention may be prepared by any suitable method. For those compounds in which the prodrug moiety is a ketone functionality, specifically ketals and/or hemiacetals, the conversion may be effected in accordance with conventional methods.

The compounds of this invention may also be administered orally to the patient, in a manner such that the concentration of drug is sufficient to inhibit bone resorption or to achieve any other therapeutic indication as disclosed herein. Typically, a pharmaceutical composition containing the compound is administered at an oral dose of between about 0.1 to about 50 mg/kg in a manner consistent with the condition of the patient. Preferably the oral dose would be about 0.5 to about 20 mg/kg.

No unacceptable toxicological effects are expected when compounds of the present invention are administered in accordance with the present invention. The compounds of this invention, which may have good bioavailability, may be tested in one of several biological assays to determine the concentration of a compound which is required to have a given pharmacological effect.

According to a fifth aspect of the invention, there is provided a pharmaceutical or veterinary composition comprising one or more compounds of general formula (I) and a pharmaceutically or veterinarily acceptable carrier. Other active materials may also be present, as may be considered appropriate or advisable for the disease or condition being treated or prevented.

The carrier, or, if more than one be present, each of the carriers, must be acceptable in the sense of being compatible with the other ingredients of the formulation and not deleterious to the recipient.

The formulations include those suitable for rectal, nasal, topical (including buccal and sublingual), vaginal or parenteral (including subcutaneous, intramuscular, intravenous and intradermal) administration, but preferably the formulation is an orally administered formulation. The formulations may conveniently be presented in unit dosage form, e.g. tablets and sustained release capsules, and may be prepared by any methods well known in the art of pharmacy.

Such methods include the step of bringing into association the above defined active agent with the carrier. In general, the formulations are prepared by uniformly and intimately bringing into association the active agent with liquid carriers or finely divided solid carriers or both, and then if necessary shaping the product. The invention extends to methods for preparing a pharmaceutical composition comprising bringing a compound of general formula (I) in conjunction or association with a pharmaceutically or veterinarily acceptable carrier or vehicle.

Formulations for oral administration in the present invention may be presented as: discrete units such as capsules, cachets or tablets each containing a predetermined amount of the active agent; as a powder or granules; as a solution or a suspension of the active agent in an aqueous liquid or a non-aqueous liquid; or as an oil-in-water liquid emulsion or a water in oil liquid emulsion; or as a bolus etc.

For compositions for oral administration (e.g. tablets and capsules), the term "acceptable carrier" includes vehicles such as common excipients e.g. binding agents, for example syrup, acacia, gelatin, sorbitol, tragacanth, polyvinylpyrrolidone (Povidone), methylcellulose, ethylcellulose, sodium carboxymethylcellulose, hydroxypropylmethylcellulose, sucrose and starch; fillers and carriers, for example corn starch, gelatin, lactose, sucrose, microcrystalline cellulose, kaolin, mannitol, dicalcium phosphate, sodium chloride and alginic acid; and lubricants such as magnesium stearate, sodium stearate and other metallic stearates, glycerol stearate stearic acid, silicone fluid, talc waxes, oils and colloidal silica. Flavouring agents such as peppermint, oil of wintergreen, cherry flavouring and the like can also be used. It may be desirable to add a colouring agent to make the dosage form readily identifiable. Tablets may also be coated by methods well known in the art. A tablet may be made by compression or moulding, optionally with one or more accessory ingredients. Compressed tablets may be prepared by compressing in a suitable machine the active agent in a free flowing form such as a powder or granules, optionally mixed with a binder, lubricant, inert diluent, preservative, surface-active or dispersing agent. Moulded tablets may be made by moulding in a suitable machine a mixture of the powdered compound moistened with an inert liquid diluent. The tablets may be optionally be coated or scored and may be formulated so as to provide slow or controlled release of the active agent.

Other formulations suitable for oral administration include lozenges comprising the active agent in a flavoured base, usually sucrose and acacia or tragacanth; pastilles comprising the active agent in an inert base such as gelatin and glycerin, or sucrose and acacia; and mouthwashes comprising the active agent in a suitable liquid carrier.

Parenteral formulations will generally be sterile.

According to a sixth aspect of the invention, there is provided a process for the preparation of a pharmaceutical or veterinary composition as described above, the process comprising bringing the active compound(s) into association with the carrier, for example by admixture.

Preferred features for each aspect of the invention are as for each other aspect mutatis mutandis.

The invention will now be illustrated with the following examples:

Solution Phase Chemistry—General Methods

All solvents were purchased from ROMIL Ltd (Waterbeach, Cambridge, UK) at SpS or Hi-Dry grade unless otherwise stated. General peptide synthesis reagents were obtained from Chem-Impex Intl. Inc. (Wood Dale Ill. 60191. USA). Thin layer chromatography (TLC) was performed on pre-coated plates (Merck aluminium sheets silica 60 F254, part no. 5554). Visualisation of compounds was achieved under ultraviolet light (254 nm) or by using an appropriate staining reagent. Flash column purification was performed on silica gel 60 (Merck 9385). All analytical HPLC were obtained on Phenomenex Jupiter $C_4$, 5µ, 300 A, 250×4.6 mm, using mixtures of solvent A=0.1% aq trifluoroacetic acid (TFA) and solvent B=90% acetonitrile/10% solvent A on automated Agilent systems with 215 and/or 254 nm UV detection. Unless otherwise stated a gradient of 10–90% B in A over 25 minutes at 1.5 mL/min was performed for full analytical HPLC analysis. HPLC-MS analysis was performed on an Agilent 1100 series LC/MSD, using automated Agilent HPLC systems, with a gradient of 10–90% B in A over 10 minutes on Phenomenex Columbus $C_8$, 5µ, 300 A, 50×2.0 mm at 0.4 mL/min. Nuclear magnetic resonance (NMR) were obtained on a Bruker DPX400 (400 MHz 1H frequency; QXI probe) in the solvents and temperature indicated. Chemical shifts are expressed in parts per million (δ) and are referenced to residual signals of the solvent. Coupling constants (J) are expressed in Hz.

Solid Phase Chemistry—General Methods

Example inhibitors (1–12) were prepared through a combination of solution and solid phase Fmoc-based chemistries (see 'Solid Phase Peptide Synthesis', Atherton, E. and Sheppard, R. C., IRL Press Ltd, Oxford, UK, 1989, for a general description). An appropriately protected and functionalised building block was prepared in solution (e.g. compound (8), Scheme 1), then reversibly attached to the solid phase through an appropriate linker. Rounds of coupling/deprotection/chemical modification e.g. oxidation were then performed until the full length desired molecule was complete (Scheme 2). Example inhibitors (1–12) were then released (cleaved) from the solid phase, analysed, purified and assayed for inhibition verses a range of proteases.

Generally, multipins (polyamide 1.2→10 µmole loadings, see www.mimotopes.com) were used for the solid phase synthesis, although any suitable solid phase surface could be chosen. In general, the 1.2 µmole gears were used to provide small scale crude examples for preliminary screening, whilst the 10 µmole crowns were used for scale-up synthesis and purification of preferred examples. Standard coupling and Fmoc deprotection methods were employed (see Grabowska, U. et al, *J. Comb. Chem.* 2(5), 475–490, 2000, for a thorough description of solid phase multipin methodologies).

Preparation of Initial Assembly

Building Block-linker constructs (e.g.(10)) were carboxyl activated with 2-(1H-benzotriazole-1-yl)-1,1,3,3-tetramethyluronium hexafluoro phosphate (HBTU, 1 mole equivalent), 1-hydroxybenzotriazole.hydrate (HOBT, 1 mole equivalent) and N-methylmorpholine (NMM, 2 mole equivalents) in dimethylformamide (DMF, typically 1 to 10 mL) for 5 minutes. Amino functionalised DA/MDA crowns or HEMA gears (10 µmole per crown/1.2 µmole per gear, 0.33 mole equivalent of total surface amino functionalisation compared to activated construct) were added, followed by additional DMF to cover the solid phase surface. The loading reaction was left overnight. Following overnight loading, crowns/gears were taken through standard cycles washing, Fmoc deprotection and loading quantification (see Grabowska, U. et al) to provide loaded Building Block-linker constructs (e.g.(11)). Analysis indicated virtually quantitative loading in all examples.

Coupling Cycles

The coupling of standard Fmoc-aminoacids (10 or 20 mole equivalent) were performed via carboxyl activated with 2-(1H-benzotriazole-1-yl)-1,1,3,3-tetramethyluronium hexafluoro phosphate (HBTU, 10 or 20 mole equivalent), 1-hydroxybenzotriazole.hydrate (HOBT, 10 or 20 mole equivalent) and N-methylmorpholine (N, 20 or 40 mole equivalents) in dimethylformamide, with pre-activation for 5 minutes. Activated species were dispensed to the appropriate wells of a polypropylene 96-well plate (Beckman, 1 mL wells, 500 μL solution per well for crowns or 250 μL solution per well for gears) in a pattern required for synthesis. Loaded free amino Building Block-linker constructs (e.g.(11)) were added and the coupling reaction left overnight. Following overnight coupling, crowns/gears were taken through standard cycles washing and Fmoc deprotection (see Grabowska, U. et al). Identical activation and coupling conditions were used for the coupling of a range of carboxylic acids (R—COOH). Alternatively, chloroformates e.g. morpholine-4-carbonylchloride (10 mole equivalent), were coupled in DMF with the addition of NMM (10 mole equivalents).

Acidolytic Cleavage Cycle

A mixture of 95% TFA/5% water was pre-dispensed into two polystyrene 96-well plates (Beckman, 1 mL wells, 600 μL solution per well for crowns or 300 μL solution per well for gears) in a pattern corresponding to that of the synthesis. The completed multipin assembly was added to the first plate (mother plate), the block covered in tin foil and cleaved for 24 hours. The cleaved multipin assembly was then removed from the first plate and added to the second plate (washing plate) for 15 minutes. The spent multipin assembly was then discarded and the mother/washing plates evaporated on an HT-4 GeneVac plate evaporator.

ANALYSIS AND PURIFICATION OF CLEAVED EXAMPLES (a) Ex 1.21 μmole Gears. 100 μL dimethylsulphoxide (DMSO) was added to each post cleaved and dried washing plate well, thoroughly mixed, transferred to the corresponding post cleaved and dried mother plate well and again thoroughly mixed. 10 μL of this DMSO solution was diluted to 100 μL with a 90% acetonitrile/10% 0.1% aq TFA mixture. 20 μL aliquots were analysed by HPLC-MS and full analytical HPLC. In each case the crude example molecules gave the expected [M+H]+ ion and an HPLC peak at >80% (by 215 nm UV analysis). This provided an approximately 10 mM DMSO stock solution of good quality crude examples for preliminary protease inhibitory screening.

(b) Ex 10 μmole Crowns. 500 μL of a 90% acetonitrile/10% 0.1% aq TFA mixture was added to each washing plate well, thoroughly mixed, transferred to the corresponding mother plate well and again thoroughly mixed. 5 μL of this solution was diluted to 100 μL with a 90% acetonitrile/10% 0.1% aq TFA mixture. 20 μL aliquots were analysed by HPLC-MS and full analytical HPLC. In each case the crude example molecules gave the expected [M+H]+ ion and an HPLC peak at >80% (by 215 nm UV analysis). The polystyrene blocks containing crude examples were then lyophilized.

(c) Individual examples (ex (b)) were re-dissolved in a 1:1 mixture of 0.1% aq TFA/acetonitrile (1 mL) and purified by semi-preparative BHLC (Phenomenex Jupiter $C_4$, 5μ, 300 A, 250×10 mm, a 25–90% B in A gradient over 25 mins, 4.0 mL/min, 215 nm UV detection). Fractions were lyophilised into pre-tarred glass sample vials to provide purified examples (typically 2 to 4 mg, 40 to 80% yield).

(d) Purified examples were dissolved in an appropriate volume of DMSO to provide a 10 mM stock solution, for accurate protease inhibitory screening.

Example 1

(3aR, 6aR) 4-tert-Butyl-N-[2-(4-hydroxyphenyl)-1S-(3-oxo-hexahydrocyclopenta[b]furan-3a-ylcarbamoyl)-ethyl]benzamide

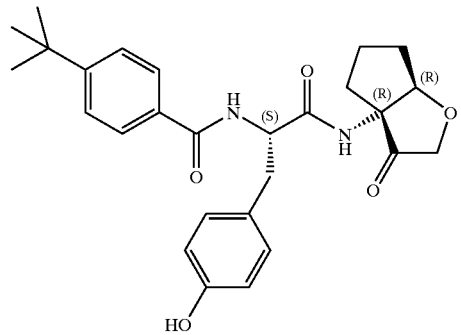

Following the general details from Scheme 1, the required bicycle building block (3aR, 6aR) (3-Oxo-hexahydrocyclopenta[b]furan-3a-yl) carbamic acid 9H-fluoren-9-ylmethyl ester (8) was prepared as follows.

(1) Preparation of (2S)-2-tert-Butoxycarbonylamino-3-phenylpropionic acid 2-oxo-cyclopentyl ester a) A solution of cyclopentanone (11.6 ml, 130 mmol) in methanol (250 ml) was added drop-wise at 0° C. over 20 minutes to a stirred solution of potassium hydroxide (85% tech., 22.1 g, 335 mmol) in methanol (75 ml). The mixture was stirred at 0° C. for 30 minutes then 2-iodosylbenzoic acid (36.45 g, 138 mmol) was added in portions over 1 hour. The mixture was allowed to warm to ambient temperature over 4 hours, then stirred at ambient temperature for 20 hours. The majority of solvent was removed in vacuo then the product was extracted into dichloromethane (400 ml), then the extracts were washed with water (2×250 ml), dried ($Na_2SO_4$) and the solvent removed in vacuo to leave 2,2-dimethoxycyclopentanol as a colourless oil (11.98 g) which was used without further purification.

b) 4-(Dimethylamino)pyridine (1.0 g, 8.2 mmol) was added at 0° C. to a stirred suspension of 2,2-dimethoxycyclopentanol (11.98 g, 82 mmol), (S)-2-tert-butyloxycarbonylamino-3-phenylpropionic acid (23.9 g, 90.3 mmol) and 1-[3-(dimethylamino)propyl]-3-ethylcarbodiimide hydrochloride (23.6 g, 123.1 mmol) in dichloromethane (500 ml). The mixture was stirred at 0° C. for 4 hours, then it was washed with water (2×300 ml) and saturated aqueous sodium chloride solution (200 ml), dried ($Na_2SO_4$) and the solvent removed in vacuo to leave (2S)-2-tert-butoxycarbonylamino-3-phenylpropionic acid 2,2-dimethoxy cyclopentyl ester as yellow oil (36.0 g) which was used without further purification.

c) 4-Toluenesulphonic acid monohydrate (1.7 g, 9.2 mmol) was added to a stirred solution of (2S)-2-tert-butoxycarbonylamino-3-phenylpropionic acid 2,2-dimethoxycyclopentyl ester (36 g, 91.6 mmol) in acetone (450 ml) at ambient temperature. The solution was stirred for 3 days then water (600 ml) and saturated aqueous sodium hydrogen carbonate solution (200 ml) were added, then the product was extracted into ethyl acetate (600 ml). The aqueous phase was extracted with ethyl acetate (2×400 ml), then the combined ethyl acetate solutions were washed with saturated aqueous sodium chloride solution (2×150 ml), dried ($Na_2SO_4$) and the solvent removed in vacua. The residue (18.05 g) was purified by flash chromatography over silica gel eluting with a gradient of heptane:ethyl acetate 3:1→2:1. Appropriate fractions were combined and the solvents removed in vacuo to leave (2S)-2-tert-butoxycarbonylamino-3-phenylpropionic acid 2-oxocyclopentyl ester as a colourless oil (18.05 g, 40% from cyclopentanone). TLC (single UV spot, Rf=0.25, heptane:ethyl acetate 7:3), analytical HPLC with main broad peak Rt=17.9–19.2 mins, HPLC-MS (main broad UV peak with Rt=9.04–9.24 mins, 248.1 [M−Boc+2H]+, 370.2 [M+Na]+, 717.3 [2M+Na]+).

$\delta$H (CDCl$_3$ at 298K); 1.42 (9H, 3×C$\underline{H}_3$, s), 1.79–2.48 (6H, 3×cyclopentyl C$\underline{H}_2$, m), 3.06–3.28 (2H, C$\underline{H}_2$Ph, m), 4.60–5.20 (3H, COC$\underline{H}$O+C$\underline{H}$N+N$\underline{H}$, m), 7.17–7.36 (5H, aromatic).

(2) Preparation of (4aS, 7aS) 3S-Benzyl-2-oxo-hexahydrocyclopenta[1,4]oxazine-4aS-carbonitrile

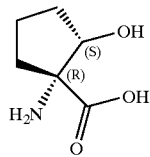

Trifluoroacetic acid (75 ml) was added drop-wise at 0° C. over 60 minutes to a stirred solution of (2S)-2-tert-butoxycarbonylamino-3-phenylpropionic acid 2-oxocyclopentyl ester (17.05 g, 49.1 mmol) in dichloromethane (250 ml). The mixture was stirred at 0° C. for 75 minutes then the majority of solvent was removed in vacuo. Toluene (75 ml) was added to the residue then the solvent was removed in vacuo to obtain an oil which was dissolved in acetonitrile (700 ml). Magnesium sulphate (29.5 g) then sodium acetate (20.1 g) were added to the stirred solution. The resulting suspension was stirred for 90 minutes then solids were removed by filtration, then solvents removed in vacuo. The residue was dissolved in propan-2-ol (650 ml) then stirred under nitrogen. Trimethylsilyl cyanide (13.1 ml, 98.4 mmol) was added drop-wise over 15 minutes then zinc chloride (49 ml, 1M solution in diethyl ether) was added over 40 minutes. The mixture was stirred for 18 hours then cautiously added to saturated aqueous sodium hydrogen carbonate solution (750 ml). The mixture was diluted with water (750 ml) then the product was extracted into diethyl ether (3×500 ml). The combined ethereal solutions were washed with saturated aqueous sodium chloride solution (350 ml), dried (MgSO$_4$) and the solvents removed in vacuo to obtain a brown oil (10.05 g) which was purified by flash chromatography over silica gel eluting with a gradient of heptane:ethyl acetate 4:1→3:2. Appropriate fractions were combined and the solvents removed in vacuo to leave (3S, 4aR, 7aS) 3-benzyl-2-oxohexahydrocyclopenta[1,4]oxazine-4a-carbonitrile as a white solid (4.54 g, 36%). TLC (single UV spot, Rf=0.45, heptane:ethyl acetate 3:1), analytical HPLC Rt=14.521 mins, HPLC-MS (single main UV peak with Rt=7.645 mins, 257.2 [M+H]+, 279 [M+Na]+).

$\delta$H (CDCl$_3$ at 298K); 1.70–2.29 (7H, 3×C$\underline{H}_2$+N$\underline{H}$, m), 2.84 (1H, C$\underline{H}_2$CHN, dd, J=14.3, 8.8 Hz), 3.52 (1H, C$\underline{H}_2$CHN, dd, J=14.3, 3.6 Hz), 3.90 (1H, CH$_2$C$\underline{H}$N, dd, J=9.8, 3.6 Hz), 4.74 (1H, C$\underline{H}$O, dd, J=6.8, 5 Hz), 7.15–7.32 (5H aromatic).

(3) Preparation of 1R-Amino-2S-hydroxycyclopentanecarboxylic acid

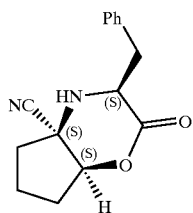

tert-Butylhypochlorite (4.0 ml, 35.4 mmol) was added drop-wise under nitrogen at 0° C. over 2 minutes to a stirred suspension of (3S, 4aR, 7aS) 3-benzyl-2-oxohexahydrocyclopenta[1,4]oxazine-4a-carbonitrile (4.53 g, 17.7 mmol) in diethyl ether (350 ml). The mixture was stirred at 0° C. for 140 minutes then triethylamine (7.4 ml, 53 mmol) was added drop-wise over 30 minutes. The resulting suspension was stirred at 0° C. for 3 hours then at ambient temperature for 23 hours. Insoluble materials were removed by filtration, then the filtrate was concentrated in vacuo. The residue was purified by flash chromatography over silica gel eluting with heptane:ethyl acetate (7:3). Appropriate fractions were combined and the solvents removed in vacuo to leave a white solid (3.3 g, TLC [single UV spot, Rf=0.3, heptane:ethyl acetate 2:1], analytical HPLC Rt=16.071 mins) which was cooled to 0° C. then concentrated hydrochloric acid at 0° C. was added in one portion. The suspension was allowed to warm to ambient temperature over 2 hours then stirred for 20 hours. The reaction mixture was partitioned equally between six pressure vessels that were sealed then heated at 100° C. for 26 hours then allowed to cool to ambient temperature. The reaction mixtures were recombined then the product extracted into water (400 ml) then washed with diethyl ether (2×200 ml) and the solvents removed in vacuo to leave a residue that was purified over Dowex 50WX4-200 ion exchange resin eluting consecutively with 0.01M hydrochloric acid, water and then 1.0M aqueous ammonium hydroxide solution. Appropriate fractions were combined and the solvents removed in vacuo to leave a solid which was freeze-dried from a mixture of water:acetonitrile (1:1) three times to obtain (1R, 2S) 1-amino-2-hydroxycyclopentanecarboxylic acid as a light brown solid (1.73 g, 67%). HPLC-MS (not UV active Rt=0.541 mins, 146.1 [M+H]+).

$\delta$H (D$_2$O at 298K); 1.50–1.90 (4H, 2×CH$_2$, m), 2.16–2.25 (2H, CH$_2$, m), 4.36 (1H, C$\underline{H}$OH, dd, J=8.3, 7.7 Hz).

$\delta$C (D$_2$O at 298K); 21.56 (d, CH$_2$C$\underline{H}_2$CH$_2$), 33.46 and 35.00 (both d, $\underline{CH}_2$CH$_2$$\underline{CH}_2$), 69.74 ($\underline{C}$NH2), 77.54 (u, $\underline{C}$HOH), 178.33 $\underline{C}$O$_2$H).

(4) Preparation of 1R-(9H-Fluoren-9-ylmethoxycarbonylamino)-2S-hydroxycyclo pentanecarboxylic acid (0.67 g, 4.6 mmol) was added at 0° C. to a stirred solution of sodium carbonate (1.0 g, 9.7 mmol) in water:1,4-dioxan (2:1, 45 ml). A solution of 9-fluorenylmethyl chloroformate (1.25 g, 4.85 mmol) in 1,4-dioxan (15 ml) was added drop-wise over 30 minutes. The resultant suspension was stirred for 75 minutes at 0° C. then at ambient temperature for 45 minutes. Water (200 ml) was added then the cloudy solution washed with chloroform (2×140 ml). Chloroform (100 ml) was added and the mixture acidified with 1M hydrochloric acid (pH ~2). The chloroform layer was separated then the aqueous layer re-extracted with chloroform (2×100 ml). The chloroform extracts which had been separated from the acidified aqueous layer were combined then dried (Na$_2$SO$_4$) and the solvent removed in vacuo to leave a colourless oil to which heptane (100 ml) was added before storing at −80° C. for 16 hours. The solvent was rapidly decanted from the oily residue which was washed with heptane (5 ml) then remaining solvents removed in vacuo to obtain (1R, 2S) 1-(9H-fluoren-9-ylmethoxycarbonylamino)-2-hydroxy cyclopentanecarboxylic acid as an oil (1.27 g, 75%). TLC (main UV spot, Rf=0.20, minor UV spot, Rf=0.15, 20% MeOH in CHCl₃), analytical HPLC Rt=17.172 mins (major), Rt=16.800 mins (minor) and HPLC-MS (main UV peak with Rt=7.840 mins, 368.1 [M+H]⁺, 390.1 [M+Na]⁺, minor UV peak with Rt=7.646 mins, 368.1 [M+H]⁺, 390.1 [M+Na]⁺).

δH (CDCl₃ at 298K); 1.60–2.16 (4H, C$\underline{H}_2$CH₂CH₂ and 1H, CH₂CH₂C$\underline{H}_2$, m), 2.35 (1H, CH₂CH₂C$\underline{H}_2$, m), 4.10 (1H, O$\underline{H}$, brs), 4.24 (1H, Fmoc H-9, m), 4.36–4.57 (3H, Fmoc C$\underline{H}_2$ and C$\underline{H}$OH, m), 5.93 (1H, N$\underline{H}$, s), 7.28–7.33 (2H aromatic, Fmoc H-2 and H-7), 7.34–7.41 (2H aromatic, Fmoc H-3 and H-6), 7.54–7.62 (2H aromatic, Fmoc H-1 and H-8), 7.72–7.79 (2H aromatic, Fmoc H-4 and H-5).

(5) Preparation of 1R-9H-Fluoren-9-ylmethoxycarbonylamino)-2S-hydroxycyclo pentanecarboxylic acid allyl ester

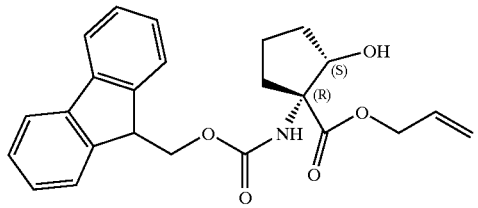

A solution of 1R-(9H-fluoren-9-ylmethoxycarbonylamino)-2S-hydroxy cyclopentanecarboxylic acid (1.75 g, 4.8 mmol) and tricaprylmethylammonium chloride (1.93 g, 4.8 mmol) in dichloromethane (14 ml) was added to a stirred solution of sodium hydrogen carbonate (0.4 g, 4.8 mmol) in water (14 ml), then allyl bromide (1.44 ml, 16.7 mmol) was added in one portion. The biphasic mixture was stirred for 20 hours then diluted with water (50 ml) and the product extracted into dichloromethane (2×50 ml). The combined organic layers were dried (MgSO₄) and the solvent removed in vacuo to obtain a colourless oil which was purified by flash chromatography over silica gel eluting with a gradient of heptane:ethyl acetate 10:3→20:7. Appropriate fractions were combined and the solvents removed in vacuo to leave (1R, 2S) 1-(9H-fluoren-9-ylmethoxycarbonylamino)-2-hydroxycyclopentanecarboxylic acid allyl ester as a colourless oil (1.32 g, 67%). TLC (single UV spot, Rf=0.25, heptane:ethyl acetate 3:1), analytical HPLC Rt=20.371 mins (major), Rt=19.706 min (minor) and HPLC-MS (main UV peak with Rt=9.412 mins, 408.1 [M+H]⁺, 430.1 [M+Na]⁺; minor UV peak with Rt=9.102 mins, 408.1 [M+H]⁺, 430.1 [M+Na]⁺).

δH (CDCl₃ at 298K); 1.6–2.63 (7H, C$\underline{H}_2$CH₂CH₂, O$\underline{H}$, m), 4.8–4.27 (1H, Fmoc H-9, m), 4.29–4.48 (3H, H-2 and Fmoc C$\underline{H}_2$, m), 4.57–4.66 (2H, C$\underline{H}_2$CH=CH₂, brs), 5.22 (1H, CH₂CH=C$\underline{H}_2$, dd, J=10.4, 1.0 Hz), 5.29 (1H, CH₂CH=C$\underline{H}_2$, d, J=13.6 Hz), 5.77 (1H, N$\underline{H}$, brs), 5.82–5.94 (1H, CH₂C$\underline{H}$=CH₂, m), 7.27–7.32 (2H aromatic, Fmoc H-2 and H-7), 7.36–7.41 (2H aromatic, Fmoc H-3 and H-6), 7.55–7.62 (2H aromatic, Fmoc H-1 and H-8), 7.74–7.77 (2H aromatic, Fmoc H-4 and H-5).

δC (CDCl₃ at 298K); 20.37 (d, CH₂$\underline{C}$H₂CH₂), 32.52/32.29 and 34.20 (both d, $\underline{C}$H₂CH₂$\underline{C}$H₂), 47.58/47.52 (u, Fmoc C-9), 66.53 (d, Fmoc $\underline{C}$H₂), 67.34 (d, $\underline{C}$H₂CH=CH₂), 76.0 (q, $\underline{C}$CO₂CH₂), $\underline{C}$HOH under CHCl₃?, 118.97 (d, $\underline{C}$H₂=CHCH₂), 120.39 (u, Fmoc C-4 and C-5), 125.49 (u, Fmoc C-1 and C-8), 127.45/127.46 (u, Fmoc C-2 and C-7), 128.09 (u, Fmoc C-3 and C-6), 132.09 (u, CH₂=$\underline{C}$HCH₂), 141.72 (q, Fmoc C-4' and C-5'), 144.20/144.33 (q, Fmoc C-1' and C-8'), 156.76 (q, O$\underline{C}$ON), 173.61 (q, $\underline{C}$O₂CH₂CH=CH₂).

(6) Preparation of 1R-(9H-Fluoren-9-ylmethoxycarbonylamino)-2-oxo-cyclo pentanecarboxylic acid allyl ester

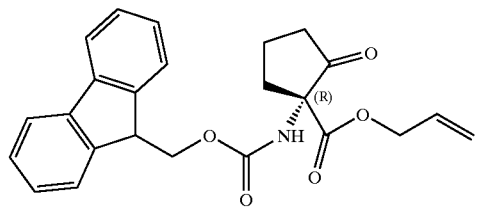

A solution of dimethyl sulphoxide (0.224 ml, 3.15 mmol) in dichloromethane (1.0 ml) was added under nitrogen to a stirred solution of oxalyl chloride (0.132 ml, 1.51 mmol) in dichloromethane (2.5 ml) at −70° C. over 20 minutes. The mixture was stirred for 10 minutes then a solution of (1R, 2S) 1-(9H-fluoren-9-ylmethoxycarbonylamino)-2-hydroxycyclopentanecarboxylic acid allyl ester (0.535 g, 1.3 mmol) in dichloromethane (3 ml) added over 20 minutes. The mixture was stirred for 10 minutes then triethylamine (0.92 ml, 6.57 mmol) added drop-wise over 5 minutes. The cooling bath was then removed and stirring continued for 45 minutes at ambient temperature. Saturated aqueous ammonium chloride solution (50 ml) was added then the product extracted into diethyl ether (2×50 ml). The combined ethereal layers were washed with water (25 ml), dried (MgSO₄) and the solvent was removed in vacuo to obtain a colourless oil (520 mg) which was purified by flash chromatography over silica gel eluting with heptane:ethyl acetate (3:1). Appropriate fractions were combined and the solvents removed in vacuo to leave (1R) 1-(9H-fluoren-9-ylmethoxycarbonylamino)-2-oxocyclopentane carboxylic acid allyl ester as a colourless oil (0.43 g, 81%). TLC (single UV spot, Rf=0.30, heptane:ethyl acetate 2:1), analytical HPLC with main peak Rt=19.993 mins, HPLC-MS (single UV peak with Rt=10.132 mins, 406.1 [M+H]⁺, 428.1 [M+Na]⁺).

δH (CDCl₃ at 298K); 2.15–2.23 (2H, CH₂C$\underline{H}_2$CH₂, m), 2.46–2.70 (4H, C$\underline{H}_2$CH₂C$\underline{H}_2$, m), 4.21 (1H, Fmoc H-9, t, J=7.1 Hz), 4.35 (2H, Fmoc C$\underline{H}_2$, d, J=7.1), 4.66 (2H, C$\underline{H}_2$CH=CH₂, brs), 5.26–5.35 (2H, CH₂CH=C$\underline{H}_2$, m), 5.80–5.91 (1H, CH₂C$\underline{H}$=CH₂, m), 6.14 (1H, N$\underline{H}$, brs), 7.27–7.35 (2H aromatic, Fmoc H-2 and H-7), 7.36–7.41 (2H aromatic, Fmoc H-3 and H-6), 7.54–7.60 (2H aromatic, Fmoc H-1 and H-8), 7.74–7.77 (2H aromatic, Fmoc H-4 and H-5).

δC (CDCl₃ at 298K); 19.19 (d, CH₂$\underline{C}$H₂CH₂), 34.53 and 36.87 (both d, $\underline{C}$H₂CH₂$\underline{C}$H₂), 47.42 (u, Fmoc C-9), 67.43 and 67.665 (both d, Fmoc $\underline{C}$H₂ and $\underline{C}$H₂CH=CH₂), 67.85 (q, $\underline{C}$CO₂CH₂), 119.92 (d, CH₂CH=$\underline{C}$H₂), 120.40 (u, Fmoc C-4 and C-5), 125.52 (u, Fmoc C-1 and C-8), 127.51 (u, Fmoc C-2 and C-7), 128.16 (u, Fmoc C-3 and C-6), 131.09 (u, CH₂=$\underline{C}$HCH₂), 141.68 (q, Fmoc C-4' and C-5'), 144.00/144.16 (q, Fmoc C-1' and C-8'), 155.25 (q, O$\underline{C}$ON), 169.25 (q, $\underline{C}$O₂CH₂CH=CH₂) 211.30 (q, $\underline{C}$OCH₂CH₂).

(7) Preparation of 1R-(9H-Fluoren-9-ylmethoxycarbonylamino)-2R-hydroxy cyclopentanecarboxylic acid allyl ester

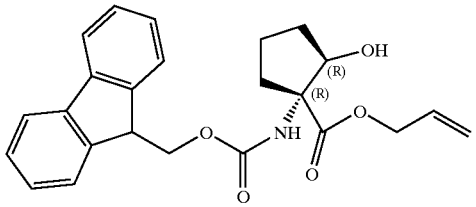

Sodium borohydride (39 mg, 1.04 mmol) was added to a stirred solution of 1R-(9H-fluoren-9-ylmethoxycarbonylamino)-2-oxocyclopentanecarboxylic acid allyl ester (0.42 g, 1.04 mmol) in methanol (6 ml) at 0° C. in one portion. The mixture was stirred for 10 min then solvents removed in vacua to leave a residue. Water (20 ml) and dichloromethane (20 ml) were added followed by 1M hydrochloric acid to acidify the mixture (pH ~1.5). The dichloromethane layer was collected then the aqueous layer extracted with dichloromethane (20 ml). The combined dichloromethane layers were washed with aqueous saturated sodium chloride solution (20 ml). The aqueous saturated sodium chloride solution was extracted with dichloromethane (10 ml) then the dichloromethane layers were combined then dried (MgSO$_4$) and the solvent removed in vacuo to obtain a colourless oil (420 mg) which was purified by flash chromatography over silica gel eluting with a gradient of heptane:ethyl acetate 7:3→13:7. Appropriate fractions were combined and the solvents removed in vacuo to leave 1R-(9H-fluoren-9-ylmethoxycarbonylamino)-2R-hydroxycyclopentane carboxylic acid allyl ester as a colourless oil (288 mg, 68%). TLC (single UV spot, Rf=0.25, heptane:ethyl acetate 3:1), analytical HPLC Rt=19.680 mins (major), Rt=20.323 min (minor) and HPLC-MS (main UV peak with Rt=9.076 mins, 408.1 [M+H]$^+$, 430.0 [M+Na]$^+$; minor UV peak with Rt=9.451 mins, 408.1 [M+H]$^+$, 430.0 [M+Na]$^+$). 4-Toluenesulphonic acid monohydrate (30 mg, 0.16 mmol) was added to a solution of the oil (230 mg) in toluene (12 ml) then the mixture heated at 100° C. for 75 minutes. Two further batches (170 mg and 35 mg) of the oil (prepared using the same procedure as above) were similarly treated with 4-toluenesulphonic acid monohydrate with appropriate scaling of quantities, then the three toluene mixtures were combined and solvents removed in vacuo to obtain a residue which was purified by flash chromatography over silica gel eluting with a gradient of heptane:ethyl acetate 7:3→13:7. Appropriate fractions were combined and the solvents removed in vacuo to leave (1R, 2R) 1-(9H-fluoren-9-ylmethoxycarbonylamino)-2-hydroxycyclopentanecarboxylic acid allyl ester as a colourless oil (380 mg). TLC (single UV spot, Rf=0.25, heptane:ethyl acetate 3:1), analytical HPLC single UV peak with Rt=18.141 mins and HPLC-MS (single UV peak with Rt=9.140 mins, 408.1 [M+H]$^+$, 430.1 [M+Na]$^+$).

$\delta$H (CDCl$_3$ at 298K); 1.72–2.44 (6H, C$\underline{H}_2$C$\underline{H}_2$CH$_2$, m), 4.12–4.19 (1H, H-2, m) 4.27 (1H, Fmoc H-9, t, J=6.5 Hz), 4.37–4.55 (3H, Fmoc C$\underline{H}_2$ and O$\underline{H}$, m), 4.60–4.75 (2H, C$\underline{H}_2$CH=CH$_2$, brs), 5.25 (1H, CH$_2$CH=C$\underline{H}_2$, d, J=10.5 Hz), 5.30–5.39 (2H, CH$_2$CH=C$\underline{H}_2$ and N$\underline{H}$, m), 5.83–5.96 (1H, CH$_2$C$\underline{H}$=CH$_2$, m), 7.29–7.35 (2H aromatic, Fmoc H-2 and H-7), 7.39–7.44 (2H aromatic, Fmoc H-3 and H-6), 7.58–7.65 (2H aromatic, Fmoc H-1 and H-8), 7.77–7.80 (2H aromatic, Fmoc H-4 and H-5).

$\delta$C (CDCl$_3$ at 298K); 20.92 (d, CH$_2$$\underline{C}$H$_2$CH$_2$), 32.46 and 35.63 (both d, $\underline{C}$H$_2$CH$_2$CH$_2$), 47.52 (u, Fmoc C-9), 66.55 and 67.37 (both d, Fmoc $\underline{C}$H$_2$ and $\underline{C}$H$_2$CH=CH$_2$), 69.43 (q, $\underline{C}$CO$_2$CH$_2$), 80.50 (u, $\underline{C}$HOH), 118.98 (d, $\underline{C}$H$_2$=CHCH$_2$), 120.43 (u, Fmoc C-4 and C-5), 125.41 (u, Fmoc C-1 and C-8), 127.47/127.49 (u, Fmoc C-2 and C-7), 128.14/128.16 (u, Fmoc C-3 and C-6), 132.08 (u, CH$_2$=$\underline{C}$HCH$_2$), 141.73 (q, Fmoc C-4' and C-5'), 144.00/144.23 (q, Fmoc C-1' and C-8'), 156.86 (q, O$\underline{C}$ON), 172.99 (q, $\underline{C}$O$_2$CH$_2$CH=CH$_2$).

(8) Preparation of 2R-tert-Butoxy-1R-(9H-Fluoren-9-ylmethoxycarbonylamino) cyclopentanecarboxylic acid allyl ester

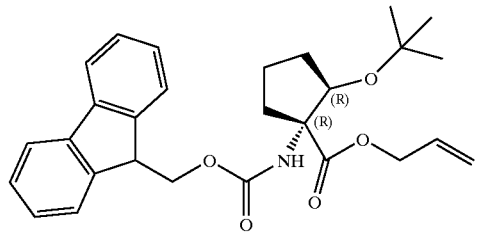

A stirred solution of 1R-(9H-fluoren-9-ylmethoxycarbonylamino)-2R-hydroxy cyclopentanecarboxylic acid allyl ester (360 mg, 0.88 mmol) in dichloromethane (5 ml) was cooled in a sealed pressure vessel to −70° C. then isobutylene gas (~3 ml) condensed into the solution. Concentrated sulphuric acid (25 µl) was added then the pressure vessel sealed. The mixture was stirred at ambient temperature for 20 hours then cooled to −70° C. N-Methylmorpholine (50 µl) was added then the unsealed pressure vessel allowed to warm to ambient temperature. The mixture was diluted with saturated aqueous sodium hydrogen carbonate solution (50 ml) and water (25 ml) then the product extracted into dichloromethane (50 ml then 2×25 ml). The combined dichloromethane layers were washed with saturated aqueous sodium chloride solution (25 ml), dried (Na$_2$SO$_4$) and the solvent removed in vacuo. The residue (370 mg) was purified by flash chromatography over silica gel eluting with a gradient of heptane:ethyl acetate 4:1→7:3. Appropriate fractions were combined and the solvents removed in vacuo to leave 2R-tert-butoxy-1R-(9H-fluoren-9-ylmethoxycarbonylamino) cyclopentanecarboxylic acid allyl ester as a colourless oil (305 mg, 75%). TLC (single UV spot, Rf=0.50, heptane:ethyl acetate 2:1), analytical HPLC Rt=22.623 mins and HPLC-MS (single UV peak with Rt=11.611 mins, 408.1 [M−$^t$Bu+2H]$^+$, 486.1 [M+Na]$^+$).

$\delta$H (CDCl$_3$ at 298K); 1.06 (9H, $^t$Bu, s), 1.80–2.41 (6H, C$\underline{H}_2$CH$_2$C$\underline{H}_2$, m), 4.21 (1H, Fmoc H-9, t, J=6.8 Hz), 4.26–4.50 (3H, Fmoc C$\underline{H}_2$ and H-2, m), 4.58–4.74 (1H, C$\underline{H}_2$CH=CH$_2$, brs), 5.21 (1H, CH$_2$CH=C$\underline{H}_2$, d, J=10.4 Hz), 5.35 (1H, CH$_2$CH=C$\underline{H}_2$, d, J=17.2 Hz), 5.84–6.01 (2H, CH$_2$C$\underline{H}$=CH$_2$ and N$\underline{H}$, m), 7.26–7.30 (2H aromatic, Fmoc H-2 and H-7), 7.37–7.39 (2H aromatic, Fmoc H-3 and H-6), 7.57–7.61 (2H aromatic, Fmoc H-1 and H-8), 7.70–7.77 (2H aromatic, Fmoc H-4 and H-5).

$\delta$C (CDCl$_3$ at 298K); 21.69/21.47 (d, CH$_2$$\underline{C}$H$_2$CH$_2$), 32.98 and 33.82 (both d, $\underline{C}$H$_2$CH$_2$$\underline{C}$H$_2$), 47.63 (u, Fmoc C-9), 66.54 and 66.89 (both d, Fmoc $\underline{C}$H$_2$ and $\underline{C}$H$_2$CH=CH$_2$), 70.07 and 74.03 (both q, $\underline{C}$CO$_2$CH$_2$ and O$\underline{C}$Me$_3$), 79.51 (u, $\underline{C}$HOCMe$_3$), 118.53 (d, $\underline{C}$H$_2$=CHCH$_2$), 120.38 (u, Fmoc C-4 and C-5), 125.46 (u, Fmoc C-1 and C-8), 127.46 (u, Fmoc C-2 and C-7), 128.07 (u, Fmoc C-3 and C-6), 132.40 (u, CH$_2$=$\underline{C}$HCH$_2$), 141.70 (q, Fmoc C-4' and C-5'), 144.32 (q, Fmoc C-1' and C-8'), 155.13 (q, O$\underline{C}$ON), 173.00 (q, $\underline{C}$O$_2$CH$_2$CH=CH$_2$).

(9) Preparation of 2R-tert-Butoxy-1R-(9H-Fluoren-9-ylmethoxycarbonylamino) cyclopentanecarboxylic acid

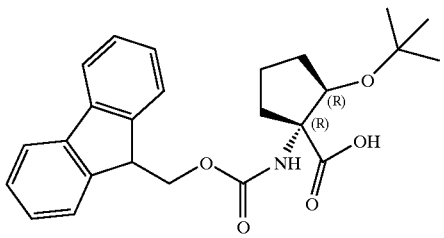

Tetrakistriphenylphosphine palladium(0) (15 mg, 0.013 mmol), dichloromethane (5 ml) then phenyltrihydrosilane (153 µl, 1.24 mmol) were added consecutively to 2R-tert-butoxy-1R-(9H-fluoren-9-ylmethoxy carbonylamino) cyclopentane carboxylic acid allyl ester (288 mg, 0.62 mmol) under nitrogen. The mixture was stirred for 45 minutes then 0.01M hydrochloric acid (30 ml) added and the product extracted into chloroform (1×20 ml then 1×10 ml). The combined chloroform layers were dried ($Na_2SO_4$) and the solvent removed in vacuo. The residue (460 mg) was purified by flash chromatography over silica gel eluting with a gradient of heptane:ethyl acetate 2:1→1:3. Appropriate fractions were combined and the solvents removed in vacuo to leave 2R-tert-butoxy-1R-(9H-fluoren-9-ylmethoxycarbonylamino)cyclopentanecarboxylic acid as a colourless oil (205 mg, 78%). TLC (single UV spot, Rf=0.25, heptane:ethyl acetate 1:2), analytical HPLC Rt=19.539 mins and HPLC-MS (single UV peak with Rt=9.850 mins, 368.1 [M-$^t$Bu+2H]$^+$, 446.1 [M+Na]$^+$).

$\delta$H (CDCl$_3$ at 298K); 1.22 (9H, $^t$Bu, s), 1.77–2.37 (6H, C H$_2$CH$_2$CH$_2$, m), 4.22 (1H, Fmoc H-9, t, J=6.8 Hz), 4.27–4.36 (2H, Fmoc CH$_2$, m), 4.65 (1H, H-2, brs), 5.39 (1H, NH, brs), 7.27–7.35 (2H aromatic, Fmoc H-2 and H-7), 7.36–7.41 (2H aromatic, Fmoc H-3 and H-6), 7.56–7.61 (2H aromatic, Fmoc H-1 and H-8), 7.73–7.76 (2H aromatic, Fmoc H-4 and H-5).

$\delta$C (CDCl$_3$ at 298K); 21.48 (d, CH$_2$CH$_2$CH$_2$), 33.70 and 35.31 (both d, CH$_2$CH$_2$CH$_2$), 47.56 (u, Fmoc C-9), 67.22 (d, Fmoc CH$_2$), 68.77 (q, CCO$_2$CH$_2$ or OCMe$_3$ other peak under chloroform?), 78.58 (u, CHOCMe$_3$), 120.37 (u, Fmoc C-4 and C-5), 125.54 (u, Fmoc C-1 and C-8), 127.47 (u, Fmoc C-2 and C-7), 128.09/128.12 (u, Fmoc C-3 and C-6), 141.69/141.73 (q, Fmoc C-4' and C-5'), 144.02/144.38 (q, Fmoc C-1' and C-8'), 156.05 (q, OCON), 174.89 (q, CO$_2$H).

(10) Preparation of (2R-tert-Butoxy-1R-fluorocarbonyl-cyclopentyl)carbamic acid 9H-fluoren-9-ylmethyl ester

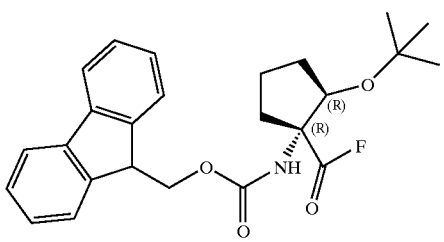

Pyridine (53 µl, 0.66 mmol) then cyanuric fluoride (71 µl, 0.85 mmol) were added consecutively at 0° C. to a stirred solution of 2R-tert-butoxy-1R-(9H-fluoren-9-ylmethoxycarbonylamino)cyclopentanecarboxylic acid (159 mg, 0.38 mmol) in dichloromethane (5 ml) under nitrogen. The suspension was stirred for 30 minutes at 0° C. then for 5 hours at ambient temperature. Crushed ice (~10 ml) and ice-chilled water (10 ml) was added, then the product was extracted into dichloromethane (20 ml). The dichloromethane layer was dried (MgSO$_4$) and the solvent removed in vacuo to give (2R-tert-butoxy-1R-fluorocarbonylcyclopentyl)carbamic acid 9H-fluoren-9-ylmethyl ester as a pale brown oil (115 mg, 71%) which was used without further purification. TLC (single UV spot, Rf=0.45, heptane:ethyl acetate 2:1), analytical HPLC main UV peak with Rt=23.933 mins and HPLC-MS (main UV peak with Rt=11.439 mins, 370.1 [M-$^t$Bu+2H]$^+$, 448.1 [M+Na]$^+$).

(11) Preparation of (3aR, 6aR) (3-Oxo-hexahydrocyclopenta [b]furan-3a-yl)carbamic acid 9H-fluoren-9-ylmethyl ester

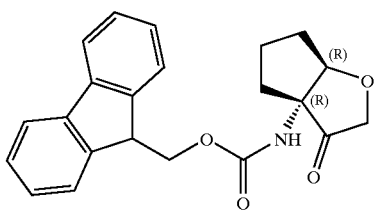

a) Ethereal diazomethane [generated from diazald (0.94 g, ~3 mmol) addition in diethyl ether (15 ml) to sodium hydroxide (1.05 g) in water (1.5 ml)/ethanol (3.0 ml) at 60° C.] was added to a stirred solution of (1R, 2R) (2-tert-butoxy-1-fluorocarbonylcyclopentyl)carbamic acid 9H-fluoren-9-ylmethyl ester (115 mg, 0.27 mmol) in dichloromethane (2 ml) at 0° C. The solution was stirred for 20 minutes at ° C. then at ambient temperature for 20 hours. Acetic acid (0.6 ml, 10.5 mmol) was added then the solution was stirred for 5 minutes before adding tert-butyl methyl ether (50 ml). The ethereal layer was washed with saturated aqueous sodium hydrogen carbonate solution (40 ml) then water (2×30 ml), then dried (Na$_2$SO$_4$) and the solvent removed in vacuo. The residue (130 mg) was purified by flash chromatography over silica gel eluting with a gradient of heptane:ethyl acetate 4:1→1:3. Appropriate fractions were combined and the solvents removed in vacuo to leave [2R-tert-butoxy-1R-(2-diazoacetyl) cyclopentyl]carbamic acid 9H-fluoren-9-ylmethyl ester (16 mg) as an oil which was used without further purification.

b) A solution of lithium chloride (15 mg, 0.36 mmol) in acetic acid:water (4:1, 1.0 ml) was added to [2R-tert-butoxy-1R-(2-diazoacetyl)cyclopentyl]carbamic acid 9H-fluoren-9-ylmethyl ester (16 mg). The solution was stirred for 2.5 hours then chloroform (25 ml) and saturated aqueous sodium hydrogen carbonate solution (25 ml) was added. The chloroform layer washed with saturated aqueous sodium hydrogen carbonate solution (25 ml), saturated aqueous sodium chloride solution (25 ml), dried (Na$_2$SO$_4$) and the solvent removed in vacuo. The residue (16 mg) was purified by flash chromatography over silica gel eluting with a gradient of heptane:ethyl acetate 31:9→3:1. Appropriate fractions were combined and the solvents removed in vacuo to leave (3aR, 6aR) (3-oxohexahydrocyclopenta[b]furan-3a-yl)carbamic acid 9H-fluoren-9-ylmethyl ester (11.0 mg) as a white solid. TLC (single UV spot, Rf=0.3, heptane:ethyl acetate 2:1), analytical HPLC main UV peak with Rt=18.872 mins and HPLC-MS (main UV peak with Rt=9.208 mins, 364.0 [M+H]$^+$, 386.0 [M+Na]$^+$).

$\delta$H (CDCl$_3$ at 298K); 1.55–2.19 (6H, CH$_2$CH$_2$CH$_2$, m), 4.15 (1H, H-2, d, J=16.8 Hz), 4.19 (1H, Fmoc H-9, t, J=6.7 Hz), 4.31 (1H, H-2, d, J=16.8 Hz), 4.36–4.44 (2H, Fmoc C H$_2$, m), 4.74 and 4.97 (each 1H, H-6a and NH, brs), 7.29–7.36 (2H aromatic, Fmoc H-2 and H-7), 7.38–7.44 (2H aromatic, Fmoc H-3 and H-6), 7.53–7.61 (2H aromatic, Fmoc H-1 and H-8), 7.74–7.80 (2H aromatic, Fmoc H-4 and H-5).

δC (CDCl$_3$ at 298K); 24 (CH$_2$CH$_2$CH$_2$), 33 and 37 (CH$_2$CH$_2$CH$_2$), 48 (u, Fmoc C-9), 68 (Fmoc CH$_2$), 70 (C-3a), 72 (d, C-2), 87 (u, C-6a), 120 (u, Fmoc C-4 and C-5), 125 (u, Fmoc C-1 and C-8), 127 (u, Fmoc C-2 and C-7), 128 (u, Fmoc C-3 and C-6), 142 (Fmoc C-4' and C-5'), 144 (Fmoc C-1' and C-8'), 156 (OCON), 215 (C-3).

Following the general details from Scheme 2, the required bicycle building block (3aR, 6aR) (3-Oxo-hexahydrocyclopenta[b]furan-3a-yl) carbamic acid 9H-fluoren-9-ylmethyl ester (8) was converted to building block-linker construct (10) as follows:

(3aR, 6aR) (3-Oxo-hexahydrocyclopenta[b]furan-3a-yl) carbamic acid 9H-fluoren-9-ylmethyl ester (8) (26.0 mg, 0.072 mmole) was dissolved in a mixture of ethanol (1.75 mL) and water (0.25 mL) containing sodium acetate.trihydrate (14.6 mg, 0.107 mmole, 1.5 eq). 4-[[(hydrazinocarbonyl)amino] methyl] cyclohexanecarboxylic acid.trifluoroacetate (23.6 mg, 0.072 mmole, 1.0 eq, Murphy, A. M. et al, *J. Am. Chem. Soc.*, 114, 3156–3157, 1992) was added and the mixture refluxed for 24 hr. Chloroform (35 mL) was added and the organics washed with HCl (2×15 mL, ~pH3), then brine (1×15 mL), dried (Na$_2$SO$_4$) and reduced in vacuo to provide crude building block-linker construct (10) as a colourless gum, yield 40.8 mg, analytical HPLC 2 product peaks Rt=17.57 and 18.08 mins (cis/trans geometrical isomers), HPLC-MS (2×UV peak, both with 561 [M+H]$^+$, 1121 [2M+Na]$^+$). Crude (10) was used directly for construct loading.

Following the general details from Scheme 2, the required building block-linker construct (10) was attached to the solid phase providing loaded building block-linker construct (11) as follows:

Building block-linker construct (10) (0.066 mmole), 2-(1H-benzotriazole-1-yl)-1,1,3,3-tetramethyluroniumhexafluorophosphate (HBTU, 25.0 mg, 0.066 mmole), 1-hydroxybenzotriazole.hydrate and (HOBT, 10.1 mg, 0.066 mmole) were dissolved in dimethylformamide (2 mL) and N-methylmorpholine (NMM, 14.4 μL, 0.13 mmole) added. After pre-activation for 5 minutes, free amine gears (20×1.2 μmole) were added, followed by dimethylformamide (0.5 mL) and left overnight. The spent coupling solution was then added to free amine crowns (2×10 μmole) and left overnight. Standard washing and analyses indicated loading at 87%.

Following the general details from Scheme 2, the required loaded building block-linker construct (11) was elaborated on the solid phase as follows:

Loaded construct (11) was elaborated to EXAMPLE 1 (3aR, 6aR) 4-tert-Butyl-N-[2-(4-hydroxyphenyl)-1S-(3-oxo-hexahydrocyclopenta[b]furan-3a-ylcarbamoyl) ethyl]benzamide by standard Fmoc deprotection and sequential coupling with Fmoc-Tyr(OBut)-OH then 4-tert-butylbenzoic acid. The crude example was cleaved and analysed (see general techniques). HPLC Rt=17.99 mins (>90%/), HPLC-MS 465.2 [M+H]$^+$, 951.4 [2M+Na]$^+$.

The following examples (2–12) were prepared as detailed for EXAMPLE 1, coupling with the required reagents to provide the full length molecule.

Example 2

(3aR, 6aR) Biphenyl-4-carboxylic acid [2-(4-hydroxyphenyl)-1S-(3-oxo-hexahydrocyclopenta[b] furan-3a-ylcarbamoyl) ethyl]amide

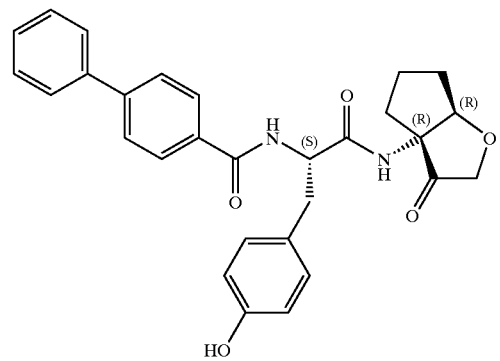

HPLC Rt=17.43 mins (>95%), HPLC-MS 485.2 [M+H]$^+$.

Example 3

(3aR, 6aR) Naphthalene-1-carboxylic acid [2-(4-hydroxyphenyl)-1S-(3-oxo-hexahydrocyclopenta[b] furan-3a-ylcarbamoyl) ethyl]amide

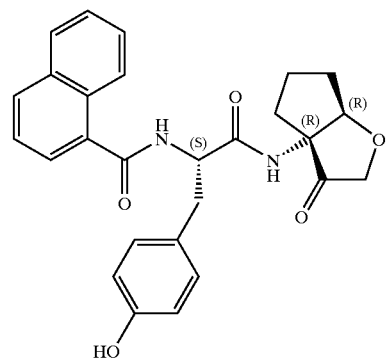

HPLC Rt=15.195 mins (>95)%, HPLC-MS 459.2 [M+H]$^+$.

Example 4

(3aR, 6aR) 4-tert-Butyl-N-[3-methyl-1S-(3-oxo-hexahydrocyclo penta[b]furan-3a-ylcarbamoyl) butyl]benzamide

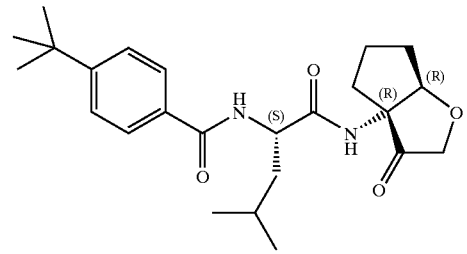

HPLC Rt=20.158 mins (>80%), HPLC-MS 415.1 [M+H]$^+$, 851.3 [2M+Na]$^+$.

Example 5

3aR, 6aR) Biphenyl-4-carboxylic acid-[3-methyl-1S-(3-oxo-hexa hydrocyclopenta[b]furan-3a-ylcarbamoyl) butyl]benzamide

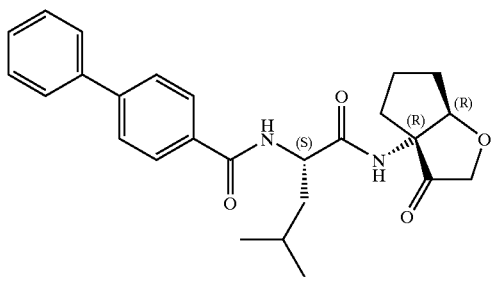

HPLC Rt=19.53 mins (>85%), HPLC-MS 435.2 [M+H]$^+$, 891.4 [2M+Na]$^+$.

Example 6

(3aR, 6aR) Benzo[b]thiophene-2-carboxylic acid [3-methyl-1S-(3-oxo-hexahydrocyclopenta[b]furan-3a-ylcarbamoyl) butyl]amide

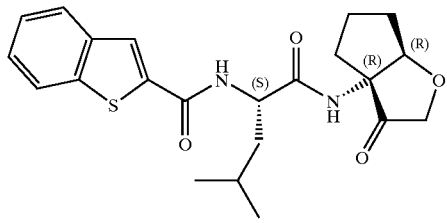

HPLC Rt=18.36 mins (>80%), HPLC-MS 415.1 [M+H]$^+$, 851.3 [2M+Na]$^+$.

Example 7

(3aR, 6aR) Thiophene-3-carboxylic acid [2-cyclohexyl-1S-(3-oxo-hexahydrocyclopenta[b]furan-3a-ylcarbamoyl) ethyl]amide

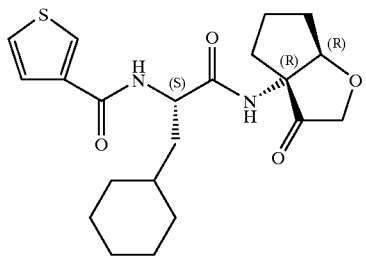

HPLC Rt=17.79 mins (>85%), HPLC-MS 405.2 [M+H]$^+$, 831.3 [2M+Na]$^+$.

Example 8

2RS, 3aR, 6aR) 2-Benzyloxy-3-cyclohexyl-N-(3-oxo-hexahydro cyclopenta[b]furan-3a-yl) propionamide

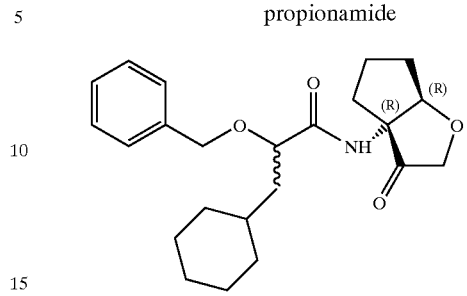

HPLC Rt=21.77–21.97 mins (>90%), HPLC-MS 386.3 [M+H]$^+$ (a) Preparation of 3-Cyclohexyl-2S-hydroxypropionic acid (Compound (14) Scheme 4)

A solution of sodium nitrite (12.1 g, 175 mmol) in water (40 ml) was added dropwise to a stirred suspension of (S)-α-aminocyclohexanepropionic acid hydrate (5 g, 26.5 mmol) in 0.5M sulphuric acid (120 ml, 60 mmol) at 0° C. over 1.5 hours. The mixture was allowed to warm to ambient temperature over 20 hours. The product was extracted into diethyl ether (2×25 ml) then the ethereal layers were washed with saturated aqueous sodium chloride solution (2×25 ml), dried (Na$_2$SO$_4$) and the solvents removed in vacuo. The residue (5.3 g) was recrystallized from diethyl ether (10 ml) and heptane (25 ml) to give 3-cyclohexyl-2S-hydroxypropionic acid as a white solid, yield 2.4 g, (53%).

$\delta_H$ (400 MHz, CDCl$_3$ at 298K), 0.89–1.35 (5H, m) and 1.51–1.86 (7H, m) (OCHCH$_2$ and cyclohexyl), 4.32 (1H, OCHCH$_2$, m)

(b) Preparation of 2RS-Benzyloxy-3-cyclohexylpropionic acid (Compound (15) Scheme 4)

Sodium hydride (265 mg of 60% dispersion in oil, 6.6 mmol) was added in two portions to a stirred mixture of 3-cyclohexyl-2S-hydroxypropionic acid (0.52 g, 3.0 mmol), dimethylformamide (5 ml) and dichloromethane (5 ml) at 0° C. over 5 minutes. The mixture was stirred at 0° C. for 5 minutes then at ambient temperature for 45 minutes. Benzyl bromide (0.45 ml, 3.8 mmol) was added then the mixture stirred for 1 hour before adding dimethylformamide (5 ml). After stirring for 4 hours potassium iodide (50 mg, 0.3 mmol) was added. The mixture was stirred for 20 hours then heated at 55° C. for 1 hour then allowed to cool to ambient temperature and poured into water (15 ml). A saturated aqueous sodium chloride solution (5 ml) was added then the mixture was extracted with dichloromethane (5 ml then 10 ml) that was discarded. The aqueous layer was acidified using 1M hydrochloric acid (10 ml) then extracted with dichloromethane (2×10 ml). The dichloromethane layer was dried (MgSO$_4$) and the solvent removed in vacuo. The residue (0.55 g) was dissolved in dimethylformamide (8 ml) then cooled to 0° C. before adding sodium hydride (190 mg of 60% dispersion in oil, 4.75 mmol). The mixture was stirred for 30 minutes then polymer bound isocyanate (380 mg, 2 mmolNg$^{-1}$) added. The mixture was stirred for 2 hours at ambient temperature then poured into water (15 ml). 1M Hydrochloric acid (10 ml) was added then the product was extracted into dichloromethane (2×10 ml), dried (Na$_2$SO$_4$) and the solvent removed in vacuo. The residue was purified by flash chromatography over silica gel eluting with a gradient of methanol:dichloromethane 0:1→1:20.

Appropriate fractions were combined and the solvents removed in vacuo to give 2RS-benzyloxy-3-cyclohexylpropionic acid as a colourless oil, yield 41 mg (5.2%).

HPLC-MS (single main UV peak with Rt=9.47 mins, 261.2 [M–H]⁻, 285.2[M+Na]⁺, 547.3[2M+Na]⁺).

$\delta_H$ (400 MHz, CDCl$_3$ at 298K), 0.72–1.03 (2H, cyclohexane, m), 1.08–1.38 (3H, cyclohexane, m), 1.45–1.93 (6H+2Hβ, cyclohexane, m), 3.93–4.18 (1Hα, OCHCO), 4.35–4.53 (1H, CH$_2$O, d, J=11.52 Hz), 4.68–4.88 (1H CH$_2$O, d, J=11.54 Hz), 7.20–7.47 (5H, ArH, m), 9.36 (1H, OH, brs).

Compound (15) was coupled under standard conditions to loaded building block-linker construct (11) (following standard removal of Fmoc), then cleaved to provide EXAMPLE 8.

Example 9

(3aR, 6aR) 2-(4-tert-Butyl-benzylsulfanyl)-4-methyl-pentanoic acid (3-oxo-hexahydrocyclopenta[b]furan-3a-yl)amide

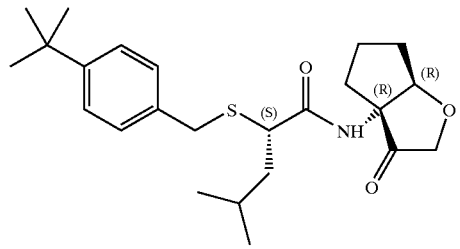

HPLC Rt=23.67 mins (>80%), HPLC-MS 418.3 [M+H]⁺.

(a) Preparation of 2R-Bromo-4-methylpentanoic acid (Compound (17), Scheme 5)

A solution of sodium nitrite (5.1 g, 73 mmol) in water (15 ml) was added drop-wise at 0° C. over 5 hours to a stirred mixture of D-leucine (8.75 g, 67 mmol), potassium bromide (29.75 g, 0.25 mol) and concentrated sulphuric acid (8.6 ml) in water (100 ml). The mixture was stirred for 30 minutes at 0° C. then at ambient temperature for 20 hours. The product was extracted into diethyl ether (2×150 ml) then the combined ethereal layers were washed with saturated aqueous sodium chloride solution (2×100 ml), dried (MgSO$_4$) and the solvent removed in vacuo. The residue was purified by flash chromatography over silica gel eluting with a gradient of methanol:dichloromethane 1:50→1:20. Appropriate fractions were combined and the solvents removed in vacuo to leave 2R-bromo-4-methylpentanoic acid (17) as a colourless oil, yield 1.60 g, (12.3%). TLC (single spot, Rf=0.2, methanol:dichloromethane 1:20). Additionally, a second crop (5.2 g, 40%) of slightly impure product was obtained $\delta_H$ (400 MHz, CDCl$_3$ at 298K), 0.95 and 0.99 (both 3H, CH$_3$CH, d, J=6.55 Hz), 1.77–1.89 (1H, CH$_3$CH, m), 1.93 (2Hβ, m), 4.31 (1Hα, t, J=7.7 Hz), 9.3 (1H, CO$_2$H, brs).

(b) Preparation of 2S-(4-tert-butylbenzylsulfanyl)-4-methylpentanoic acid (Compound (19), Scheme 5)

A solution of 2R-bromo-4-methylpentanoic acid (compound (17), 1.1 g, 5.6 mmol) and (4-(tert-butyl)phenyl)methanethiol (1.0 g, 5.6 mmol) in dimethylformamide (15 ml) was purged with nitrogen for 5 minutes then cooled to 0° C. Triethylamine (0.79 ml, 5.7 mmol) was added drop-wise over 1 minute then the mixture was stirred for two days at ambient temperature. The solvents were removed in vacuo and residue purified by flash chromatography over silica gel eluting with a gradient of methanol:dichloromethane 0:1→1:20. Appropriate fractions were combined and the solvents removed in vacuo to leave a residue which was purified by flash chromatography over silica gel eluting with ethyl acetate:heptane 2:5. Appropriate fractions were combined and the solvents removed in vacuo to give 2S-(4-tert-butylbenzylsulfanyl)-4-methylpentanoic acid (19) as a colourless oil, yield 150 mg, (9%). TLC (single spot, Rf=0.2, heptane:ethyl acetate 5:2), analytical HPLC with main peak Rt=22.117 mins, HPLC-MS (main UV peak with Rt=11.072 mins, 317.2 [M+Na]⁺).

$\delta_H$ (400 MHz, CDCl$_3$ at 298K), 0.70 and 0.85 (both 3H, CH$_3$CH, d, J=6.3), 1.29 (9H, (CH$_3$)$_3$C, s), 1.44–1.51 (1H, CH$_3$CH, m), 1.62–1.75 (2Hβ, m), 3.15–3.20 (1Hα, m), 3.81 and 3.88 (both 1H, SCH$_2$, d, J=13.2 Hz), 7.25–7.35 (4H, aromatic).

Compound (19) was coupled under standard conditions to loaded building block-linker construct (11) (following standard removal of Fmoc), then cleaved to provide EXAMPLE 9.

Example 10

(3aR, 6aR) 2-(4-tert-Butyl-phenylmethanesulfonyl)-4-methyl-pentanoic acid (3-oxo-hexahydrocyclopenta[b]furan-3a-yl)-amide

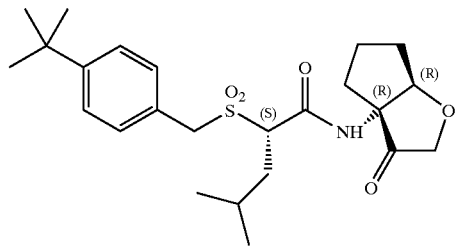

HPLC Rt=21.86 mins (>80%), HPLC-MS 450.2 [M+H]⁺.

Scheme 9. Compound (19) was coupled under standard conditions to loaded building block-linker construct (11). (following standard removal of Fmoc). The intermediate loaded thioether (1.2 μmole gear) was oxidised with m-chloroperbenzoic acid (5 eq, 65% reagent, 1.6 mg) in dichloromethane (200 μL) for 5 hrs, followed by standard washing and then cleaved to provide EXAMPLE 10.

Example 11

(3aR, 6aR) 2-Cyclohexylethyl-4-morpholinyl-4-oxo-N-(3-oxo-hexahydro-cyclopenta[b]furan-3a-yl)-butyramide

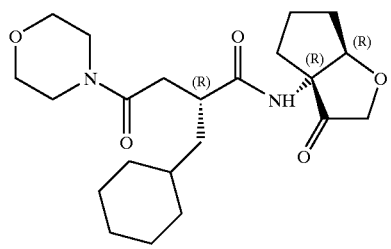

HPLC-MS 407.1 [M+H]⁺, 835.1 [2M+Na]⁺

(a) Preparation of 2R-cyclohexylmethyl-4-morpholin-4-yl-4-oxo-butyric acid methyl ester.

1-(3-dimethylaminopropyl)-3-ethylcarbodiimide.HCl (1.12 g, 5.69 mmol) then 1-hydroxybenzotriazole monohydrate (0.87 g, 5.69 mmol) were added to a stirred solution of 2R-(cyclohexylmethyl)succinic acid 1-methyl ester (compound (24), 1.0 g, 4.38 mmol) in dimethylformamide (10 ml) at 0° C. under argon. The mixture was stirred for 25 minutes then morpholine (0.7 ml, 8.76 mmol) was added drop-wise over 1 minute and stirring continued at ambient temperature for 16 hours. The product was extracted into ethyl acetate (200 ml) then washed with 1.0M hydrochloric acid (3×100 ml), saturated aqueous sodium hydrogen carbonate solution (3×100 ml), water (100 ml), then saturated aqueous sodium chloride solution (100 ml), dried (MgSO$_4$), and the solvent removed in vacuo to give 2R-cyclohexylmethyl-4-morpholin-4-yl-4-oxo-butyric acid methyl ester as an off-white solid, yield 1.22 g, (94%). HPLC-MS (single peak with Rt=7.91 mins, 298.1 [M+H]$^+$, 617.3 [2M+Na]$^+$).

(b) Preparation of 2R-cyclohexylmethyl-4-morpholin-4-yl-4-oxo-butyric acid (Compound (25), Scheme 7).

A solution of lithium hydroxide monohydrate (0.51 g, 12.18 mmol) in water (27 ml) was added a stirred solution of 2R-cyclohexylmethyl-4-morpholin-4-yl-4-oxo-butyric acid methyl ester (1.21 g, 4.06 mmol) in tetrahydrofuran (55 ml) and methanol (27 ml) at 0° C. The mixture was stirred at ambient temperature for 1 hours then diluted with water (100 ml). The aqueous layer was extracted with diethyl ether (2×50 ml) which was discarded, then acidified to pH=1–2 with 1M hydrochloric acid. The product was extracted into dichloromethane (3×50 ml), then the combined ethereal layers washed with water (2×50 ml), saturated aqueous sodium chloride solution (2×50 ml), dried (MgSO$_4$) and the solvent removed in vacuo to leave a residue. The residue was purified by chromatography over silica gel eluting with a gradient of methanol:dichloromethane 1:100→3:100. Appropriate fractions were combined and the solvents removed in vacuo was to give 2R-cyclohexylmethyl-4-morpholin-4-yl-4-oxo-butyric acid (25) as a white solid, yield 0.82 g, (71%). HPLC-MS (single peak with Rt=6.769 mins, 284.2 [M+H]$^+$, 589.2 [2M+Na]$^+$).

$\delta_H$ (400 MHz, CDCl$_3$ at 298K), 0.77–0.90 (2H, CH$_2$(cyclohexane), m), 1.05–1.40 (4H, CH$_2$(cyclohexane), m), 1.50–1.90 (7H, CH(cyclohexane), CH(cyclohexane), m), 2.30–2.44 (2Hβ, m), 2.64–2.77 (1Hα, m), 2.96–3.10 (1H, OH, brs), 3.40–3.78 (8H, CH$_2$OCH$_2$ and CH$_2$NCH$_2$, m).

Compound (25) was coupled under standard conditions to loaded building block-linker construct (11) (following standard removal of Fmoc), then cleaved to provide EXAMPLE 11.

Example 12

(3aR, 6aR) 2-Biphenyl-3-yl-4-methyl-pentanoic acid (3-oxo-hexahydrocyclopenta[b]furan-3a-yl)-amide

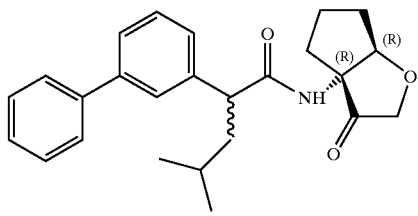

HPLC Rt=20.53 mins (>90%), HPLC-MS 392.3 [M+H]$^+$ (a) Preparation of Biphenyl-3-yl-acetic acid methyl ester (Compound (27), Scheme 8)

Concentrated sulphuric acid (588 μL) was added to a solution of 3-bromophenyl acetic acid (10 g, 46.5 mmol) in methanol (100 mL). The mixture was refluxed for 1.5 h and then cooled to ambient temperature and evaporated under reduced pressure to afford a residue. The residue was redissolved in diethyl ether (500 mL), washed with water (2×100 mL), brine (100 mL), dried (MgSO$_4$) and then evaporated under reduced pressure to afford 3-bromophenyl acetic acid methyl ester (10.65 g). The 3-bromophenyl acetic acid methyl ester was dissolved in toluene (117 mL) then phenyl boronic acid (6.8 g, 55.69 mmol) added, followed by a aqueous solution of sodium carbonate (93 mL, 2M) and tetrakis(triphenylphosphine)palladium (1.6 g, 1.41 mmol). The mixture was stirred overnight then cooled to ambient temperature and an aqueous solution of saturated ammonium chloride (100 mL) added. The mixture was extracted with ethyl acetate (2×200 mL), died (Na$_2$SO$_4$) and evaporated under reduced pressure to afford a residue. Flash chromatography of the residue over silica (200 g) using ethyl acetate:heptane (3:48) as the eluent gave biphenyl-3-yl acetic acid methyl ester, yield 10.5 g, (99%), TLC (single UV spot, R$_f$=0.24, 10% ethyl acetate in heptane), analytical HPLC R$_t$=19.55 min, HPLC-MS (single main UV peak with R$_t$=9.35 min, 227.1 [M+H]$^+$).

$\delta_H$ (400 MHz, CDCl$_3$ at 298K) 3.76 (2H, s, CH$_2$CO$_2$CH$_3$), 3.77 (3H, s, OCH$_3$), 7.34–7.66 (9H, m, biphenyl-3-yl).

(b) Preparation of Biphenyl-3-yl-acetic acid

Water (39 mL), followed by lithium hydroxide monohydrate (4.2 g, 101.5 mmol) were added to a solution of biphenyl-3-yl acetic acid methyl ester (11.43 g, 50.57 mmol) in methanol (265 mL). The mixture was stirred at ambient temperature for 2 h then the organics were removed under reduced pressure. The mixture was acidified with dilute hydrochloric acid (1M, 80 mL), extracted with chloroform (2×100 mL), dried (MgSO4) and evaporated under reduced pressure to afford biphenyl-3-yl acetic acid as a white solid, yield 10.6 g, (99%), analytical HPLC R$_t$=16.565 min, HPLC-MS (single main UV peak with R$_t$=7.91 min, 213.1 [M+H]$^+$).

$\delta_H$ (400 MHz, CDCl$_3$ at 298K) 3.77 (2H, s, CH$_2$CO$_2$CH$_3$), 7.28–7.52 (9H, m, biphenyl-3-yl).

(c) Preparation of 2RS-Biphenyl-3-yl-4-methylpent-4-enoic acid

A solution of biphenyl-3-yl acetic acid (7.0 g, 33 mmol) in anhydrous tetrahydrofuran (84 mL) was added dropwise to a solution of lithium diisopropyl amide (36.4 mL, 2M solution in hexanes) in anhydrous tetrahydrofuran (84 mL) at −78° C. The mixture was allowed to warm to 0° C. and stirred for 40 min. The mixture was then cooled to −78° C. and 3-bromo-2-methylpropene (4.97 mL) rapidly added. The mixture was stirred for 1 h at −78° C. then water (28 mL) added and the organics removed under reduced pressure. The mixture was then acidified with hydrochloric acid (6M, 14 ml), extracted with ethyl acetate (3×100 ml), dried (MgSO4) and evaporated under reduced pressure to afford a residue. Flash chromatography of the residue over silica (400 g) using methanol:dichloromethane (3:97) as the eluent afforded impure 2-biphenyl-3-yl-4-methylpentenoic acid (8.3 g). Flash chromatography over silica (400 g) using methanol:dichloromethane (1.5:98.5) afforded pure 2-biphenyl-3-yl-4-methylpent-4-enoic acid, yield 5.27 g, (60%), TLC (single UV spot, $R_f$=0.28, 5% methanol in dichloromethane), analytical HPLC $R_t$=19.99 min, HPLC-MS (single main UV peak with $R_t$=9.57 min, 267.1 [M+H]$^+$).

$\delta_H$ (400 MHz, CDCl$_3$ at 298K), 1.765 (3H, s, CH$_3$), 2.53 (1H, dd, J=6.6 and 14.7 Hz, 3-H$_1$), 2.91 (1H, dd, J=8.9 and 14.7 Hz, 3-H$_1$), 3.92 (1H, dd, J=6.6 and 8.9 Hz, 2-H), 4.79 (2H, d, J=10.7 Hz, 5-H$_2$), 7.30–7.62 (9H, m, biphenyl-3-yl).

(d) Preparation of 2RS-Biphenyl-3-yl-4-methylpentanoic acid (Compound (28), Scheme 8)

Palladium on carbon (10%, 300 mg) was added portionwise to a solution of 2RS-biphenyl-3-yl-4-methylpent-4-enoic acid (1 g, 3.76 mmol) in ethanol (40 mL) at 0° C. A hydrogen atmosphere was then introduced and the mixture allowed to warm to ambient temperature. The mixture was stirred for 18 h, then the hydrogen atmosphere removed and the mixture filtered over Celite and the catalyst washed with ethanol (40 mL). The combined organic filtrate was concentrated under reduced pressure to afford a residue, which was flash chromatographed over silica (150 g) using methanol:dichloromethane (1:99) as the eluent to afford 2RS-biphenyl-3-yl-4-methylpentanoic acid, yield 980 mg, (98%), TLC (single UV spot, $R_f$=0.45, 5% methanol in dichloromethane), analytical HPLC $R_t$=20.92 min, HPLC-MS (single main UV peak with $R_t$=10.15 min, 269.1 [M+H]$^+$, 291.1 [M+Na]$^+$).

$\delta_H$ (400 MHz, CDCl$_3$ at 298K), 0.93 (6H, d, J=6.6 Hz, 2×CH$_3$), 1.52–1.57 (1H, m, 4-H$_1$), 1.71–1.76 (1H, m, 3-H$_1$), 1.97–2.05 (1H, m, 3-H$_1$), 3.66 (1H, t, J=7.8 Hz, 2-H$_1$), 7.32–7.60 (9H, m, biphenyl-3-yl).

Compound (28) was coupled under standard conditions to loaded building block-linker construct (11), then cleaved to provide EXAMPLE 12.

Example A

Assays for Cysteine Protease Activity

The compounds of this invention may be tested in one of a number of literature based biochemical assays that are designed to elucidate the characteristics of compound inhibition. The data from these types of assays enables compound potency and the rates of reaction to be measured and quantified. This information, either alone or in combination with other information, would allow the amount of compound required to produce a given pharmacological effect to be determined.

General Materials and Methods

Unless otherwise stated, all general chemicals and biochemicals were purchased from either the Sigma Chemical Company, Poole, Dorset, U.K. or from Fisher Scientific UK, Loughborough, Leicestershire, U.K. Absorbance assays were carried out in flat-bottomed 96-well plates (Spectra; Greiner Bio-One Ltd., Stonehouse, Gloucestershire, U.K.) using a SpectraMax PLUS384 plate reader (Molecular Devices, Crawley, U.K.). Fluorescence high throughput assays were carried out in either 384-well microtitre plates (Corning Costar 3705 plates, Fisher Scientific) or 96-well 'U' bottomed Microfluor W1 microtitre plates (Thermo Labsystems, Ashford, Middlesex, U.K.). Fluorescence assays were monitored using a SpectraMax Gemini fluorescence plate reader (Molecular Devices). For substrates employing either a 7-amino-4-methylcoumarin (AMC) or a 7-amino-4-trifluoromethylcoumarin (AFC) fluorophore, assays were monitored at an excitation wavelength of 365 nm and an emission wavelength of 450 nm and the fluorescence plate reader calibrated with AMC. For substrates employing a 3-amino-benzoyl (Abz) fluorophore, assays were monitored at an excitation wavelength of 310 nm and an emission wavelength of 445 mm; the fluorescence plate reader calibrated with 3-amino-benzamide (Fluka). Unless otherwise indicated, all the peptidase substrates were purchased from Bachem UK, St. Helens, Merseyside, UK. Substrates utilizing fluorescence resonance energy transfer methodology (i.e. FRET-based substrates) were synthesized at Incenta Limited using published methods (Atherton & Sheppard, Solid Phase Peptide Synthesis, IRL Press, Oxford, U.K., 1989) and employed Abz (2-aminobenzoyl) as the fluorescence donor and 3-nitro-tyrosine [Tyr(NO$_2$)] as the fluorescence quencher (Meldal, M. and Breddam, K., Anal. Biochem., 195, 141–147, 1991). Hydroxyethylpiperazine ethanesulfonate (HEPES), tris-hydroxylmethyl aminomethane (tris) base, bis-tris-propane and all the biological detergents (e.g. CHAPS, zwittergents, etc.) were purchased from CN Biosciences UK, Beeston, Nottinghamshire, U.K. Glycerol was purchased from Amersham Pharmacia Biotech, Little Chalfont, Buckinghamshire, U.K. Stock solutions of substrate or inhibitor were made up to 10 mM in 100% dimethylsulfoxide (DMSO) (Rathburns, Glasgow, U.K.) and diluted as appropriately required. In all cases the DMSO concentration in the assays was maintained at less than 1% (vol./vol.).

Assay protocols were based on literature precedent (Table1; Barrett, A. J., Rawlings, N. D. and Woessner, J. F., 1998, Handbook of Proteolytic Enzymes, Academic Press, London and references therein) and modified as required to suit local assay protocols. Enzyme was added as required to initiate the reaction and the activity, as judged by the change in fluorescence upon conversion of substrate to product, was monitored over time. All assays were carried out at 25±1° C.

TABLE 1

The enzyme assays described herein were carried out according to literature precedents.

| Enzyme | Buffer | Substrate | Reference |
| --- | --- | --- | --- |
| Cathepsin B | I | Z-Phe-Arg-AMC | a, b |
| Cathepsin H | II | Bz-Phe-Val-Arg-AMC | a, b |
| Cathepsin L | I | Ac-Phe-Arg-AMC | b, c |
| Cathepsin S | I | Boc-Val-Leu-Lys-AMC | c, d |
| Caspase 1 | III | Ac-Leu-Glu-His-Asp-AMC | e |
| Caspase 2 | III | Z-Val-Asp-Val-Ala-Asp-AFC | f |
| Caspase 3 | III | Ac-Asp-Glu-Val-Asp-AMC | g, h |
| Caspase 4 | III | Suc-Tyr-Val-Ala-Asp-AMC | f |
| Caspase 5 | III | Ac-Leu-Glu-His-Asp-AMC | |
| Caspase 6 | III | Ac-Val-Glu-Ile-Asp-AMC | i, j, k |
| Caspase 7 | III | Ac-Asp-Glu-Val-Asp-AMC | |
| Caspase 8 | III | Ac-Ile-Glu-Thr-Asp-AMC | l |
| Caspase 9 | III | Ac-Leu-Glu-His-Asp-AMC | |
| Caspase 10 | III | Ac-Ile-Glu-Thr-Asp-AMC | |
| Cruzipain | IV | D-Val-Leu-Lys-AMC | m, n |

TABLE 1-continued

The enzyme assays described herein were carried out according to literature precedents.

| Enzyme | Buffer | Substrate | Reference |
|---|---|---|---|
| CPB2.8ΔCTE | XI | Pro-Phe-Arg-AMC | q |
| S. Aureus Extracellular cysteine peptidase | I | Abz-Ile-Ala-Ala-Pro-Tyr(NO$_2$)-Glu-NH$_2$ | o |
| Clostripain | | Z-Gly-Gly-Arg-AMC | p |
| FMDV LP | V | Abz-Arg-Lys-Leu-Lys-Gly-Ala-Gly-Ser-Tyr(NO$_2$)-Glu-NH$_2$ | r |
| Trypsin | VI | Z-Gly-Gly-Arg-AMC | s |
| Calpain μ | VII | Abz-Ala-Asn-Leu-Gly-Arg-Pro-Ala-Leu-Tyr(NO$_2$)-Asp-NH$_2$ | t |
| Calpain m | VIII | Abz-Lys-Leu-Cys(Bzl)-Phe-Ser-Lys-Gln-Tyr(NO$_2$)-Asp-NH$_2$ | t |
| Cathepsin K | IX | Z-Phe-Arg-AMC | u |
| Cathepsin X | X | | v, w |

I 10 mM BTP, pH 6.5 containing 1 mM EDTA, 5 mM 2-mercaptoethanol and 1 mM CaCl$_2$
II 10 mM BTP, pH 6.5 containing 1 mM EDTA, 142 mM NaCl, 1 mM DTT, 1 mM CaCl$_2$, 0.035 mM Zwittergent 3–16
III 50 mM HEPES pH 7.2, 10% Glycerol, 0.1% CHAPS, 142 mM NaCl, 1 mM EDTA, 5 mM DTT
IV 100 mM sodium phosphate, pH 6.75 containing 1 mM EDTA and 10 mM L-cysteine
V 50 mM trisacetate, pH 8.4 containing 1 mM EDTA, 10 mM L-cysteine and 0.25% (w/v) CHAPS
VI 10 mM HEPES, pH 8.0 containing 5 mM CaCl$_2$
VII 10 mM HEPES, pH 7.5 containing 2 mM 2-mercaptoethanol and 100 μM CaCl$_2$
VIII 10 mM HEPES, pH 7.5 containing 2 mM 2-mercaptoethanol and 200 μM CaCl$_2$
IX 100 mM sodium acetate; pH 5.5 containing 10 mM L-cysteine and 1 mM EDTA
X 100 mM sodium acetate; pH 5.5 containing 10 mM L-cysteine; 0.05% (w/v) Brij 35 and 1 mM EDTA
XI 100 mM sodium acetate; pH 5.5 containing 10 mM L-cysteine; 142 mM sodium chloride and 1 mM EDTA
a Barrett, A. J., Biochem. J., 187, 909–912, 1980
b Barrett, A. J. and Kirschke, H., Methods Enzymol., 80, 535–561, 1981
c Quibell, M. and Taylor, S., WO0069855, 2000
d Bromme, D., Steinert, ., Freibe, S., Fittkau, S., Wiederanders, B., and Kirschke, H., Biochem. J., 264, 475–481, 1989
e Rano, T. A., et. al., Chem. Biol., 4, 149, 1997
f Talanian, R. V., et. al., J. Biol. Chem., 272, 9677, 1997
g Lazebnik, Y. A., Kaufmann, S. H., Desnoyers, S., Poirer, G. G. and Earnshaw, W. C., Nature, 371, 768–774, 1994
h Han, Z., et. al., J. Biol. Chem., 272, 13432, 1997
i Takahashi, A., et. al., PNAS, 93, 8395, 1996
j Martins, L. M., et. al., J. Biol. Chem., 272, 7421, 1997
k Nagata, S., Cell., 88, 355, 1997
l Harris, J. L., et. al., J. Biol. Chem., 273, 27364, 1998
m Cazzulo, J. J., Cazzulo Franke, M. C., Martinez, J. and Franke de Cazzulo, B. M., Biochim. Biophys. Acta., 1037, 186–191, 1990
n Cazzulo, J. J., Bravo, M., Raimondi, A., Engstrom, U., Lindeberg, G. and Hellman, U., Cell Mol. Biol., 42, 691–696, 1996
o Potempa, J., Dubin, A., Korzus, G. and Travis, J., Biochem. J., 263, 2664–2667, 1988
p Kembhavi, A. A., Buttle, D. J., Rauber, P. and Barrett, A. J., FEBS Lett., 283, 277–280, 1991
q Alves, L. C., et. al., Mol. Biochem. Parasitol, 116, 1–9, 2001.
r Guarne, et. al., J. Mol. Biol., 302, 1227–1240, 2000.
s Halfon and Craik, (Barret, Rawlings and Woessner, eds.), in Handbook of Proteolytic Enzymes, Academic Press, London, 12–21, 1998.
t Sasaki, et. al., (1984), J. Biol. Chem., 259, 12489–12494, 1984.
u Bossard, M. J., et. al., , J. Biol. Chem., 21, 12517–12524, 1996
v Santamaria, I., et. al., J. Biol. Chem., 273, 16816–16823, 1998
w Klemencic, J, et al., Eur. J. Biochem., 267, 5404–5412, 2000

*Trypanosoma cruzi* Cruzipain Peptidase Activity Assays

Wild-type cruzipain, derived from *Trypanosoma cruzi* Dm28 epimastigotes, was obtained from Dr. Julio Scharfstein (Instituto de Biofisica Carlos Chagas Filho, Universidade Federal do Rio de Janeiro, Rio de Janeiro, Brazil). Activity assays were carried out in 100 mM sodium phosphate, pH 6.75 containing 1 mM EDTA and 10 mM L-cysteine using 2.5 mM enzyme. Ac-Phe-Arg-AMC ($K_M^{app} \approx 12$ μM) and D-Val-Leu-Lys-AMC ($K_M^{app} \approx 4$ μM) were used as the substrates. Routinely, Ac-FR-AMC was used at a concentration equivalent to $K_M^{app}$ and D-Val-Leu-Lys-AMC was used at a concentration of 25 μM. The rate of conversion of substrate to product was derived from the slope of the increase in fluorescence monitored continuously over time.

*Leishmania mexicana* Cysteine Protease B (CPB) Peptidase Activity Assays

Wild-type recombinant CPB without the C-terminal extention (i.e. CPB2.8ΔCTE; Sanderson, S. J., et. al., *Biochem J.*, 347, 383–388, 2000) was obtained from Dr. Jeremy Mottram (Wellcome Centre for Molecular Parasitology, The Anderson College, University of Glasgow, Glasgow, U.K.). Activity assays were carried out in 100 mM sodium acetate; pH 5.5 containing 1 mM EDTA; 200 mM NaCl and 10 mM DTT (Alves, L. C., et. al., *Mol. Biochem. Parasitol*, 116, 1–9, 2001) using 0.25 nM enzyme. Pro-Phe-Arg-AMC ($K_M^{app} \approx 38$ μM) was used as the substrate at a concentration equivalent to $K_M^{app}$. The rate of conversion of substrate to product was derived from the slope of the increase in fluorescence monitored continuously over time.

Cathepsin Peptidase Activity Assays

Bovine cathepsin S, human cathepsin L, human cathepsin H and human cathepsin B were obtained from CN Biosciences. Recombinant human cathepsin S, human cathepsin K and human cathepsin X were obtained from Dr. Boris Turk (Josef Stefan Institute, Ljubljana, Slovenia). Unless otherwise stated, all peptidase activity assays were carried out in 10 mM bis-tris-propane (BTP), pH 6.5 containing 1 mM BDTA, 5 mM 2-mercaptoethanol and 1 mM CaCl$_2$. Human cathepsin H activity assays were carried out in 10 mM BTP pH 6.5, 142 mM NaCl$_2$, 1 mM CaCl$_2$, 1 mM EDTA, 1 mM DTT, 0.035 mM Zwittergent 3–16. Human cathepsin K assays were carried out in 100 mM sodium acetate; pH 5.5 containing 20 mM L-cysteine and 1 mM EDTA (Bossard, M. J., et. al., *J. Biol. Chem.*, 21, 12517–12524, 1996). Human cathepsin X assays were carried out in 100 mM sodium acetate; pH 5.5 containing 20 mM L-cysteine; 0.05% (w/v) Brij 35 and 1 mM EDTA (Santamaria, I., et. al., *J. Biol. Chem.*, 273, 16816–16823, 1998; Klemencic, J, et al., *Eur. J. Biochem.*, 267, 5404–5412, 2000). The final enzyme concentrations used in the assays were 0.5 nM bovine cathepsin S, 1 nM cathepsin L, 0.1 nM cathepsin B, 0.25 nM Cathepsin K; 1 nM cathepsin X and 10 nM cathepsin H. For the inhibition assays, the substrates used for cathepsin S, cathepsin L, cathepsin B, cathepsin K and cathepsin H were boc-Val-Leu-Lys-AMC ($K_M^{app} \approx 30$ μM), Ac-Phe-Arg-AMC ($K_M^{app} \approx 20$ μM), Z-Phe-Arg-AMC ($K_M^{app} \approx 40$ μM), Z-Leu-Arg-AMC ($K_M^{app} \approx 2$ μM); Bz-Phe-Val-Arg-AMC ($K_M^{app} \approx 150$ μM) respectively. In each case the substrate concentration used in each assay was equivalent to the $K_M^{app}$. The rate of conversion of substrate to product was derived from the slope of the increase in fluorescence monitored continuously over time.

Trypsin Peptidase Activity Assays

Human pancreatic trypsin (iodination grade; CN Biosciences) activity assays were carried out in 10 mM HEPES, pH 8.0 containing 5 mM CaCl$_2$ using 0.1 nM trypsin. For the inhibition assays, Z-Gly-Gly-Arg-AMC ($K_M^{app} \approx 84$ μM) was used as the substrate at a concentration equivalent to $K_M^{app}$. The rate of conversion of substrate to product was derived from the slope of the increase in fluorescence monitored continuously over time.

Clostripain Peptidase Activity Assays

Clostripain (Sigma) activity assays were carried out in 10 mM BTP, pH 6.5 containing 1 mM EDTA, 5 mM 2-mercaptoethanol and 1 mM $CaCl_2$ using 0.3 nM enzyme. For the inhibition assays, Z-Gly-Gly-Arg-AMC ($K_M^{app} \approx 100$ μM) was used as the substrate at a concentration equivalent to $K_M^{app}$. The rate of conversion of substrate to product was derived from the slope of the increase in fluorescence monitored continuously over time.

Calpain Peptidase Activity Assays

Calpain (human erythrocyte μ-calpain and porcine kidney m-calpain; CN Biosciences) activity assays were carried out in 10 mM HEPES, pH 7.5 containing 2 mM 2-mercaptoethanol and $CaCl_2$ using 25 nM of either enzyme (Sasaki, et. al., *J. Biol. Chem.*, 259, 12489–12494, 1984). For μ-calpain inhibition assays, the buffer contained 100 μM $CaCl_2$ and Abz-Ala-Asn-Leu-Gly-Arg-Pro-Ala-Leu-Tyr($NO_2$)-Asp-$NH_2$ ($K_M^{app} \approx 20$ μM; Incenta Limited) was used as the substrate. For m-calpain inhibition assays, the assay buffer contained 200 μM $CaCl_2$ and Abz-Lys-Leu-Cys(Bzl)-Phe-Ser-Lys-Gln-Tyr($NO_2$)-Asp-$NH_2$ ($K_M^{app} \approx 22$ μM; Incenta Limited) was used as the substrate. In both cases the substrate concentration employed in the assays was equivalent to $K_M^{app}$. The rate of conversion of substrate to product was derived from the slope of the increase in fluorescence monitored continuously over time.

Extracellular *S. aureus* V8 Cysteine Peptidase (Staphylopain) Peptidase Activity Assays

*S. aureus* V8 was obtained from Prof. S. Arvidson, Karolinska Institute, Stockholm, Sweden. Extracellular *S. aureus* V8 cysteine peptidase (staphylopain) activity assays were carried out using partially purified *S. aureus* V8 culture supernatant (obtained from Dr. Peter Lambert, Aston University, Birmingham, U.K.). Activity assays were carried out in 10 mM BTP, pH 6.5 containing 1 mM EDTA, 5 mM 2-mercaptoethanol and 1 mM $CaCl_2$ using two-times diluted partially purified extract. For the inhibition assays, Abz-Ile-Ala-Ala-Pro-Tyr($NO_2$)-Glu-$NH_2$ ($K_M^{app} \approx 117$ μM; Incenta Limited) was used as the substrate at a concentration equivalent to $K_M^{app}$. The rate of conversion of substrate to product was derived from the slope of the increase in fluorescence monitored continuously over time.

Foot-and-mouth Disease Leader Peptidase (FMDV-LP) Activity Assays

Recombinant wild-type FMDV-LP was obtained from Dr. Tim Skern (Institut für Medizinische Biochemie, Abteilung für Biochemie, Universtät Wien, Wien, Austria). Activity assays were carried out in 50 mM trisacetate, pH 8.4 containing 1 mM EDTA, 10 mM L-cysteine and 0.25% (w/v) CHAPS using 10 nM enzyme. For the inhibition assays, Abz-Arg-Lys-Leu-Lys-Gly-Ala-Gly-Ser-Tyr($NO_2$)-Glu-$NH_2$ ($K_M^{app} \approx 51$ μM, Incenta Limited) was used as the substrate at a concentration equivalent to $K_M^{app}$. The rate of conversion of substrate to product was derived from the slope of the increase in fluorescence monitored continuously over time.

Caspase Peptidase Activity Assays

Caspases 1–10 were obtained from CN Biosciences or BioVision Inc. (Mountain View, Calif., USA) and all assays were carried out in 50 mM HEPES; pH 7.2, 10% (v/v) glycerol, 0.1% (w/v) CHAPS, 142 mM NaCl, 1 mM EDTA, 5 mM dithiothreitol (DTT) using 0.1–1 U per assay. For caspase 1, Ac-Leu-Glu-His-Asp-AMC was used as the substrate; for caspase 2, Z-Val-Asp-Val-Ala-Asp-AFC was used as the substrate; for caspase 3, Ac-Asp-Glu-Val-Asp-AMC was used as the substrate; for caspase 4, Suc-Tyr-Val-Ala-Asp-AMC was used as the substrate; for caspase 5, Ac-Leu-Glu-His-Asp-AMC was used as the substrate; for caspase 6, Ac-Val-Glu-Ile-Asp-AMC was used as the substrate; for caspase 7, Ac-Asp-Glu-Val-Asp-AMC was used as the substrate; for caspase 8, Ac-Ile-Glu-Thr-Asp-AMC was used as the substrate; for caspase 9, Ac-Leu-Glu-His-Asp-AMC was used as the substrate; for caspase 10, Ac-Ile-Glu-Thr-Asp-AMC was used as the substrate (Nicholson, D. W. and Thornberry, N. A., *TIBS,* 22, 299–306, 1997; Stennicke, H. R. and Salvesen, G. S., *J. Biol. Chem.*, 272(41), 25719–25723, 1997; Talanian, R. V., et. al., *J. Biol. Chem.*, 272(15), 9677–9682, 1997; Wolf, B. B. and Green, D. R., *J. Biol. Chem.*, 274(29), 20049–20052, 1999). The rate of conversion of substrate to product was derived from the slope of the increase in fluorescence monitored continuously over time.

Measurement of the Apparent Macroscopic Binding (Michaelis) Constants ($K_M^{app}$) for Substrates The apparent macroscopic binding constant ($K_M^{app}$) for each substrate was calculated, from the dependence of enzyme activity as a function of substrate concentration. The observed rates were plotted on the ordinate against the related substrate concentration on the abscissa and the data fitted by direct regression analysis (Prism v 3.02; GraphPad, San Diego, USA) using Equation 1 (Cornish-Bowden, A. *Fundamentals of enzyme kinetics* Portland Press; 1995, 93–128.).

$$v_i = \frac{V_{max}^{app} \cdot [S_o]}{[S_o] + K_M^{app}} \quad (1)$$

In Equation 1 '$v_i$' is the observed initial rate, '$V_{max}^{app}$' is the observed maximum activity at saturating substrate concentration, '$K_M^{app}$' is the apparent macroscopic binding (Michaelis) constant for the substrate, '[$S_o$]' is the initial substrate concentration.

Measurement of the Inhibition Constants

The apparent inhibition constant ($K_i$) for each compound was determined on the basis that inhibition was reversible and occurred by a pure-competitive mechanism. The $K_i$ values were calculated, from the dependence of enzyme activity as a function of inhibitor concentration, by direct regression analysis (Prism v 3.02) using Equation 2 (Cornish-Bowden, A., 1995.).

$$v_i = \frac{V_{max}^{app} \cdot [S]}{[S] + \{K_M^{app} \cdot ([I]/K_i)\}} \quad (2)$$

In Equation 2 '$v_i$' is the observed residual activity, '$V_{max}^{app}$' is the observed maximum activity (i.e. in the absence of inhibitor), '$K_M^{app}$' is the apparent macroscopic binding (Michaelis) constant for the substrate, '[S]' is the initial substrate concentration, '$K_i$' is the apparent dissociation constant and '[I]' is the inhibitor concentration.

In situations where the apparent dissociation constant ($K_i^{app}$) approached the enzyme concentrations, the $K_i^{app}$ values were calculated using a quadratic solution in the form described by Equation 3 (Morrison, J. F. *Trends Biochem. Sci.*, 7, 102–105, 1982; Morrison, J. F. *Biochim. Biophys. Acta*, 185, 269–286, 1969; Stone, S. R. and Hofsteenge, J. *Biochemistry*, 25, 4622–4628, 1986).

$$v_i = \frac{F\{E_o - I_o - K_i^{app} + \sqrt{(E_o - I_o - K_i^{app})^2 + 4 \cdot K_i^{app} \cdot E_o}\}}{2} \quad (3)$$

$$K_i^{app} = K_i(1 + [S_o]/K_M^{app}) \quad (4)$$

In Equation 3 '$v_i$' is the observed residual activity, 'F' is the difference between the maximum activity (i.e. in the absence of inhibitor) and minimum enzyme activity, '$E_o$' is the total enzyme concentration, '$K_i^{app}$' is the apparent dissociation constant and '$I_o$' is the inhibitor concentration. Curves were fitted by non-linear regression analysis (Prism) using a fixed value for the enzyme concentration. Equation 4 was used to account for the substrate kinetics, where '$K_i$' is the inhibition constant, '$[S_o]$' is the initial substrate concentration and '$K_M^{app}$' is the apparent macroscopic binding (Michaelis) constant for the substrate (Morrison, 1982). The Second-order Rate of Reaction of Inhibitor with Enzyme Where applicable, the concentration dependence of the observed rate of reaction ($k_{obs}$) of each compound with enzyme was analysed by determining the rate of enzyme inactivation under pseudo-first order conditions in the presence of substrate (Morrison, J. F., *TIBS*, 102–105, 1982; Tian, W. X. and Tsou, C. L., *Biochemistry*, 21, 1028–1032, 1982; Morrison, J. F. and Walsh, C. T., from Meister (Ed.), *Advances in Enzymol.*, 61, 201–301, 1988; Tsou, C. L., from Meister (Ed.), *Advances in Enzymol.*, 61, 381–436, 1988;). Assays were carried out by addition of various concentrations of inhibitor to assay buffer containing substrate. Assays were initiated by the addition of enzyme to the reaction mixture and the change in fluorescence monitored over time. During the course of the assay less than 10% of the substrate was consumed.

$$F = v_s t + \frac{(v_o - v_s)[1 - e^{(k_{obs} \cdot t)}]}{k_{obs}} + D \quad (5)$$

The activity fluorescence progress curves were fitted by non-linear regression analysis (Prism) using Eq. 5 (Morrison, 1969; Morrison, 1982); where 'F' is the fluorescence response, 't' is time, '$v_o$' is the initial velocity, '$v_s$' is the equilibrium steady-state velocity, '$k_{obs}$' is the observed pseudo first-order rate constant and 'D' is the intercept at time zero (i.e. the ordinate displacement of the curve). The second order rate constant was obtained from the slope of the line of a plot of $k_{obs}$ versus the inhibitor concentration (i.e. $k_{obs}/[I]$). To correct for substrate kinetics, Eq. 6 was used, where '$[S_o]$' is the initial substrate concentration and '$K_M^{app}$' is the apparent macroscopic binding (Michaelis) constant for the substrate.

$$k_{inact} = \frac{k_{obs}(1 + [S_o]/K_M^{app})}{[I]} \quad (6)$$

Compounds of the invention were tested by the above described assays and observed to exhibit cruzipain inhibitory activity or inhibitory activity against an alternative CA C1 cysteine protease with an in vitro Ki inhibitory constant of less than or equal to 100 $\mu$M. Exemplary inhibition data for a number of example compounds of the invention are given in table 2.

TABLE 2

Exemplary inhibition data (Ki expressed as $\mu$M).

| EXAMPLE N° | Cruzipain | Bovine Cathepsin S | Human Cathepsin L | Human Cathepsin K |
|---|---|---|---|---|
| 1 | <2 | >50 | >20 | >100 |
| 7 | >50 | <2 | >25 | >50 |
| 6 | >20 | >25 | >10 | <2 |

What is claimed is:
1. A compound according to general formula (I):

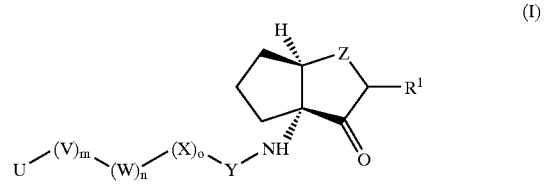

wherein: $R^1 = C_{0-7}$-alkyl (when C=0, $R^1$ is simply hydrogen), $C_{3-6}$-cycloalkyl or Ar—$C_{0-7}$-alkyl (when C=0, $R^1$ is simply an aromatic moiety Ar);

Ar is an aromatic moiety which is a 5- or 6-membered monocyclic or 9- or 10-membered bicyclic ring, wherein the aromatic ring is optionally substituted;

Z=O or S;

Y=$CR^5R^6$—CO, where $R^5$ and $R^6$ are independently chosen from $C_{0-7}$-alkyl, $C_{3-6}$-cycloalkyl or Ar—$C_{0-7}$-alkyl;

$(X)_o = CR^7R^8$, where $R^7$ and $R^8$ are independently chosen from $C_{0-7}$-alkyl, $C_{3-6}$-cycloalkyl and Ar—$C_{0-7}$-alkyl and o is a number from zero to three;

$(W)_n$ = O, S, C(O), S(O) or S(O)$_2$ or NR$^9$, where R$^9$ is chosen from $C_{0-7}$-alkyl, $C_{3-6}$-cycloalkyl and Ar—$C_{0-7}$-alkyl and n is zero or one;

$(V)_m$ = C(O), C(S), S(O), S(O)$_2$, S(O)$_2$NH, OC(O), NHC(O), NHS(O), NHS(O)$_2$, OC(O)NH, C(O)NH or $CR^{10}OR^{11}$, where $R^{10}$ and $R^{11}$ are independently chosen from $C_{0-7}$-alkyl, $C_{3-6}$-cycloalkyl, Ar—$C_{0-7}$-alkyl and m is a number from zero to three, provided that when m is greater than one, $(V)_m$ contains a maximum of one carbonyl or sulphonyl group;

U=a stable 5- to 7-membered monocyclic or a stable 8- to 11-membered bicyclic ring which is either saturated or unsaturated and which includes zero to four heteroatoms (as detailed below), said ring selected from:

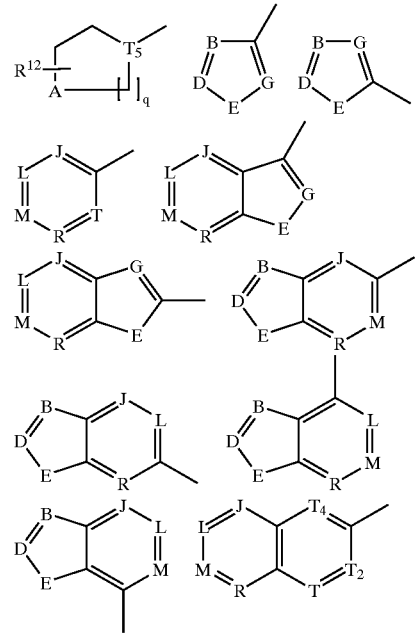

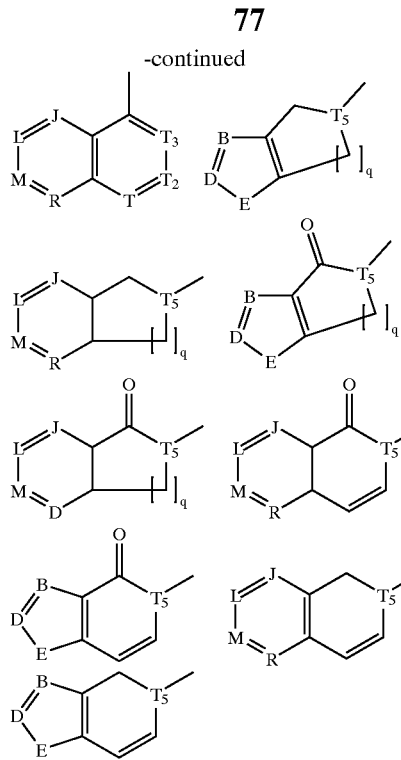

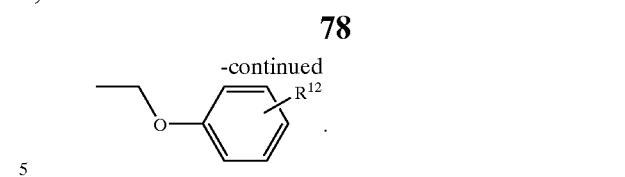

wherein R¹² is:
- $C_{0-7}$-alkyl, $C_{3-6}$-cycloalkyl, Ar—$C_{0-7}$-alkyl, O—$C_{0-7}$-alkyl, O—$C_{3-6}$-cycloalkyl, O—Ar—$C_{0-7}$-alkyl, S—$C_{0-7}$-alkyl, S—$C_{3-6}$-cycloalkyl, S—Ar—$C_{0-7}$-alkyl, NH—$C_{0-7}$-alkyl, NH—$C_{3-6}$-cycloalkyl, NH—Ar—$C_{0-7}$-alkyl, N($C_{0-7}$-alkyl)$_2$, N($C_{3-6}$-cycloalkyl)$_2$ or N(Ar—$C_{0-7}$-alkyl)$_2$ or, when it is part of the group CHR¹² or CR¹², R¹² may be halogen;

A is chosen from:
- $CH_2$, CHR¹², O, S and NR¹³;
  wherein R¹² is as defined above and R¹³ is chosen from:
    $C_{0-7}$-alkyl, $C_{3-6}$-cycloalkyl and Ar—$C_{0-7}$-alkyl;

B, D and G are independently chosen from:
- CR¹², where R¹² is as defined above, or N;

E is chosen from:
- $CH_2$, CHR¹², O, S and NR¹³, where R¹² and R¹³ are defined as above;

J, L, M, R, T, $T_2$, $T_3$ and $T_4$ are independently chosen from:
- CR¹² and N, where R¹² is as defined above;

$T_5$ is chosen from:
- CH or N;

q is a number from one to three, thereby defining a 5-, 6- or 7-membered ring.

2. A compound as claimed in claim 1 wherein Z is O.

3. A compound as claimed in claim 1 wherein R¹ is $C_{0-7}$-alkyl or Ar—$C_{0-7}$-alkyl.

4. A compound as claimed in claim 3 wherein R¹ is selected from hydrogen or one of the following moieties:

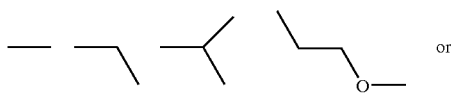

5. A compound as claimed in claim 1 wherein Y is CR⁵R⁶CO where R⁵ and R⁶ are independently selected from $C_{0-7}$-alkyl, $C_{3-6}$-cycloalkyl or Ar—$C_{0-7}$-alkyl.

6. A compound as claimed in claim 5 where Y is selected from one of the following moieties:

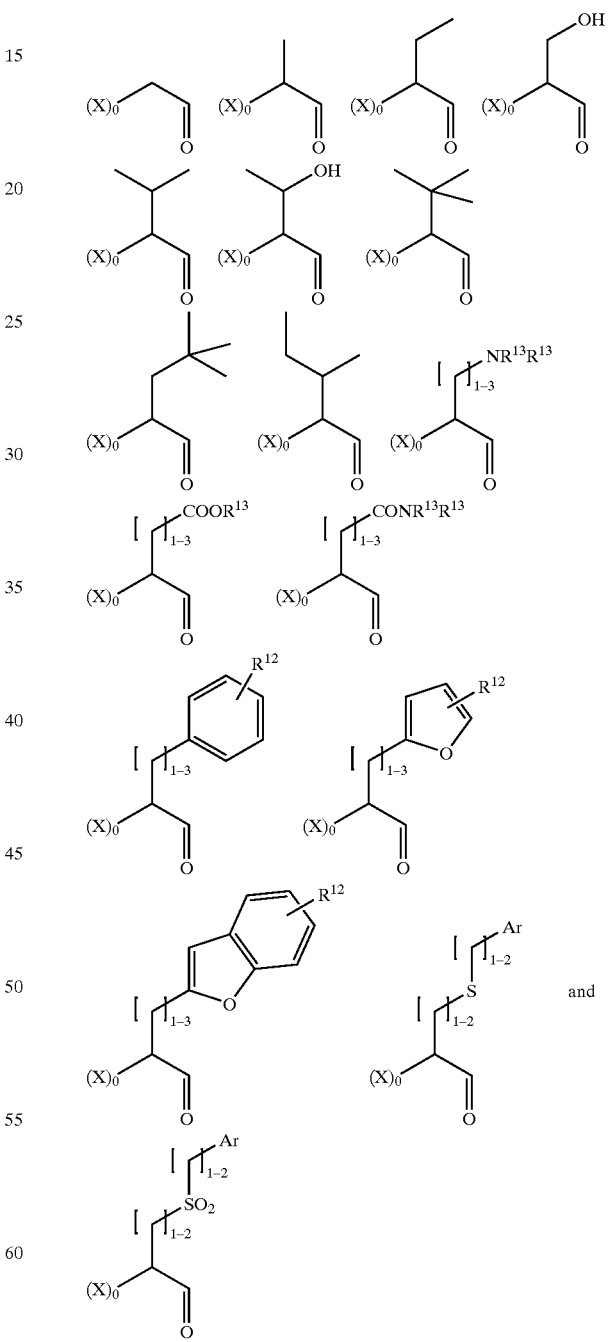

wherein R¹², R¹³ and Ar are as defined above.

7. A compound as claimed in claim 1 wherein Y is CHR$^6$CO where R$^6$ is Ar—CH$_2$—, where the aromatic ring is an optionally substituted phenyl or monocyclic heterocycle.

8. A compound as claimed in claim 1 wherein Y is CHR$^6$CO where R$^6$ is a branched alkyl group or a straight heteroalkyl chain.

9. A compound as claimed in claim 1 wherein Y is CHR$^6$CO where R$^6$ is cyclohexylmethyl.

10. A compound as claimed in claim 1 wherein Y is selected from the following:

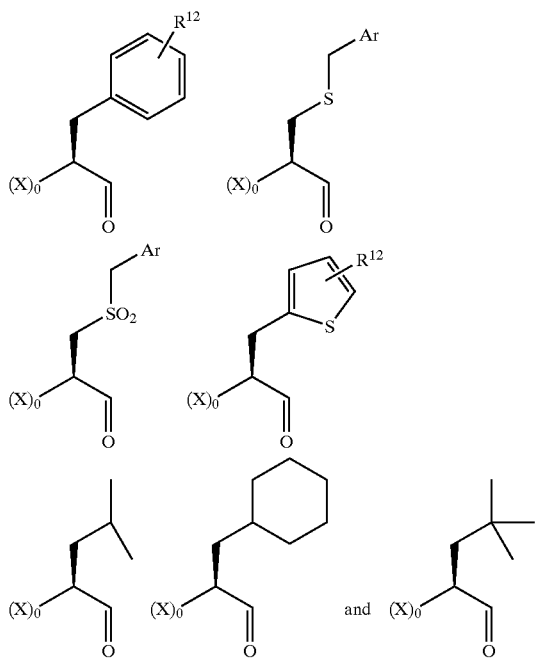

wherein (X)$_o$, R$^{12}$ and Ar are as defined previously.

11. A compound as claimed in claim 1 wherein, in the group (X)$_o$, X is CR$^7$R$^8$ and each of R$^7$ and R$^8$ is independently selected from C$_{0-7}$-alkyl or Ar—C$_{0-7}$-alkyl.

12. A compound as claimed in claim 1 wherein (X)$_o$ is one of the following moieties:

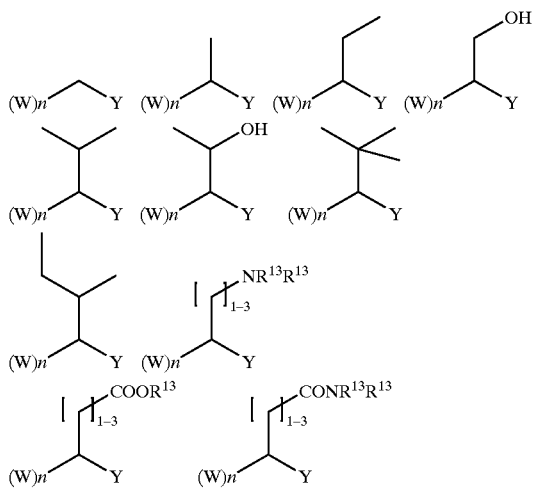

-continued

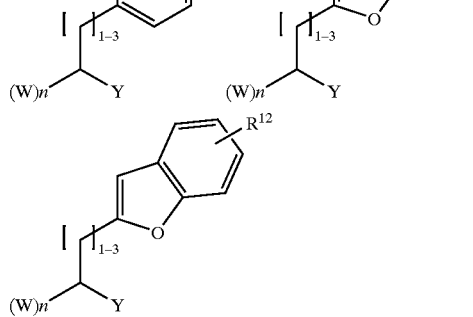

wherein R$^{12}$ and R$^{13}$ are as defined previously.

13. A compound as claimed in claim 1, wherein (X)$_o$ is an alkyl group and where o=0 or 1.

14. A compound as claimed in claim 1 wherein, in the group (W)$_n$:

W is O, S, SO$_2$, SO, C(O) or NR$^9$, where R$^9$ is C$_{0-4}$-alkyl; and n is 0 or 1.

15. A compound as claimed in claim 1 wherein, in the group (W)$_n$:

W is O, S, SO$_2$, C(O) or NH, and n is 0 or 1.

16. A compound as claimed in claim 1 wherein, in the group (W)$_n$:

W is NH and n is 1.

17. A compound as claimed in claim 1 wherein, in the group (V)$_m$:

V is C(O), C(O)NH or CHR$^{11}$, where R$^{11}$ is C$_{0-4}$-alkyl; and m is 0 or 1.

18. A compound as claimed in claim 1 wherein the combination (V)$_m$ and (W)$_m$ is one of the following:

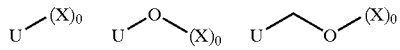

'n' = 0    'n' = 1    'n' = 1
'm' = 0    'W' = O    'W' = O
           'm' = 0    'V' = CH$_2$
                      'm' = 1

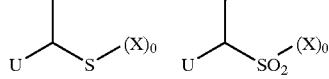

'n' = 1            'n' = 1
'W' = S            'W' = SO$_2$
'V' = CH(CH$_3$)   'V' = CH(CH$_2$CH$_3$)
'm' = 1            'm' = 1

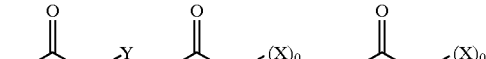

'n' = 0       'n' = 1       (X) > 0
'V' = C(O)    'W' = O       'n' = 1
'm' = 1       'V' = C(O)    'W' = NR$^9$
              'm' = 1       R$^9$ = H
                            'V' = C(O)
                            'm' = 1

-continued

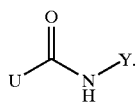

(X)₀ = '-'
'n' = 1
'W' = NR⁹
R⁹ = H
'V' = C(O)
'm' = 1

19. A compound as claimed in claim 18, wherein the combination (V)$_m$ and (W)$_m$ is one of the first eight structures depicted in claim 18.

20. A compound as claimed in claim 18, wherein the combination (V)$_m$ and (W)$_m$ is the ninth structure depicted in claim 18.

21. A compound as claimed in claim 1 wherein the combination (X)$_o$, (V)$_m$ and (W)$_m$ is one of the following:

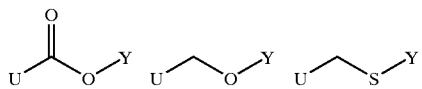

(X)₀ = '-'       (X)₀ = '-'       (X)₀ = '-'
(W)$_n$ = 'O'    (W)$_n$ = 'O'    (W)$_n$ = 'S'
(V)$_m$ = 'C(O)' (V)$_m$ = 'CH₂'  (V)$_m$ = 'CH₂'

(X)₀ = '-'       (X)₀ = 'CH₂'     (X)₀ = '-'
(W)$_n$ = 'SO₂'  (W)$_n$ = 'C(O)' (W)$_n$ = 'NH'
(V)$_m$ = 'CH₂'  (V)$_m$ = '-'    (V)$_m$ = 'C(O)'

22. A compound as claimed in claim 1 wherein U is an optionally substituted 5- or 6-membered saturated or unsaturated heterocycle or an optionally substituted saturated or unsaturated 9- or 10-membered heterocycle.

23. A compound as claimed in claim 22 wherein U is one of the following:

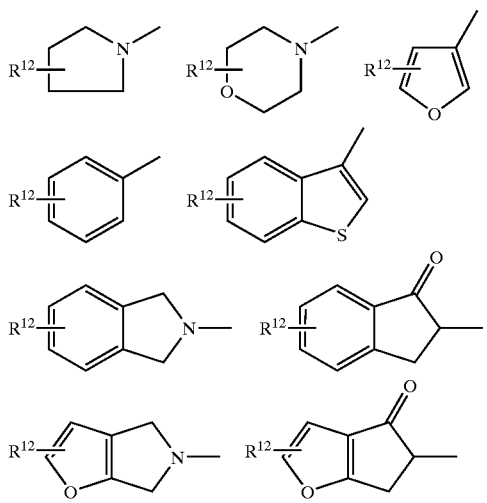

-continued

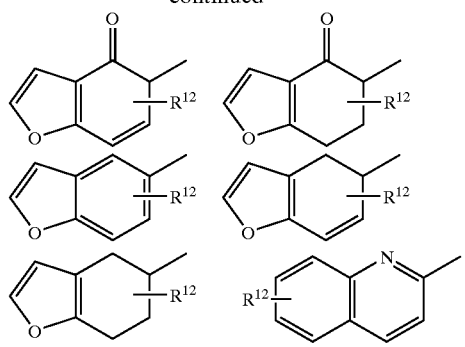

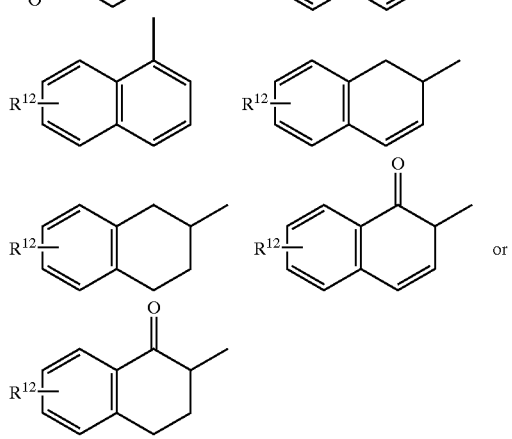

wherein R$^{12}$ is as defined previously.

24. A compound as claimed in claim 1 wherein U is a bulky alkyl or aryl group at the para position of an aryl Ar.

25. A compound as claimed in claim 1 wherein U is a meta or para-biaryl Ar—Ar, where Ar is as previously defined.

26. A compound as claimed in claim 1, wherein U represents a group selected from:

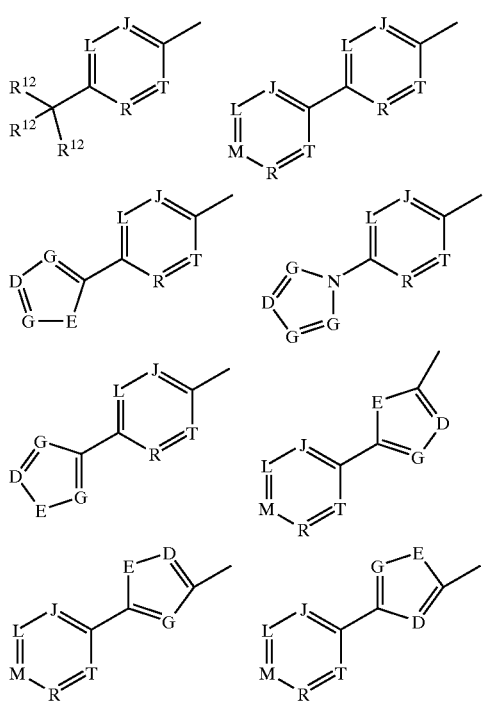

-continued
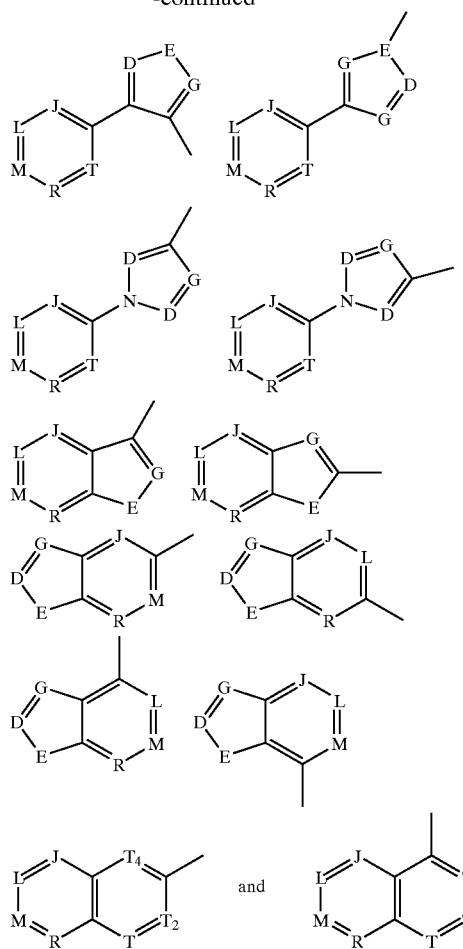
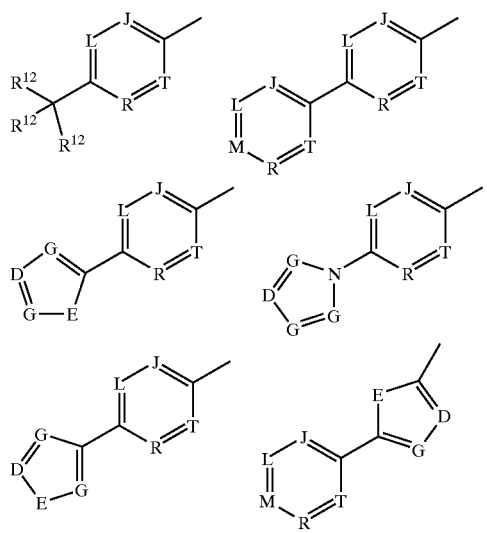
where $R^{12}$, D, E, G, J, L, M, R, T, $T_2$, $T_3$ and $T_4$ are defined previously.
27. A compound as claimed in claim 1, wherein U represents a group selected from:
-continued
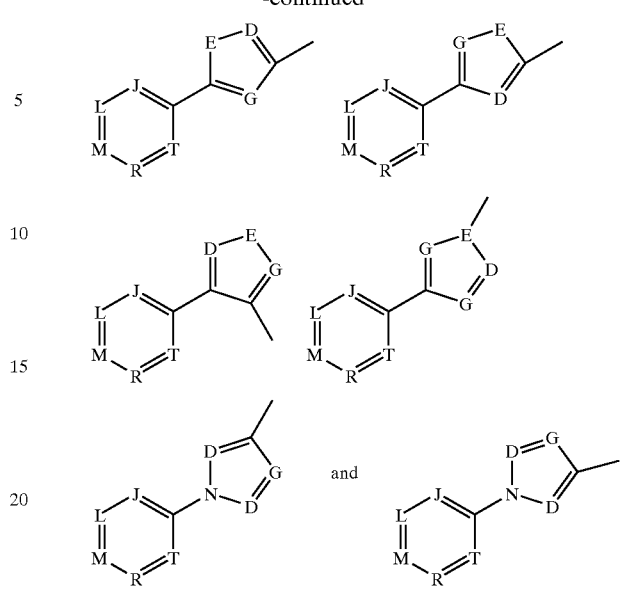
wherein $R^{12}$, D, E, G, J, L, M, R and T are as defined previously.
28. A compound as claimed in claim 1, wherein U represents a group selected from:
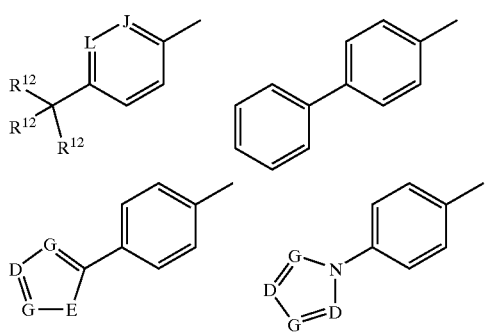
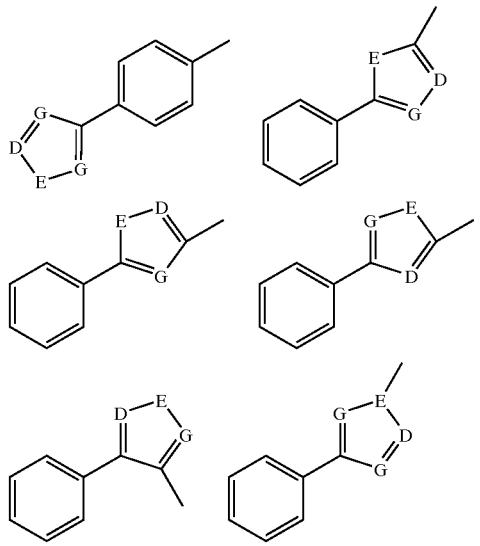

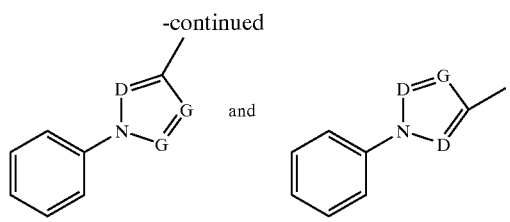

wherein $R^{12}$, D, E, G, J and L are as defined previously.

29. A method of validating a known or putative cysteine protease as a therapeutic target, the method comprising:
(a) assessing the in vitro binding of a compound as claimed in claim 1 to an isolated known or putative cysteine protease, providing a measure of 'potency'; and optionally, one or more of the steps of:
(b) assessing the binding of a compound as claimed in claim 1 to closely related homologous proteases of the target and general house-keeping proteases (e.g. trypsin) to provides a measure of 'selectivity';
(c) monitoring a cell-based functional marker of a particular cysteine protease activity, in the presence of a compound as claimed in claim 1; and
(d) monitoring an animal model-based functional marker of a particular cysteine protease activity, in the presence of a compound as claimed in claim 1.

30. A composition comprising one or more compounds as claimed in claim 1 and a pharmaceutically or veterinarily acceptable carrier.

31. A method for preventing or treating Chagas' disease comprising administering an effective amount of one or more compounds of claim 1 to a patient in need of such prevention or treatment.

32. A compound as claimed in claim 8, wherein $R^6$ is isobutyl.

33. A compound as claimed in claim 8, wherein $R^6$ is benzylsulfanylmethyl or benzylsulphonylmethyl.

34. A compound as claimed in claim 13, wherein $(X)_o$ is methylene.

35. A method for preventing or treating a disease resulting from elevated levels of cysteine protease selected from the group consisting of infections by *Pneumocystis carinii, Trypsanoma cruzi, Trypsanoma brucei, Crithidia fusiculata, Leishmania mexicana, Clostridium histolyticum* and *Staphylococcus aureas* comprising administering to a patient in need of such prevention or treatment an effective amount of one or more compounds as claimed in claim 1.

* * * * *